(12) United States Patent
Lynch et al.

(10) Patent No.: US 9,242,993 B2
(45) Date of Patent: Jan. 26, 2016

(54) MORPHOLINO SUBSTITUTED BICYCLIC PYRIMIDINE UREA OR CARBAMATE DERIVATIVES AS MTOR INHIBITORS

(71) Applicant: CELLZOME LIMITED, Middlesex (GB)

(72) Inventors: Rosemary Lynch, Cambridge (GB); Andrew David Cansfield, Cambridge (GB); Daniel Paul Hardy, Baldock (GB); John Thomas Feutrill, Rosanna (AU); Rita Adrego, Brandon (GB); Katie Ellard, Herts (GB); Tammy Ladduwahetty, Longon (GB)

(73) Assignee: CELLZOME LIMITED, Brentford, Middlesex (GB)

( * ) Notice: Subject to any disclaimer, the term of this patent is extended or adjusted under 35 U.S.C. 154(b) by 0 days.

(21) Appl. No.: 14/350,167

(22) PCT Filed: Oct. 5, 2012

(86) PCT No.: PCT/EP2012/069676
§ 371 (c)(1),
(2) Date: Apr. 7, 2014

(87) PCT Pub. No.: WO2013/050508
PCT Pub. Date: Apr. 11, 2013

(65) Prior Publication Data
US 2014/0288066 A1    Sep. 25, 2014

Related U.S. Application Data

(60) Provisional application No. 61/649,995, filed on May 22, 2012.

(30) Foreign Application Priority Data

Oct. 7, 2011    (EP) .................................... 11184358

(51) Int. Cl.
| | | |
|---|---|---|
| *A61K 31/5377* | (2006.01) | |
| *A61K 31/5386* | (2006.01) | |
| *A61K 31/519* | (2006.01) | |
| *C07D 417/02* | (2006.01) | |
| *C07D 495/04* | (2006.01) | |
| *C07D 498/08* | (2006.01) | |

(52) U.S. Cl.
CPC ............ *C07D 495/04* (2013.01); *A61K 31/519* (2013.01); *A61K 31/5377* (2013.01); *A61K 31/5386* (2013.01); *C07D 417/02* (2013.01); *C07D 498/08* (2013.01)

(58) Field of Classification Search
CPC ............ A61K 31/519; A61K 31/5377; A61K 31/5386; C07D 495/04; C07D 417/02; C07D 498/08
See application file for complete search history.

(56) References Cited

U.S. PATENT DOCUMENTS

| 8,163,763 | B2 | 4/2012 | Bergeron et al. |
| 8,785,457 | B2 | 7/2014 | Lynch et al. |
| 2004/0191836 | A1 | 9/2004 | Abraham |
| 2013/0196982 | A1 | 8/2013 | Lynch et al. |
| 2014/0163023 | A1 | 6/2014 | Lynch et al. |
| 2014/0296234 | A1 | 10/2014 | Lynch et al. |
| 2014/0378438 | A1 | 12/2014 | Lynch et al. |

FOREIGN PATENT DOCUMENTS

| EP | 1 054 004 A1 | 11/2000 |
| WO | WO 98/35985 A1 | 8/1998 |
| WO | WO 99/02166 A1 | 1/1999 |
| WO | WO 00/47212 A1 | 8/2000 |
| WO | WO 01/32651 A1 | 5/2001 |
| WO | WO 01/60814 A2 | 8/2001 |
| WO | WO 2006/117560 A1 | 11/2006 |

(Continued)

OTHER PUBLICATIONS

International Search Report, which was completed on Nov. 9, 2012 in International Application No. PCT/EP2012/069676.
Folkes, et al., "The identification of 2-81H-Indazol-4-yl)-6-(4-methanesulfonyl-p iperazin-1-ylmethyl)-4-morpholin-4-yl-thieno[3,2-d]pyrimidine (GDC-0941) as a potent, selective, orally bioavailable inhibitor of Class I PI3 Kinase for the treatment of cancer", Journal of Medicinal Chemistry, 51:5522-5532, 2008.
Verheijen, et al., "Discovery of 2-arylthieno[3,2-d]pyrimidines containing 8-oxa-3-azabi-cyclo[3.2.1]octane in the 4-position as potent inhibitors of mTOR with selectivity over PI3K", Bioorganic & Medicinal Chemistry Letters, 20(1):375-379, 2010.
Anari, et al., "Bridging cheminformatic metabolite prediction and tanden mass spectrometry", *DDT*, vol. 10, pp. 711-717 (2005).

(Continued)

*Primary Examiner* — Rebecca Anderson
(74) *Attorney, Agent, or Firm* — Margaret M. Tomaska; Edward R. Gimmi

(57) ABSTRACT

The invention relates to compounds of formula (I)

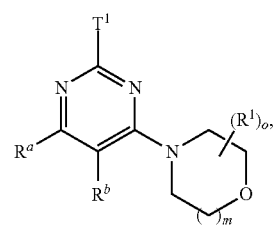

(I)

wherein m, o, $R^a$, $R^b$, $R^1$ and $T^1$ have the meaning as cited in the description and the claims. The compounds are useful as inhibitors of mTOR for the treatment or prophylaxis of mTOR related diseases and disorders. The invention also relates to pharmaceutical compositions including the compounds, the preparation of the compounds as well as their use as medicaments.

15 Claims, No Drawings

(56) References Cited

FOREIGN PATENT DOCUMENTS

| WO | WO 2006/134056 A1 | 12/2006 |
|---|---|---|
| WO | WO 2008/015013 A1 | 2/2008 |
| WO | WO 2008/023159 A1 | 2/2008 |
| WO | WO 2008/115974 A2 | 9/2008 |
| WO | WO 2008/116129 A2 | 9/2008 |
| WO | WO 2008/129380 A1 | 10/2008 |
| WO | WO 2009/007748 A2 | 1/2009 |
| WO | WO 2009/007749 A2 | 1/2009 |
| WO | WO 2009/007750 A1 | 1/2009 |
| WO | WO 2009/007751 A2 | 1/2009 |
| WO | WO 2009/008992 A2 | 1/2009 |
| WO | WO 2009/049242 A1 | 4/2009 |
| WO | WO 2009/098021 A1 | 8/2009 |
| WO | WO 2010/014939 A1 | 2/2010 |
| WO | WO 2010/052569 A2 | 5/2010 |
| WO | WO 2010/052569 A2 | 5/2010 |
| WO | WO 2010/103094 A1 | 9/2010 |
| WO | WO 2010/103094 A1 | 9/2010 |
| WO | WO 2010/120994 A2 | 10/2010 |
| WO | WO 2010/120998 A1 | 10/2010 |
| WO | WO 2011/011716 A1 | 1/2011 |
| WO | WO 2011/107585 A1 | 9/2011 |
| WO | WO 2012/0136622 A1 | 10/2012 |
| WO | WO 2013/041652 A1 | 3/2013 |

OTHER PUBLICATIONS

Asakura, et al., "Recent advances in basic and clinical aspects of inflammatory bowel disease: Which steps in the mucosal inflammation should we block for the treatment of inflammatory bowel disease?", *World Journal of Gastroenterology*, vol. 13, No. 15, pp. 2145-2149 (2007).

Bantscheff, et al., "Quantitative chemical proteomics reveals mechanisms of action of clinical ABL kinase inhibitors", *Nat Biotechnol.*, vol. 25, No. 9, pp. 1035-1044 (2007).

Berger, et al., "Rapamycin alleviates toxity of different aggregate-prone proteins", *Human Molecular Genetics*, vol. 15, No. 3, pp. 433-442 (2006).

Custer, et al., "The Role of Genetic Toxicology in Drug Discovery and Optimization", *Current Drug Metabolosim*, vol. 9, pp. 978-985 (2008).

D'Cruz, et al., "Systemic lupus erythematosus", *Lancet*, vol. 369, pp. 587-596 (2007).

Faivre, et al., "Current development of mTOR inhibitors as anticancer agents", *Nat. Rev. Drug. Disc.*, vol. 5, pp. 671-688 (2006).

Feldman, et al. "Active-Site Inhibitors of mTOR Target Rapamycin-Resistant Outputs of mTORC1 and mTORC2", *PLOS Biology*, vol. 7, Issue 2, pp. 1-13 (2009).

Firestein, Gary S., "Evolving concepts of rheumatoid arthritis", *Nature*, vol. 423, pp. 356-361 (2003).

Folkes, et al., "The identification of 2-81H-Indazol-4-yl)-6-(4-methanesulfonyl-p iperazin-l-ylmethyl)-4- morpholin-4-yl-thieno[3,2-d]pyrimidine (GDC-0941) as a potent, selective, orally bioavailable inhibitor of Class I PI3 Kinase for the treatment of cancer", *Journal of Medicinal Chemistry*, vol. 51, pp. 5522-5532 (2008).

Fura, A., "Role of pharmacologically active metabolites in drug discovery and development", *DDT*, vol. 11, pp. 133-142 (2006).

Garcia-Echeverria, et al., "Drug discovery approaches targeting the PI3KfAkt pathway in cancer", *Oncogene*, vol. 27, pp. 5511-5526 (2008).

Hanahan, et al., "The Hallmarks of Cancer", Cell, vol. 100, pp. 57-70 (2000).

Hemmer, et al., "New Concepts in the Immunopathogenesis Of Multiple Sclerosis", *Nature Reviews, Neuroscience*, vol. 3, pp. 291-301 (2002).

Kersey, et al., "The International Protein Index: an integrated database for proteomics", *Proteomics*, vol. 4, No. 7, pp. 1985-1988 (2004).

Knight, ZA, et al., "Isoform-specific phosphoninositide 3-kinase inhibitors from an arylmorpholine scaffold", *Bioorganic & Medicinal Chemistry*, vol. 12, pp. 4749-4759 (2004).

Manning, et al., "The protein kinase complement of the human genome",*Science*, vol. 298, No. 5600, pp. 1912-1934 (2002).

Mizushima, et al., "Autophagy fights disease through cellular self-digestion", *Nature*, vol. 451, No. 7182, pp. 1069-1075 (2008).

Moorman, et al., "Rapamycin-resistant mTORC1 kinase activity is required for herpes virus replication", J. Virol., vol. 84, No. 10, pp. 5260-69 (2010).

Mortelmans, et al., "The Ames Salmonella/microsome mutagenicity assay", *Mutation Research*, vol. 455, pp. 29-60 (2000).

Nedderman, A. N. R., "Metabolites in Safety Testing: Metabolite Identification Strategies in Discovery and Development", *Biopharm. Drug Dispos.*, vol. 30, pp. 153-162 (2009).

Pan, et al., "Neuroprotection of rapamycin in lactacystin-induced neurodegeneration via autophagy enhancement", *Neurobiology of Disease*, vol. 32, pp. 16-25 (2008).

Podlipnik, et al., "DFG-in and DFG-out homology models of TrkB kinase receptor: Induced-fit and ensemble docking", *Journal of Molecular Graphics and Modelling*, vol. 29, pp. 309-320 (2010).

Ravikumar, et al., "Inhibition of mTOR induces autophagy and reduces toxicity of polyglutamine expansions in fly and mouse models of Huntington disease," Nature Genetics, vol. 36, No. 6, pp. 585-95 (2004).

Richard, et al., "Recent advances in the development of selective, ATP-competitive inhibitors of mTOR", *Current Opinion Drug Discovery & Development*, vol. 13, No. 4, pp. 428-440 (2011).

Rosner, et al., "The mTOR pathway and its role in human genetic diseases", *Mutation Research*, vol. 659, pp. 284-292 (2008).

Sarbassov, et al., "Prolonged Rapamycin Treatment Inhibits mTORC2 Assembly and AkUPKB", *Molecular Cell*, vol. 22, pp. 159-168 (2006).

Sato, et al., "Single amino-acid changes that confer constitutive activation of mTOR are discovered in human cancer", Oncogene, vol. 29, No. 18, pp. 2746-2752 (2010).

Schmelzle, et al., "TOR, a Central Controller of Cell Growth", Cell, vol. 103, pp. 253-262 (2000).

Schon, et al., "Psoriasis", New England Journal of Medicine, vol. 352, pp. 1899-912 (2005).

Serruys, et al., "Coronary-Artery Stents", *New England Journal of Medicine*, vol. 354, No. 5, pp. 483-95 (2006).

Shah, et al., "Inappropriate Activation of the TSC/Rheb/mTORIS6K Cassette Induces IRS1/2 Depletion, Insulin ReSistance, and Cell Survival Deficiencies", *Current Biology*vol. 14, pp. 1650-1656 (2004).

Thoreen, et al., "An ATP-competitive Mammalian Target of Rapamycin Inhibitor Reveals Rapamycin-resistant Functions of mTORC1", *Journal of Biological Chemistry*, vol. 284, No. 12, pp. 8023-8032 (2009).

Tsang, et al., "Targeting mammalian target of rapamycin (mTOR) for health and diseases", *Drug Discovery Today*, vol. 12, pp. 112-124 (2007).

Verheijen, et al., "Discovery of 2-arylthieno [3,2-d]pyrimidines containing 8-oxa-3-azabi-cyclo[3.2.1]octane in the 4-position as potent inhibitors of mTOR with selectivity over PI3K", *Bioorganic & Medicinal Chemistry Letters*, vol. 20, No. 1, pp. 375-379 (2010).

Xue, et al., "Palomid 529, a Novel Small-Molecule Drug, Is a TORC1ITORC2 Inhibitor That Reduces Tumor Growth, Tumor Angiogenesis, and Vascular Permeability", *Cancer Research*, vol. 68, No. 22, pp. 9551-9557 (2008).

Yeh, et al., "Rapamycin inhibits clonal expansion and adipogenic differentiation of 3T3-L 1 cells", *Proc. Natl. Acad. Sci. USA*, vol. 92, Biochemistry, pp. 11086-11090 (1995).

MORPHOLINO SUBSTITUTED BICYCLIC PYRIMIDINE UREA OR CARBAMATE DERIVATIVES AS MTOR INHIBITORS

This application is a 371 of International Application No. PCT/EP2012/069676, filed 05 Oct. 2012, which is incorporated herein by reference. This application claims benefit of the earlier filing date of EP Application No. 11184358.7, filed 07 Oct, 2011, and U.S. Provisional Application No. 61/649,995 filed 22 May 2012.

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate kinase activity, in particular mTOR activity, and signal transduction pathways relating to cellular activities as mentioned above. Furthermore, the present invention relates to pharmaceutical compositions comprising said compounds, e.g. for the treatment of diseases such as immunological, inflammatory, autoimmune, allergic disorders, or proliferative diseases such as cancer.

Kinases catalyse the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Inappropriately high protein kinase activity is involved in many diseases including cancer, metabolic diseases and autoimmune/inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

mTOR ("mammalian target of rapamycin", also known as FRAP or RAFT1) has become a recent focus of drug discovery efforts (Tsang et al., 2007, Drug Discovery Today 12, 112-124). It was discovered that the mTOR protein is the drug target for the immunosuppressive effect of rapamycin, a drug that is used to prevent transplant rejection. Rapamycin works through a gain-of-function mechanism by binding to the intracellular protein "FK-506-binding protein of 12 kDA" (FKBP12) to generate a drug-receptor complex that then binds to and inhibits mTOR. Thus, rapamycin induces the formation of the ternary complex consisting of rapamycin and the two proteins FKBP12 and mTOR.

The mTOR protein is a large kinase of 289 kDA which occurs in all eukaryotic organisms sequenced so far (Schmelzle and Hall, 2000, Cell 103, 253-262). The sequence of the carboxy-terminal "phosphatidylinositol 3-kinase (PI3K)-related kinase" (PIKK) domain is highly conserved between species and exhibits serine and threonine kinase activity but no detectable lipid kinase activity. The intact PIKK domain is required for all known functions of mTOR. The FKBP12-rapamycin-binding (FRB) domain is located close to the PIKK domain and forms a hydrophobic pocket that binds to the rapamycin bound to FKBP12. The FRB domain does not appear to inhibit the enzymatic activity of the kinase domain directly. One explanation is that FKBP12-rapamycin prevents the interaction of mTOR with its substrates due to steric hindrance. The N-terminus of mTOR consists of approximately 20 tandem repeats of 37 to 43 amino acids termed HEAT repeats. The HEAT repeats interact with protein binding partners such as Raptor.

mTOR can form at least two distinct proteins complexes, mTORC1 and mTORC2. In the mTORC1 protein complex mTOR interacts with the proteins Raptor and mLST8/GβL and regulates cell growth by phosphorylating effectors such as p70S6K and 4E-BP1 to promote mRNA translation and protein synthesis. The mTORC1 complex is responsible for sensing nutrient signals (for example the availability of amino acids) in conjunction with insulin signaling. The activity of mTOR in mTORC1 can be inhibited by rapamycin.

The second protein complex, mTORC2, consists of the proteins mTOR, Rictor, mLST8/GβL and Sin1 and is involved in the organization of actin. The mTORC2 was originally described as rapamycin insensitive. A recent publication demonstrated that rapamycin affects the function of mTORC2 after prolonged treatment through an indirect mechanism by interfering with the assembly of the mTORC2 protein complex (Sarbassov et al., 2006, Molecular Cell 22, 159-168).

The biological function of mTOR is that of a central regulator of various extracellular and intracellular signals, including growth factors, nutrients, energy and stress. Growth factor and hormone (e.g. insulin) induced mTOR activation is mediated by PI3 kinases, Akt, and the tuberous sclerosis protein complex (TSC). For example, mTOR acts as a central regulator of cell proliferation, angiogenesis, and cell metabolism (Tsang et al., 2007, Drug Discovery Today 12, 112-124). In addition to its immunosuppressive effects rapamycin (Sirolimus) is a potent inhibitor of the proliferation of vascular smooth muscle cells and was approved by the FDA as an anti-restenosis drug used in coronary stents. In addition, it was observed that rapamycin displays anti-tumour activity in several in vitro and animal models (Faivre et al., 2006. Nat. Rev. Drug. Discov. 5(8):671-688).

Because of the therapeutic potential of rapamycin several pharmaceutical companies started to develop rapamycin analogs to improve the pharmacokinetic properties of the molecule (Tsang et al., 2007, Drug Discovery Today 12, 112-124). For example, CCI-779 (temsirolimus) represents a more water-soluble ester derivative of rapamycin for intravenous and oral formulation. CCI-779 has antitumor activity either alone or in combination with cytotoxic agents in cell lines. RAD-001 (everolimus) is a hydroxyethyl ether derivative of rapamycin that is developed for oral administration. AP23573 (deferolimus) is developed for either oral or intravenous administration.

In general, the rapamycin derivatives act through the same molecular mechanism, the induction of the ternary rapamycin-FKBP12-mTOR complex. It is conceivable that the function of mTOR could be equally or even more effectively inhibited by inhibitors of the kinase function. For example, this could be achieved by identifying compounds that interact with the ATP-binding pocket of the mTOR kinase domain. For example Torin1 is a potent and selective ATP-competitive mTOR inhibitor that directly binds to both mTOR complexes and impairs cell growth and proliferation more efficiently than rapamycin (Thoreen et al., 2009. J Biol. Chem. 284(12): 8023-32; Feldman et al., 2009. PLOSBiology 7(2):e38).

Diseases and disorders associated with mTOR are further described, e.g. in WO-A 2008/116129, WO-A 2008/115974, WO-A 2008/023159, WO-A 2009/007748, WO-A 2009/007749, WO-A 2009/007750, WO-A 2009/007751, WO-A 2011/011716.

Several mTOR inhibitors have been reported in the literature which may be useful in the medical field, for example as anticancer agents (Faivre et al., 2006. Nat. Rev. Drug. Discov. 5(8):671-688). In WO-A 2008/116129 imidazolopyrimidine analogs are described as mixed mTOR and PI3K kinase inhibitors. Pyrazolopyrimidine analogs are described as mixed mTOR and PI3K kinase inhibitors in WO-A 2008/115974. Further pyrimidine derivatives as mTOR kinase and/or PI3K enzyme active compounds are disclosed in WO-A 2008/023159, WO-A 2009/007748, WO-A 2009/007749, WO-A 2009/007750, WO-A 2009/007751, WO-A 2010/103094, WO-A 2010/120994 and WO-A 2010/120998.

Triazine compounds as PI3K kinase and MTOR inhibitors are described in WO 2009/143313 A1, WO 2009/143317 A1 and WO 2010/096619 A1.

Furthermore mTOR inhibitors are described in international patent applications with application numbers PCT/EP2012/055953 and PCT/EP2012/068590 as well as in WO2011/107585 A1.

Unsubstituted conformationally-restricted cyclic sulfones have been described as potent and selective mTOR kinase inhibitors in Bioorganic and Medicinal Chemistry Letters, 2012, 22 (15), 5114-5117.

It is expected that a selective mTOR inhibitor that inhibits mTOR with greater potency than other kinases may have advantageous therapeutic properties because inhibition of other kinases may cause unwanted side effects (Richard et al., 2011. Current Opinion Drug Discovery and Development 13(4):428-440). Especially selectivity versus members of the phosphatidylinositol 3 kinase (PI3K) family (for example PI3Kα, PI3Kβ, PI3Kγ, and PI3Kδ) and PI3K related kinases (for example DMA-PK, ATM and ATR) may be important.

Even though mTOR inhibitors are known in the art there is a need for providing additional mTOR inhibitors having at least partially more effective pharmaceutically relevant properties, like activity, selectivity, and ADME properties.

Accordingly, the present invention provides compounds of formula (I)

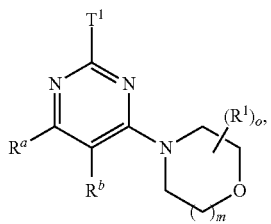

(I)

or a pharmaceutically acceptable salt thereof, wherein
m is 1; or 2;
o is 1; 2; 3; or 4;
Each $R^1$ is independently selected from the group consisting of H; halogen; CN; C(O)OR$^2$; OR$^{2a}$; oxo (=O); C(O)R$^2$; C(O)N(R$^2$R$^{2a}$); S(O)$_2$N(R$^2$R$^{2a}$); S(O)N(R$^2$R$^{2a}$); S(O)$_2$R$^2$; S(O)R$^2$; N(R$^2$)S(O)$_2$N(R$^{2a}$R$^{2b}$); N(R$^2$)S(O)N(R$^{2a}$R$^{2b}$); SR$^2$; N(R$^2$R$^{2a}$); NO$_2$; OC(O)R$^2$; N(R$^2$)C(O)R$^{2a}$; N(R$^2$)S(O)$_2$R$^{2a}$; N(R$^2$)S(O)R$^{2a}$; N(R$^2$)C(O)N(R$^{2a}$R$^{2b}$); N(R$^2$)C(O)OR$^{2a}$; OC(O)N(R$^2$R$^{2a}$); and C$_{1-6}$alkyl, wherein C$_{1-6}$alkyl is optionally substituted with one or more R$^3$, which are the same or different;
Optionally two $R^1$ are joined to form together with the ring to which they are attached an 8 to 11 membered heterobicycle;

$R^2$, $R^{2a}$, $R^{2b}$ are independently selected from the group consisting of H; C$_{1-6}$alkyl, wherein C$_{1-6}$ alkyl is optionally substituted with one or more halogen, which are the same or different;
$R^3$ is halogen; CN; C(O)OR$^4$; OR$^4$; C(O)R$^4$; C(O)N(R$^4$R$^{4a}$); S(O)$_2$N(R$^4$R$^{4a}$); S(O)N(R$^4$R$^{4a}$); S(O)$_2$R$^4$; S(O)R$^4$; N(R$^4$)S(O)$_2$N(R$^{4a}$R$^{4b}$); N(R$^4$)S(O)N(R$^{4a}$R$^{4b}$); SR$^4$; N(R$^4$R$^{4a}$); NO$_2$; OC(O)R$^4$; N(R$^4$)C(O)R$^{4a}$; N(R$^4$)S(O)$_2$R$^{4a}$; N(R$^4$)S(O)R$^{4a}$; N(R$^4$)C(O)N(R$^{4a}$R$^{4b}$); N(R$^4$)C(O)OR$^{4a}$; or OC(O)N(R$^4$R$^{4a}$);
$R^4$, $R^{4a}$, $R^{4b}$ are independently selected from the group consisting of H; and C$_{1-6}$alkyl, wherein C$_{1-6}$alkyl is optionally substituted with one or more halogen, which are the same or different;
$T^1$ is phenyl; or 5 to 6 membered aromatic heterocycle, wherein $T^1$ is substituted with N(R$^{5a}$)C(O)N(R$^{5b}$R$^5$) or N(R$^{5a}$)C(O)OR$^5$ and optionally further substituted with one or more R$^6$, which are the same or different;
$R^6$ is halogen; CN; C(O)OR$^7$; OR$^7$; C(O)R$^7$; C(O)N(R$^7$R$^{7a}$); S(O)$_2$N(R$^7$R$^{7a}$); S(O)N(R$^7$R$^{7a}$); S(O)$_2$R$^7$; S(O)R$^7$; N(R$^7$)S(O)$_2$N(R$^{7a}$R$^{7b}$); N(R$^7$)S(O)N(R$^{7a}$R$^{7b}$); SR$^7$; N(R$^7$R$^{7a}$); NO$_2$; OC(O)R$^7$; N(R$^7$)C(O)R$^{7a}$; N(R$^7$)S(O)$_2$R$^{7a}$; N(R$^7$)S(O)R$^{7a}$; N(R$^7$)C(O)N(R$^{7a}$R$^{7b}$); N(R$^7$)C(O)OR$^{7a}$; OC(O)N(R$^7$R$^{7a}$); or C$_{1-6}$alkyl, wherein C$_{1-6}$alkyl is optionally substituted with one or more halogen, which are the same or different;
$R^{5a}$, $R^{5b}$, $R^7$, $R^{7a}$, $R^{7b}$ are independently selected from the group consisting of H; C$_{1-6}$alkyl, wherein C$_{1-6}$alkyl is optionally substituted with one or more halogen, which are the same or different;
$R^5$ is H; $T^2$; and C$_{1-6}$alkyl, wherein C$_{1-6}$alkyl is optionally substituted with one or more R$^s$, which are the same or different;
$R^8$ is halogen; CN; C(O)OR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); N(R$^9$)S(O)N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)N(R$^{9a}$R$^{9b}$); N(R$^9$)C(O)OR$^{9a}$; OC(O)N(R$^9$R$^{9a}$); or $T^2$;
$R^9$, $R^{9a}$, $R^{9b}$ are independently selected from the group consisting of H; and C$_{1-6}$alkyl, wherein C$_{1-6}$alkyl is optionally substituted with one or more halogen, which are the same or different;
Optionally $R^5$, $R^{5b}$ are joined to form together with the nitrogen atom to which they are attached an at least the nitrogen atom as ring heteroatom containing 4 to 7 membered heterocyclyl ring; or 8 to 11 membered heterobicyclyl ring, wherein the 4 to 7 membered heterocyclyl ring; and the 8 to 11 membered heterobicyclyl ring are optionally substituted with one or more R$^{10}$, which are the same or different;
$T^2$ is C$_{3-7}$cycloalkyl; 4 to 7 membered heterocyclyl; 4 to 7 membered heteroaryl; 8 to 11 membered heterobicyclyl; phenyl; naphthyl; indenyl; or indanyl, wherein $T^2$ is optionally substituted with one or more R$^{10}$, which are the same or different;
$R^{10}$ is halogen; CN; C(O)OR$^{11}$; OR$^{11}$; oxo (=O), where the ring is at least partially saturated; C(O)R$^{11}$; C(O)N(R$^{11}$R$^{11a}$); S(O)$_2$N(R$^{11}$R$^{11a}$); S(O)N(R$^{11}$R$^{11a}$); S(O)$_2$R$^{11}$; S(O)R$^{11}$; N(R$^{11}$)S(O)$_2$N(R$^{11a}$R$^{11b}$); N(R$^{11}$)S(O)N(R$^{11a}$R$^{11b}$); SR$^{11}$; N(R$^{11}$R$^{11a}$); NO$_2$; OC(O)R$^{11}$; N(R$^{11}$)C(O)R$^{11a}$; N(R$^{11}$)S(O)$_2$R$^{11a}$; N(R$^{11}$)S(O)R$^{11a}$; N(R$^{11}$)C(O)N(R$^{11a}$R$^{11b}$); N(R$^{11}$)C(O)OR$^{11a}$; OC(O)N(R$^{11}$R$^{11a}$); or C$_{1-6}$alkyl, wherein C$_{1-6}$ alkyl is optionally substituted with one or more R$^{12}$, which are the same or different;

$R^{11}$, $R^{11a}$, $R^{11b}$ are independently selected from the group consisting of H; $C_{1-6}$alkyl, wherein $C_{1-6}$alkyl is optionally substituted with one or more halogen, which are the same or different;

$R^{12}$ is halogen; CN; $C(O)OR^{13}$; $OR^{13}$; $C(O)R^{13}$; $C(O)N(R^{13}R^{13a})$; $S(O)_2N(R^{13}R^{13a})$; $S(O)N(R^{13}R^{13a})$; $S(O)_2R^{13}$; $S(O)R^{13}$; $N(R^{13})S(O)_2N(R^{13a}R^{13b})$; $N(R^{13})S(O)N(R^{13a}R^{13b})$; $SR^{13}$; $N(R^{13}R^{13a})$; $NO_2$; $OC(O)R^{13}$; $N(R^{13})C(O)R^{13a}$; $N(R^{13})S(O)_2R^{13a}$; $N(R^{13})S(O)R^{13a}$; $N(R^{13})C(O)N(R^{13a}R^{13b})$; $N(R^{13})C(O)OR^{13a}$; or $OC(O)N(R^{13}R^{13a})$;

$R^{13}$, $R^{13a}$, $R^{13b}$ are independently selected from the group consisting of H; and $C_{1-6}$alkyl, wherein $C_{1-6}$alkyl is optionally substituted with one or more halogen, which are the same or different;

$R^a$, $R^b$ are joined to form $-(CR^{14}R^{14a})_p-S(O)_r-(CR^{14b}R^{14c})_q-$;

r is 0; 1; or 2;

p, q are 0; 1; 2; or 3, provided that p+q is 2; 3; or 4;

$R^{14}$, $R^{14a}$, $R^{14b}$, $R^{14c}$ are independently selected from the group consisting of H; halogen; CN; $C(O)OR^{15}$; $OR^{15}$; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $N(R^{15})S(O)N(R^{15a}R^{15b})$; $SR^{15}$; $N(R^{15}R^{15a})$; $NO_2$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$; $N(R^{15})C(O)OR^{15a}$; $OC(O)N(R^{15}R^{15a})$; or $C_{1-6}$alkyl, wherein $C_{1-6}$alkyl is optionally substituted with one or more $R^{16}$, which are the same or different;

Optionally one of the pairs $R^{14}$, $R^{14a}$ and $R^{14b}$, $R^{14c}$ or both pairs form an oxo group (=O);

Optionally one of the pairs selected from the group consisting of $R^{14}$, $R^{14a}$; $R^{14}$, $R^{14b}$; two adjacent $R^{14}$, in case p>1; and two adjacent $R^{14b}$, in case q>1, are joined to form together with the ring to which they are attached an 6 to 11 membered heterobicycle;

$R^{15}$, $R^{15a}$, $R^{15b}$ are independently selected from the group consisting of H; $C_{1-6}$ alkyl, wherein $C_{1-6}$ alkyl is optionally substituted with one or more halogen, which are the same or different;

$R^{16}$ is halogen; CN; $C(O)OR^{17}$; $OR^{17}$; $C(O)R^{17}$; $C(O)N(R^{17}R^{17a})$; $S(O)_2N(R^{17}R^{17a})$; $S(O)N(R^{17}R^{17a})$; $S(O)_2R^{17}$; $S(O)R^{17}$; $N(R^{17})S(O)_2N(R^{17a}R^{17b})$; $N(R^{17})S(O)N(R^{17a}R^{17b})$; $SR^{17}$; $N(R^{17}R^{17a})$; $NO_2$; $OC(O)R^{17}$; $N(R^{17})C(O)R^{17a}$; $N(R^{17})S(O)_2R^{7a}$; $N(R^{17})S(O)R^{17a}$; $N(R^{17})C(O)N(R^{17a}R^{17b})$; $N(R^{17})C(O)OR^{17a}$; or $OC(O)N(R^{17}R^{17a})$;

$R^{17}$, $R^{17a}$, $R^{17b}$ are independently selected from the group consisting of H; $C_{1-6}$alkyl, wherein $C_{1-6}$alkyl is optionally substituted with one or more halogen, which are the same or different.

In case a variable or substituent can be selected from a group of different variants and such variable or substituent occurs more than once the respective variants can be the same or different.

Within the meaning of the present invention the terms are used as follows:

The term "optionally substituted" means unsubstituted or substituted. Generally—but not limited to—, "one or more substituents" means one, two or three, preferably one or two and more preferably one substituents. Generally these substituents can be the same or different.

"Alkyl" means a straight-chain or branched carbon chain. Each hydrogen of an alkyl carbon may be replaced by a substituent as further specified herein.

"$C_{1-4}$alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. $-CH_2-$, $-CH_2-CH_2-$, $-CH(CH_3)-$, $-C(CH_2)-$, $-CH_2-CH_2-CH_2-$, $-CH(C_2H_5)-$, $-C(CH_3)_2-$, when two moieties of a molecule are linked by the alkyl group. Each hydrogen of a $C_{1-4}$alkyl carbon may be replaced by a substituent as further specified herein.

"$C_{1-6}$alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. $-CH_2-$, $-CH_2-CH_2-$, $-CH(CH_3)-$, $-CH_2-CH_2-CH_2-$, $-CH(C_2H_5)-$, $-C(CH_3)_2-$, when two moieties of a molecule are linked by the alkyl group. Each hydrogen of a $C_{1-6}$ alkyl carbon may be replaced by a substituent as further specified herein.

"$C_{3-7}$cycloalkyl" or "$C_{3-7}$cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent as further specified herein.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or unsaturated) wherein at least one ring atom up to 4 ring atoms are replaced by a heteroatom selected from the group consisting of sulfur (including $-S(O)-$, $-S(O)_2-$), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly.

"6 to 11 membered heterobicyclyl" or "6 to 11 membered heterobicycle" means a heterocyclic system of two rings with 6 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms (preferably up to 5, more preferably up to 4, more preferably up to 3 ring atoms) are replaced by a heteroatom selected from the group consisting of sulfur (including $-S(O)-$, $-S(O)_2-$), oxygen and nitrogen (including =N(O)—) and wherein the ring is linked to the rest of the molecule via a carbon or nitrogen atom. Examples for a 6 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquino line, tetrahydroisoquinoline, dihydroisoquinoline, benzazepine, purine or pteridine. The term 6 to 11 membered heterobicycle also includes spiro structures of two rings like 1,4-dioxa-8-azaspiro[4.5]decane or bridged heterocycles like 8-aza-bicyclo[3.2.1]octane. The term "8 to 11 membered heterobicyclyl" or "8 to 11 membered heterobicycle" is defined accordingly.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)₂—), oxygen and nitrogen (including =N(O)—). Examples for such heterocycles are furan, thiophene, pyrrole, imidazole, pyrazole, oxazole, isoxazole, thiazole, isothiazole, thiadiazole, pyranium, pyridine, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, in formula (I) R$^a$ and R$^b$ are selected to give one of formulae (Ia) to (Ij):

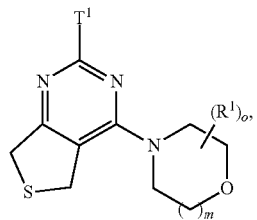
(Ia)

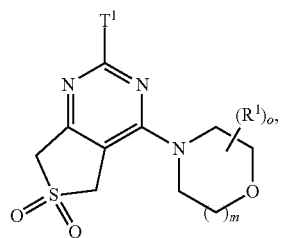
(Ib)

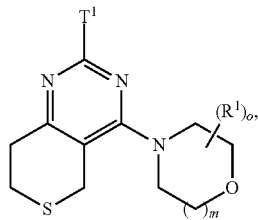
(Ic)

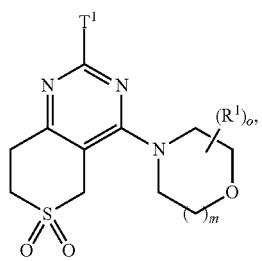
(Id)

-continued

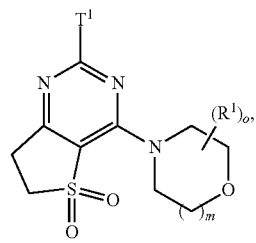
(Ie)

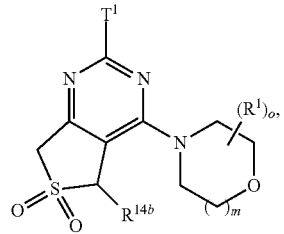
(If)

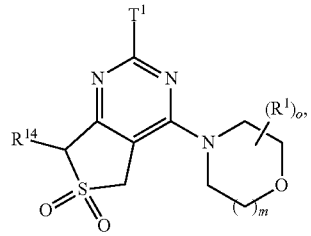
(Ig)

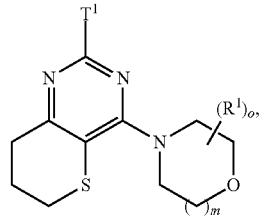
(Ih)

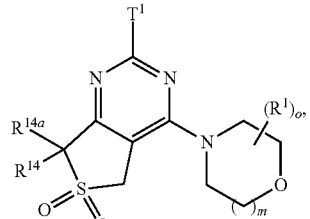
(Ii)

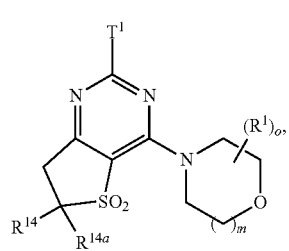
(Ij)

wherein T$^1$, R$^1$, o, m, R$^{14}$, R$^{14a}$, R$^{14b}$ have the meaning as indicated above. More preferred are (Ib), (If) and (Ii), especially (Ii).

Preferably, in formula (I) R$^a$ and R$^b$ are selected to give one of formulae (Ik) to (Ip):

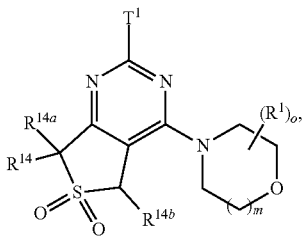
(Ik)

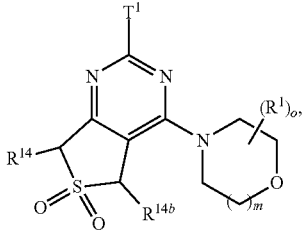
(Il)

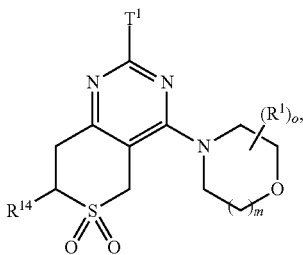
(Im)

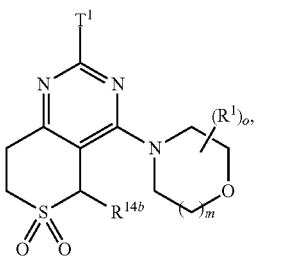
(In)

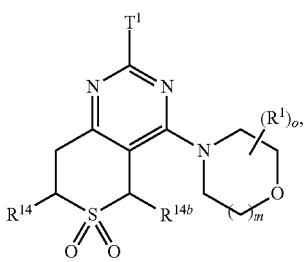
(Io)

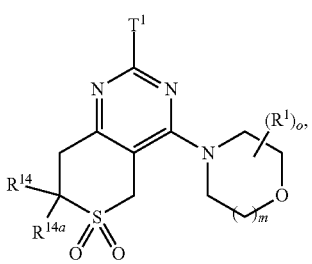
(Ip)

wherein $T^1$, $R^1$, o, m, $R^{14}$, $R^{14a}$, $R^{14b}$ have the meaning as indicated above. Most preferred is (Ik).

Preferably, $T^1$ is phenyl, wherein $T^1$ is substituted with $N(R^{5a})C(O)N(R^{5b}R^5)$ or $N(R^{5a})C(O)OR^5$ and optionally further substituted with one or more $R^6$, which are the same or different.

Preferably, $T^1$ is substituted with $N(R^{5a})C(O)N(R^{5b}R^5)$ and optionally further substituted with one or more $R^6$, which are the same or different.

Preferably, $T^1$ is not further substituted with one or more $R^6$.

Preferably, in formula (I) $T^1$ is defined to give formula (Ik)

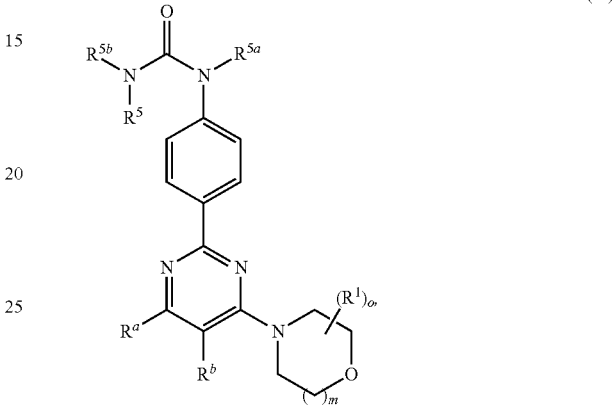
(Ik)

wherein o, m, $R^1$, $R^a$, $R^b$, $R^5$, $R^{5a}$, $R^{5b}$ have the meaning as indicated above.

Preferably, $R^{5a}$, $R^{5b}$ are H.

Preferably, $R^5$ is $T^2$, wherein $T^2$ is unsubstituted or substituted with one or more $R^{10}$, which are the same or different and wherein $T^2$ is phenyl; pyridyl; cyclopropyl; cyclobutyl; cyclopentyl; cyclohexyl; oxetanyl; or tetrahydrofuranyl. More preferably, $T^2$ is cyclopropyl. More preferably, $T^2$ is unsubstituted.

Preferably, $R^5$ is unsubstituted $C_{1-6}$ alkyl.

Preferably, $R^5$ is $C_{1-6}$ alkyl substituted with one or more $R^8$, which are the same or different and selected from the group consisting of F; $OR^9$; and $N(R^9R^{9a})$.

Preferably, r is 0; or 2. Preferably, r is 1; or 2. Even more preferably, r is 2.

Preferably, p, q are 1; 2; or 3. Thus, preferably neither p nor q are 0.

Preferably, p+q is 2; or 3.

More preferably p and q are both 1.

Even more preferably p and q are both 1 and r is 2.

Preferably, at most two of $R^{14}$, $R^{14a}$, $R^{14b}$, $R^{14c}$ are other than H. Accordingly, in one embodiment none of $R^{14}$, $R^{14a}$, $R^{14b}$, $R^{14c}$ is other than H; in another embodiment one of $R^{14}$, $R^{14a}$, $R^{14b}$, $R^{14c}$ is other than H; and in a third embodiment two of $R^{14}$, $R^{14a}$, $R^{14b}$, $R^{14c}$ are other than H. Preferably, at least one of $R^{14}$, $R^{14a}$, $R^{14b}$ and $R^{14c}$ is other than H.

Preferably, three of $R^{14}$, $R^{14a}$, $R^{14b}$, $R^{14c}$ are other than H.

Preferably, $R^{14}$, $R^{14a}$, $R^{14b}$, $R^{14c}$ are independently selected from the group consisting of H; F; ethyl; and methyl. More preferably, $R^{14}$, $R^{14a}$, $R^{14b}$, $R^{14c}$ are independently selected from the group consisting of H; and methyl. In one embodiment $R^{14}$ is methyl, $R^{14a}$ is hydrogen, $R^{14b}$ is hydrogen and $R^{14c}$ is hydrogen. In another embodiment $R^{14}$ is methyl, $R^{14a}$ is methyl, $R^{14b}$ is hydrogen and $R^{14c}$ is hydrogen. In another embodiment $R^{14}$ is methyl, $R^{14a}$ is methyl, $R^{14b}$ is methyl and $R^{14c}$ is hydrogen. In another embodiment $R^{14}$ is methyl, $R^{14a}$ is F, $R^{14b}$ is hydrogen and $R^{14c}$ is hydrogen. In another embodiment $R^{14}$ is methyl, $R^{14a}$ is F, $R^{14b}$ is methyl and $R^{14c}$ is hydrogen. In another embodiment $R^{14}$ is methyl, $R^{14a}$ is methyl, $R^{14b}$ is F and $R^{14c}$ is hydrogen. In another embodiment $R^{14}$ is F, $R^{14a}$ is F, $R^{14b}$ is hydrogen and $R^{14c}$ is hydrogen.

Preferably, m is 1.

Preferably, o is 1 or 2.

Preferably, each $R^1$ is independently selected from the group consisting of H; halogen; CN; oxo (=O) or $C_{1-6}$alkyl, wherein $C_{1-6}$alkyl is optionally substituted with one or more $R^3$, which are the same or different.

Preferably, $R^1$ is unsubstituted $C_{1-6}$alkyl (more preferably methyl or ethyl, even more preferred methyl); or $C_{1-6}$alkyl substituted with one $R^3$.

Preferably, two $R^1$ are joined to form together with the ring to which they are attached an 8-oxa-3-azabicyclo[3.2.1]octan-3-yl or an 3-oxa-8-azabicyclo[3.2.1]octan-8-yl ring.

One subclass of compounds according to the present invention is represented by the compounds of formula (Iq):

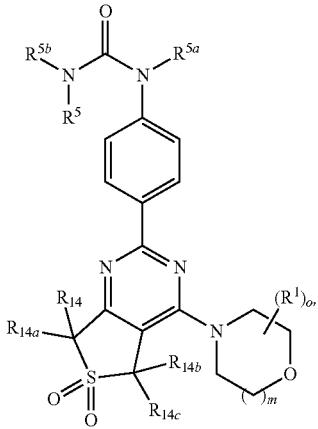

(Iq)

wherein $R^5$, $R^{5a}$, $R^{5b}$, $R^{14}$, $R^{14a}$, $R^{14b}$, $R^{14c}$, $R^1$, o, m are defined as herein.

In one embodiment $R^{5b}$ and $R^{5a}$ are H and $R^5$ is $C_{1-6}$alkyl, or $C_{3-7}$cycloalkyl, wherein $C_{1-6}$ alkyl is optionally substituted with one or more $R^8$, which are the same or different and $C_{3-7}$cycloalkyl is optionally substituted with one or more $R^{10}$, which are the same or different.

In another embodiment $R^{5b}$ and $R^{5a}$ are H and $R^5$ is $C_{1-6}$alkyl (e.g methyl, ethyl, propyl, or isopropyl) which are optionally substituted with one or more of halogen (e.g. fluoro) or $R^8$ (e.g. $OR^9$), which are the same or different, or $R^5$ is $C_{3-7}$cycloalkyl (e.g. cyclopropyl), which is optionally substituted with one or more halogen (e.g. fluoro) or $R^{10}$ (e.g. OR), which are the same or different.

In another embodiment $R^{5b}$ and $R^{5a}$ are H and $R^5$ is $C_{1-6}$alkyl (e.g methyl, ethyl, propyl, or isopropyl) which is optionally substituted with one or more of halogen (e.g. fluoro) or $R^8$ (e.g. $OR^9$), which is the same or different, or $R^5$ is $C_{3-7}$cycloalkyl (e.g. cyclopropyl), which is optionally substituted with one or more halogen (e.g. fluoro) or $R^{10}$ (e.g. $OR^{11}$), which are the same or different and wherein $R^8$ and $R^{10}$ are H.

In another embodiment $R^{5b}$ and $R^{5a}$ are H and $R^5$ is $C_{1-6}$alkyl (e.g methyl, ethyl or propyl) and is substituted with one or more of fluoro or hydroxy.

Specific examples of $R^5$ include cyclopropyl, methyl, ethyl, fluoroethyl, hydroxyethyl, difluoroethyl, isopropyl, fluoropropyl, pyridinyl and oxetanyl.

In one embodiment $R^1$ is $C_{1-6}$alkyl (e.g. methyl, or ethyl) and o is 1.

In another embodiment $(R^1)_o$ is attached at the 3 position.

In one embodiment $R^{14}$, $R^{14a}$, $R^{14b}$ and $R^{14c}$ are selected from $C_{1-6}$ alkyl or H. In one embodiment $R^{14}$, $R^{14a}$, $R^{14b}$ and $R^{14c}$ are selected from $C_{1-6}$ alkyl; F or H.

In one embodiment three of $R^{14}$, $R^{14a}$, $R^{14b}$ and $R^{14c}$ are other than H.

In another embodiment three of $R^{14}$, $R^{14a}$, $R^{14b}$ and $R^{14c}$ are selected from $C_{1-6}$ alkyl (e.g. methyl, ethyl or propyl). In another embodiment three of $R^{14}$, $R^{14a}$, $R^{14b}$ and $R^{14c}$ are selected from $C_{1-6}$alkyl (e.g. methyl, ethyl or propyl) or F.

In another embodiment three of $R^{14}$, $R^{14a}$, $R^{14b}$ and $R^{14c}$ are selected from methyl. In another embodiment three of $R^{14}$, $R^{14a}$, $R^{14b}$ and $R^{14c}$ are selected from methyl or F.

In a further embodiment $R^{14}$, $R^{14a}$, $R^{14b}$ are methyl and $R^{14c}$ is H.

Compounds of formula (I) in which some or all of the above-mentioned groups have the preferred meanings are also an object of the present invention.

Further preferred compounds of the present invention are selected from the group consisting of 1-cyclopropyl-3-(4-(4-morpholino-6,6-dioxido-5,7-dihydrothieno[3,4-d]pyrimidin-2-yl)phenyl)urea;

1-cyclopropyl-3-(4-(4-((2S,6R)-2,6-dimethylmorpholino)-6,6-dioxido-5,7-dihydrothieno[3,4-d]pyrimidin-2-yl)phenyl)urea;

(S)-1-cyclopropyl-3-(4-(4-(3-methylmorpholino)-5,7-dihydrothieno[3,4-d]pyrimidin-2-yl)phenyl)urea;

(S)-1-cyclopropyl-3-(4-(4-(3-methylmorpholino)-6,6-dioxido-5,7-dihydrothieno[3,4-d]pyrimidin-2-yl)phenyl)urea;

(S)-1-ethyl-3-(4-(4-(3-methylmorpholino)-6,6-dioxido-5,7-dihydrothieno[3,4-d]pyrimidin-2-yl)phenyl)urea;

(S)-1-methyl-3-(4-(4-(3-methylmorpholino)-6,6-dioxido-5,7-dihydrothieno[3,4-d]pyrimidin-2-yl)phenyl)urea;

(S)-1-(2-hydroxyethyl)-3-(4-(4-(3-methylmorpholino)-6,6-dioxido-5,7-dihydrothieno[3,4-d]pyrimidin-2-yl)phenyl)urea;

(S)-1-(2-fluoroethyl)-3-(4-(4-(3-methylmorpholino)-6,6-dioxido-5,7-dihydrothieno[3,4-d]pyrimidin-2-yl)phenyl)urea;

1-(4-(4-(8-oxa-3-azabicyclo[3.2.1]octan-3-yl)-6,6-dioxido-5,7-dihydrothieno[3,4-d]pyrimidin-2-yl)phenyl)-3-ethylurea;

1-(4-(4-(8-oxa-3-azabicyclo[3.2.1]octan-3-yl)-6,6-dioxido-5,7-dihydrothieno[3,4-d]pyrimidin-2-yl)phenyl)-3-(2-hydroxyethyl)urea;

(R)-1-cyclopropyl-3-(4-(4-(3-methylmorpholino)-6,6-dioxido-5,7-dihydrothieno[3,4-d]pyrimidin-2-yl)phenyl)urea;

1-(4-(4-(8-oxa-3-azabicyclo[3.2.1]octan-3-yl)-6,6-dioxido-5,7-dihydrothieno[3,4-d]pyrimidin-2-yl)phenyl)-3-cyclopropylurea;

1-(4-(4-(8-oxa-3-azabicyclo[3.2.1]octan-3-yl)-6,6-dioxido-5,7-dihydrothieno[3,4-d]pyrimidin-2-yl)phenyl)-3-methylurea;

1-(4-(4-(8-oxa-3-azabicyclo[3.2.1]octan-3-yl)-6,6-dioxido-5,7-dihydrothieno[3,4-d]pyrimidin-2-yl)phenyl)-3-(2-fluoroethyl)urea;

(S)-1-cyclopropyl-3-(4-(4-(3-methylmorpholino)-6,6-dioxido-7,8-dihydro-5H-thiopyrano[4,3-d]pyrimidin-2-yl)phenyl)urea;

(S)-1-cyclopropyl-3-(4-(4-(3-methylmorpholino)-7,8-dihydro-5H-thiopyrano[4,3-d]pyrimidin-2-yl)phenyl)urea;

(S)-1-(2,2-difluoroethyl)-3-(4-(4-(3-methylmorpholino)-6,6-dioxido-5,7-dihydrothieno[3,4-d]pyrimidin-2-yl)phenyl)urea;

1-(4-(4-(8-oxa-3-azabicyclo[3.2.1]octan-3-yl)-6,6-dioxido-5,7-dihydrothieno[3,4-d]pyrimidin-2-yl)phenyl)-3-(2,2-difluoroethyl)urea;

(S)-1-isopropyl-3-(4-(4-(3-methylmorpholino)-6,6-dioxido-5,7-dihydrothieno[3,4-d]pyrimidin-2-yl)phenyl)urea;

1-(4-(4-(3-oxa-8-azabicyclo[3.2.1]octan-8-yl)-6,6-dioxido-5,7-dihydrothieno[3,4-d]pyrimidin-2-yl)phenyl)-3-cyclopropylurea;

1-cyclopropyl-3-(4-(4-(3-ethylmorpholino)-6,6-dioxido-5,7-dihydrothieno[3,4-d]pyrimidin-2-yl)phenyl)urea;

(S)-1-(3-fluoropropyl)-3-(4-(4-(3-methylmorpholino)-6,6-dioxido-5,7-dihydrothieno[3,4-d]pyrimidin-2-yl)phenyl)urea;

1-(4-(4-(8-oxa-3-azabicyclo[3.2.1]octan-3-yl)-6,6-dioxido-5,7-dihydrothieno[3,4-d]pyrimidin-2-yl)phenyl)-3-(3-fluoropropyl)urea;

1-cyclopropyl-3-(4-(7-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(4-(3-methylmorpholino)-5,5-dioxido-6,7-dihydrothieno[3,2-d]pyrimidin-2-yl)phenyl)urea;

(S)-1-cyclopropyl-3-(4-(4-(3-methylmorpholino)-7,8-dihydro-6H-thiopyrano[3,2-d]pyrimidin-2-yl)phenyl)urea;

1-cyclopropyl-3-(4-(5-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(7,7-dimethyl-4-(3-methylmorpholino)-6,6-dioxido-5,7-dihydrothieno[3,4-d]pyrimidin-2-yl)phenyl)urea;

1-cyclopropyl-3-(4-(5-methyl-4-morpholino-6,6-dioxido-5,7-dihydrothieno[3,4-d]pyrimidin-2-yl)phenyl)urea;

1-cyclopropyl-3-(4-(4-(3-ethylmorpholino)-5-methyl-6,6-dioxido-5,7-dihydrothieno[3,4-d]pyrimidin-2-yl)phenyl)urea;

1-(4-(4-(3-oxa-8-azabicyclo[3.2.1]octan-8-yl)-5-methyl-6,6-dioxido-5,7-dihydrothieno[3,4-d]pyrimidin-2-yl)phenyl)-3-cyclopropylurea;

1-(4-(4-(8-oxa-3-azabicyclo[3.2.1]octan-3-yl)-5-methyl-6,6-dioxido-5,7-dihydrothieno[3,4-d]pyrimidin-2-yl)phenyl)-3-cyclopropylurea;

(S)-1-(4-(4-(3-methylmorpholino)-6,6-dioxido-5,7-dihydrothieno[3,4-d]pyrimidin-2-yl)phenyl)-3-(pyridin-4-yl)urea;

(S)-1-(4-(4-(3-methylmorpholino)-6,6-dioxido-5,7-dihydrothieno[3,4-d]pyrimidin-2-yl)phenyl)-3-(pyridin-3-yl)urea;

1-cyclopropyl-3-(4-((R)-5-methyl-4-((S)-3-methylmorpholino)-6,6-dioxido-5,7-dihydrothieno[3,4-d]pyrimidin-2-yl)phenyl)urea;

1-cyclopropyl-3-(4-((S)-5-methyl-4-((S)-3-methylmorpholino)-6,6-dioxido-5,7-dihydrothieno[3,4-d]pyrimidin-2-yl)phenyl)urea; and (S)-1-cyclopropyl-3-(4-(6,6-dimethyl-4-(3-methylmorpholino)-5,5-dioxido-6,7-dihydrothieno[3,2-d]pyrimidin-2-yl)phenyl)urea.

Further preferred compounds of the present invention are selected from the group consisting of 1-ethyl-3-(4-(5-methyl-4-((S)-3-methylmorpholino)-6,6-dioxido-5,7-dihydrothieno[3,4-d]pyrimidin-2-yl)phenyl)urea;

1-ethyl-3-(4-((R)-5-methyl-4-((S)-3-methylmorpholino)-6,6-dioxido-5,7-dihydrothieno[3,4-d]pyrimidin-2-yl)phenyl)urea;

1-ethyl-3-(4-((S)-5-methyl-4-((S)-3-methylmorpholino)-6,6-dioxido-5,7-dihydrothieno[3,4-d]pyrimidin-2-yl)phenyl)urea;

1-ethyl-3-(4-(4-((S)-3-ethylmorpholino)-7-methyl-6,6-dioxido-5,7-dihydrothieno[3,4-d]pyrimidin-2-yl)phenyl)urea;

1-ethyl-3-(4-(5,7,7-trimethyl-4-((S)-3-methylmorpholino)-6,6-dioxido-5,7-dihydrothieno[3,4-d]pyrimidin-2-yl)phenyl)urea;

1-cyclopropyl-3-(4-(7-fluoro-7-methyl-4-((S)-3-methylmorpholino)-6,6-dioxido-5,7-dihydrothieno[3,4-d]pyrimidin-2-yl)phenyl)urea;

1-cyclopropyl-3-(4-(5,7-dimethyl-4-((S)-3-methylmorpholino)-6,6-dioxido-5,7-dihydrothieno[3,4-d]pyrimidin-2-yl)phenyl)urea;

1-(4-(5-methyl-4-((S)-3-methylmorpholino)-6,6-dioxido-5,7-dihydrothieno[3,4-d]pyrimidin-2-yl)phenyl)-3-propylurea;

1-(cyclopropylmethyl)-3-(4-(5-methyl-4-((S)-3-methylmorpholino)-6,6-dioxido-5,7-dihydrothieno[3,4-d]pyrimidin-2-yl)phenyl)urea;

1-cyclopropyl-3-(4-(4-((S)-3-ethylmorpholino)-5-methyl-6,6-dioxido-5,7-dihydrothieno[3,4-d]pyrimidin-2-yl)phenyl)urea;

1-cyclopropyl-3-(4-(5-methyl-4-((R)-3-methylmorpholino)-6,6-dioxido-5,7-dihydrothieno[3,4-d]pyrimidin-2-yl)phenyl)urea;

1-cyclopropyl-3-(4-(5-ethyl-4-((S)-3-methylmorpholino)-6,6-dioxido-5,7-dihydrothieno[3,4-d]pyrimidin-2-yl)phenyl)urea;

1-ethyl-3-(2-fluoro-4-(5-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(4-(3-ethylmorpholino)-7,7-dimethyl-6,6-dioxido-5,7-dihydrothieno[3,4-d]pyrimidin-2-yl)phenyl)urea;

1-ethyl-3-(4-((R)-4-((S)-3-ethylmorpholino)-5-methyl-6,6-dioxido-5,7-dihydrothieno[3,4-d]pyrimidin-2-yl)phenyl)urea;

1-ethyl-3-(4-((S)-4-((S)-3-ethylmorpholino)-5-methyl-6,6-dioxido-5,7-dihydrothieno[3,4-d]pyrimidin-2-yl)phenyl)urea;

(R)-1-cyclopropyl-3-(4-(7,7-dimethyl-4-(3-methylmorpholino)-6,6-dioxido-5,7-dihydrothieno[3,4-d]pyrimidin-2-yl)phenyl)urea;

(R)-1-(4-(7,7-dimethyl-4-(3-methylmorpholino)-6,6-dioxido-5,7-dihydrothieno[3,4-d]pyrimidin-2-yl)phenyl)-3-ethylurea;

(S)-1-ethyl-3-(4-(4-(3-ethylmorpholino)-7,7-dimethyl-6,6-dioxido-5,7-dihydrothieno[3,4-d]pyrimidin-2-yl)phenyl)urea;

(S)-1-(4-(7,7-dimethyl-4-(3-methylmorpholino)-6,6-dioxido-5,7-dihydrothieno[3,4-d]pyrimidin-2-yl)phenyl)-3-methylurea;

1-methyl-3-(4-(5-methyl-4-((S)-3-methylmorpholino)-6,6-dioxido-5,7-dihydrothieno[3,4-d]pyrimidin-2-yl)phenyl)urea;

1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-cyclopropylurea;

1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-ethylurea;

(S)-1-(4-(7,7-dimethyl-4-(3-methylmorpholino)-6,6-dioxido-5,7-dihydrothieno[3,4-d]pyrimidin-2-yl)phenyl)-3-(2-fluoroethyl)urea;

(S)-1-(4-(7,7-dimethyl-4-(3-methylmorpholino)-6,6-dioxido-5,7-dihydrothieno[3,4-d]pyrimidin-2-yl)phenyl)-3-ethylurea;
1-cyclopropyl-3-(4-((S)-5-methyl-4-((R)-3-methylmorpholino)-6,6-dioxido-5,7-dihydrothieno[3,4-d]pyrimidin-2-yl)phenyl)urea;
(S)-1-(4-(4-(3-ethylmorpholino)-7,7-dimethyl-6,6-dioxido-5,7-dihydrothieno[3,4-d]pyrimidin-2-yl)-2-fluorophenyl)-3-methylurea;
(S)-1-(4-(7,7-dimethyl-4-(3-methylmorpholino)-6,6-dioxido-5,7-dihydrothieno[3,4-d]pyrimidin-2-yl)-2-fluorophenyl)-3-methylurea;
(S)-1-(4-(7,7-dimethyl-4-(3-methylmorpholino)-6,6-dioxido-5,7-dihydrothieno[3,4-d]pyrimidin-2-yl)-3-fluorophenyl)-3-methylurea;
1-ethyl-3-(4-(5-ethyl-4-((S)-3-methylmorpholino)-6,6-dioxido-5,7-dihydrothieno[3,4-d]pyrimidin-2-yl)phenyl)urea;
(S)-1-(4-(7,7-dimethyl-4-(3-methylmorpholino)-6,6-dioxido-5,7-dihydrothieno[3,4-d]pyrimidin-2-yl)phenyl)-3-(oxetan-3-yl)urea;
(S)-1-(4-(7,7-dimethyl-4-(3-methylmorpholino)-6,6-dioxido-5,7-dihydrothieno[3,4-d]pyrimidin-2-yl)-3-fluorophenyl)-3-ethylurea;
(S)-1-cyclopropyl-3-(4-(7,7-dimethyl-4-(3-methylmorpholino)-6,6-dioxido-7,8-dihydro-5H-thiopyrano[4,3-d]pyrimidin-2-yl)phenyl)urea;
1-cyclopropyl-3-(4-(7-methyl-4-((S)-3-methylmorpholino)-6,6-dioxido-7,8-dihydro-5H-thiopyrano[4,3-d]pyrimidin-2-yl)phenyl)urea;
1-cyclopropyl-3-(4-(5,7-dimethyl-4-((S)-3-methylmorpholino)-6,6-dioxido-7,8-dihydro-5H-thiopyrano[4,3-d]pyrimidin-2-yl)phenyl)urea;
(S)-1-(4-(7,7-dimethyl-4-(3-methylmorpholino)-6,6-dioxido-7,8-dihydro-5H-thiopyrano[4,3-d]pyrimidin-2-yl)phenyl)-3-ethylurea;
1-cyclopropyl-3-(4-(5-methyl-4-((S)-3-methylmorpholino)-6,6-dioxido-7,8-dihydro-5H-thiopyrano[4,3-d]pyrimidin-2-yl)phenyl)urea;
1-(2-fluoroethyl)-3-(4-(5,7,7-trimethyl-4-((S)-3-methylmorpholino)-6,6-dioxido-5,7-dihydrothieno[3,4-d]pyrimidin-2-yl)phenyl)urea;
1-(4-(7,7-dimethyl-4-morpholino-6,6-dioxido-5,7-dihydrothieno[3,4-d]pyrimidin-2-yl)phenyl)-3-ethylurea;
1-methyl-3-(4-(5,7,7-trimethyl-4-((S)-3-methylmorpholino)-6,6-dioxido-5,7-dihydrothieno[3,4-d]pyrimidin-2-yl)phenyl)urea;
1-(3-fluoro-4-(5,7,7-trimethyl-4-((S)-3-methylmorpholino)-6,6-dioxido-5,7-dihydrothieno[3,4-d]pyrimidin-2-yl)phenyl)-3-methylurea;
1-(4-(4-((S)-3-ethylmorpholino)-5,7,7-trimethyl-6,6-dioxido-5,7-dihydrothieno[3,4-d]pyrimidin-2-yl)-3-fluorophenyl)-3-methylurea;
1-(4-(4-((S)-3-ethylmorpholino)-5,7,7-trimethyl-6,6-dioxido-5,7-dihydrothieno[3,4-d]pyrimidin-2-yl)phenyl)-3-methylurea;
1-(2-fluoroethyl)-3-(4-(5,7,7-trimethyl-4-morpholino-6,6-dioxido-5,7-dihydrothieno[3,4-d]pyrimidin-2-yl)phenyl)urea; and
1-cyclopropyl-3-(4-((R)-5,7,7-trimethyl-4-((S)-3-methylmorpholino)-6,6-dioxido-5,7-dihydrothieno[3,4-d]pyrimidin-2-yl)phenyl)urea.

Where tautomerism, like e.g. keto-enol tautomerism, of compounds of general formula (I) may occur, the individual forms, like e.g. the keto and enol form, are comprised separately and together as mixtures in any ratio. The same applies to stereoisomers, like e.g. enantiomers, cis/trans isomers, conformers and the like.

Especially, compounds of formula (I), wherein the morpholino ring is substituted with one $R^1$ (other than H) in 3-position and/or different substituents $R^{14}/R^{14a}$, $R^{14b}/R^{14c}$ are encompassed by the present invention as isomers, enantiomers, diastereomers or mixtures thereof concerning the respective chiral carbon center(s).

If desired, isomers can be separated by methods well known in the art, e.g. by liquid chromatography. The same applies for enantiomers by using e.g. chiral stationary phases. Similarly diastereomers may be separated by conventional liquid chromatography or by using chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer or diastereomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

If desired, the effects of the claimed compounds on mTOR activity may e.g. be tested using transiently expressed epitope-tagged mTOR in a mammalian cell line such as HEK293 that is immunoprecipitated with a monoclonal antibody directed against the epitope tag (Knight et al. 2004, Bioorganic and Medicinal Chemistry 12, 4749-4759). Another assay employs mTOR protein enriched from cells or tissue lysates using conventional protein purification methods. In this assay a GST-fusion protein of the P70 S6 kinase is used as a substrate. The phosphorylation of P70 S6 is detected using a primary phospho-specific antibody (directed against phosphorylated threonine 389) and an enzyme linked secondary anti-body in an ELISA assay (US-A 2004/0191836).

According to the present invention, the expression "mTOR" or "mTOR kinase" means the mTOR protein (Tsang et al., 2007, Drug Discovery Today 12, 112-124). The gene encoding mTOR is located on human chromosome map locus 1p36.2 and it is widely expressed in human tissues.

As shown in the examples, compounds of the invention were tested for their selectivity for mTOR over other kinases. As shown, tested compounds bind mTOR more selectively than the kinases PI3 Kdelta or DNA-PK (see tables 9 and 10 below). Consequently, the compounds of the present invention are considered to be useful for the prevention or treatment of diseases and disorders associated with mTOR, e.g. immunological, inflammatory, autoimmune, or allergic disorders, or proliferative diseases, transplant rejection, Graft-versus-Host-Disease, cardiovascular diseases, metabolic diseases or neurodegenerative diseases.

Therefore, the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or mTOR inhibitors. Further bioactive compounds for may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD 1839), Λ/-(3-ethynylphenyl)-6,7-bis(2-methoxyethoxy)quinazolin-4-amine (erlotinib, OSI-774) and 6-acrylamido-Λ/-(3-chloro-4-fluorophenyl)-7-(3-morpholinopropoxy)-quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazo line (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU1 1248 (sunitinib; WO 01/60814), and compounds that work by other mechanisms (for example linomide, inhibitors of integrin αvβ3 function and angio statin);

(vi) vascular damaging agents such as combretastatin A4 and compounds disclosed in International Patent Application WO 99/02166;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Further combination treatments are described in WO-A 2009/008992, incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with mTOR.

In the context of the present invention, a disease or disorder associated with mTOR is defined as a disease or disorder where mTOR is involved.

The link between the mTOR kinase and immunological diseases is demonstrated by the fact that the FDA approved in 1997 the mTOR inhibitor rapamycin (Sirolimus®) as a drug to prevent rejection of kidney transplants (Tsang et al., 2007, Drug Discovery Today 12, 112-124). Rapamycin blocks interleukin 2 (IL-2)-mediated T-cell proliferation and activation. Therefore mTOR inhibitors may be useful to treat other immunological, inflammatory, autoimmune and allergic diseases in which T cells play a role, for example rheumatoid arthritis (RA), inflammatory bowel disease (IBD; Crohns's disease and ulcerative colitis), psoriasis, systemic lupus erythematosus (SLE), and multiple sclerosis (MS).

In addition, the FDA approved in 2003 rapamycin as anti-restenosis drug used in coronary-artery stents because rapamycin is a potent inhibitor of the proliferation of vascular smooth muscle cells (Tsang et al., 2007, Drug Discovery Today 12, 112-124). Therefore mTOR inhibitors may be useful for the treatment of other diseases in which excessive cell proliferation plays a role.

The rapamycin analogs (rapalogs) temsirolimus and everolimus are approved for use in advanced renal cell carcinoma, demonstrating the utility of inhibition of the mTOR pathway in cancer treatments (Richard et al., 2011. Current Opinion Drug Discovery and Development 13(4):428-440).

Although the compounds of the present invention act as mTOR kinase inhibitors and do not have the same mode of action as rapamycin, it can be expected that this class of mTOR inhibitors will have utility in the same indications as rapamycin and additional indications as described below.

In a preferred embodiment, the diseases or disorder associated with mTOR is an immunological, inflammatory, autoimmune, or allergic disorder or disease or a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease or a transplant rejection or a Graft-versus host disease.

According to the present invention, an autoimmune disease is a disease which is at least partially provoked by an immune reaction of the body against own components, e.g. proteins, lipids or DNA.

In a preferred embodiment, the autoimmune disease is selected from the group consisting of rheumatoid arthritis (RA), inflammatory bowel disease (IBD; Crohns's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schön et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Graft-versus-host disease (GVDH) is a major complication in allogeneic bone marrow transplantation. GVDH is caused by donor T cells that recognize and react to recipient differences in the histocompatibility complex system, resulting in significant morbidity and mortality.

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection.

In a further preferred embodiment, the disease or disorder associated with mTOR is a proliferative disease, especially cancer.

Diseases and disorders associated especially with mTOR are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

Especially cancers in which the PI3K/Akt signal transduction pathway is activated, for example due to inactivation of the tumour suppressor PTEN or activating mutations in PIK3A, the gene encoding the catalytic phosphoinositide-3 kinase subunit p110α (p110alpha) are expected to respond to treatment with mTOR inhibitors (Garcia-Echeverria and Sellers, 2008, Oncogene 27, 5511-5526). Examples of cancers with a high incidence of PTEN mutations and/or activation of PI3K/Akt are endometrial carcinoma, glioblastoma, head and neck cancer, colon cancer, pancreatic cancer, gastric cancer, hepatocarcinoma, ovarian cancer, thyroid carcinoma, renal cell cancer, breast cancer, prostate cancer and gastrointestinal stromal tumours (GIST). The most promising results with mTOR inhibitors have been obtained in renal cell carcinoma (RCC), mantle cell lymphoma and endometrial cancers (Faivre et al., 2006. Nat. Rev. Drug. Discov. 5(8):671-688). In addition, mTOR inhibitors may be useful for the treatment of leukemias Including ALL and CML, multiple myeloma and lymphomas.

In addition, cancers harbouring activating mTOR mutations, for example single amino acid changes that confer constitutive activation of mTOR such as S2215Y or R2505P, may be treated with mTOR inhibitors (Sato et al., 2010, Oncogene 29(18):2746-2752).

mTOR plays an important role in angiogenesis, the formation of new blood vessels to provide oxygen and nutrients to growing and dividing cells. In this context mTOR controls the production of the HIF1-α and HIF1-β proteins, which are subunits of hypoxia-inducible factor (HIF), a transcription factor that controls the expression of genes whose products play a role in angiogenesis, cell proliferation, motility and survival. Two important proteins induced by HIF are vascular endothelial growth factors (VEGFs) and angiopoietin-2. Recently it has been reported that a small molecule mTOR inhibitor can reduce tumour growth, tumour angiogenesis an vascular permeability (Xue et al., 2008. Cancer Research 68(22): 9551-9557).

In addition to tumourigenesis, there is evidence that mTOR plays a role in harmatoma syndromes. Recent studies have shown that the tumour suppressor proteins such as TSC1, TSC2, PTEN and LKB1 tightly control mTOR signalling. Loss of these tumour suppressor proteins leads to a range of hamartoma conditions as a result of elevated mTOR signalling (Rosner et al., 2008. Mutation Research 659(3):284-292). Syndromes with an established molecular link to dysregulation of mTOR include Peutz-Jeghers syndrome (PJS), Cowden disease, Bannayan-Riley-Ruvalcaba syndrome (BRRS), Proteus syndrome, Lhermitte-Duclos disease and Tuberous sclerosis (TSC). Patients with these syndromes characteristically develop benign hamartomatous tumours in multiple organs. Other tumour suppressor proteins having an influence on mTOR activity are VHL, NF1 and PKD whose loss can trigger von Hippel-Lindau disease, Neurofibromatosis type 1, and Polycystic kidney disease respectively.

Proliferative diseases or disorders comprise a group of diseases characterized by increased cell multiplication. One example is restenosis caused by the overgrowth of vascular smooth muscle (VSM) cells after coronary angioplasty with stents. To circumvent this issue, drug-eluting stents have been developed to inhibit the growth of VSM cells. Rapamycin-coated stents effectively reduce restenosis and have been approved by the FDA (Serruys et al., 2006. N. Engl. J. Med. 354(5):483-95).

In a further preferred embodiment, the disease or disorder associated with mTOR is a cardiovascular disease, a metabolic disease or a neurodegenerative disease.

Therefore, another aspect of the present invention is a compound or a pharmaceutically acceptable salt thereof of the present invention for use in a method of treating or preventing a cardiovascular disease, a metabolic disease or a neurodegenerative disease.

Recent studies have revealed a role of mTOR in cardiovascular diseases, for example elevated mTOR kinase activity has been associated with cardiac hypertrophy (heart enlargement), which is a major risk factor for heart failure. At the cellular level, cardiac hypertrophy is characterized by an increase in cell size and enhanced protein synthesis. Although there are various hypertrophic stimuli, such as neurohormones and peptide growth factors, and several protein kinase cascades are involved in cardiac hypertrophy, it is likely that all forms of hypertrophic stimuli activate the general protein translational machinery in an mTOR dependent manner. Remarkably, inhibition of mTOR by rapamycin prevents cardiac hypertrophy in numerous transgenic mouse models. In addition, stress-induced cardiac hypertrophy is dependent on mTOR in mice. These results indicate that mTOR is crucial for the abnormal cardiac overgrowth, and that mTOR inhibitors may be useful for the treatment of human cardiac hypertrophy (Tsang et al., 2007, Drug Discovery Today 12, 112-124).

Metabolic diseases that may be treated with mTOR inhibitors comprise type 1 diabetes, type 2 diabetes, and obesity (Tsang et al., 2007, Drug Discovery Today 12, 112-124). Type 1 diabetes is caused by loss of insulin production due to destruction of pancreatic β-cells. Clinical studies using immunosuppressive regimen that contain rapamycin to prevent rejection of islet transplants have shown significant efficacy in type 1 diabetic patients. Type 2 diabetes arises when insulin secretion from pancreatic β-cells fails to compensate for the peripheral insulin resistance (or insensitivity to insulin) in skeletal muscle, liver and fat cells. Recent data indicate that sustained activation of mTOR signalling is a crucial event that renders insulin-receptors substrate (IRS) irresponsive to insulin. Moreover, it has been demonstrated that rapamycin restores the sensitivity of IRS to insulin (Shah et al., 2004. Curr. Biol. 14(18):1650-1656). Therefore, mTOR inhibitors are potentially useful in the management of type 2 diabetes. Obesity is a metabolic disease with a steadily increasing health risk worldwide. Recent evidence suggests that mTOR plays a role in lipid metabolism. During adipogenesis the expression of mTOR increases dramatically from barely detectable in preadipocytes to highly expressed in fully differentiated adipocytes, and rapamycin inhibits adipocyte differentiation (Yeh et al., 1995. Proc. Natl. Acad. Sci. USA. 92(24):11086-90).

Recent reports suggest that mTOR inhibitors may be useful to treat neurodegenerative diseases such as Huntingtons's, Alzheimer's and Parkinson's disease. Huntingtons's disease is a neurodegenerative disorder caused by a mutant form of the protein huntingtin with abnormally long glutamine repeats at the amino-terminus. The mutant protein aggregates in neuronal cells and can cause nerve cell damage and toxicity. Rapamycin attenuates the accumulation of huntingtin and cell death, and protects against neurodegeneration in animal models of Huntington's disease (Ravikumar et al., 2004. Nat Genet. 36(6):585-95). In addition, rapamycin induces an autophagy response that has been suggested to play a role in the clearance of huntingtin aggregates.

Intracellular protein aggregates also occur in other neurodegenerative diseases, for example Alzheimer's disease. The Tau protein is frequently found in brains of Alzheimer's patients and is thought to contribute to the formation of neurofibrillary tangles (for example in tauopathies such as fronto-temporal dementia). In a fly model rapamycin reduces the concentration of tau protein and lowers the toxicity caused by tau accumulation (Berger et al., 2006. Hum Mol Genet. 2006 Feb. 1; 15(3):433-42). Therefore, mTOR inhibitors may be useful in preventing the accumulation of toxic tau protein in Alzheimer's patients.

Parkinson's disease (PD) is a neurodegenerative disease associated with the accumulation and aggregation of misfolded proteins. Preventing aggregation or disaggregating misfolded proteins may provide a therapeutic benefit by slowing or preventing the progression of PD. The ubiquitin-proteasome system (UPS) is an important degradation mechanism acting on aggregated proteins. It was reported that rapamycin provides neuroprotection against dopaminergic neuronal cell death induced by the proteasome inhibitor lactacystin. It was suggested that the rapamycin effect is partially mediated by autophagy enhancement through enhanced degradation of misfolded proteins (Pan et al., 2008. Neurobiol. Dis. 32(1):16-25). Therefore compounds that can enhance autophagy may represent a promising strategy to treat PD patients.

In a further preferred embodiment, the disease or disorder associated with mTOR is an autophagy associated disease.

Therefore, another aspect of the present invention is a compound or a pharmaceutically acceptable salt thereof of the present invention for use in a method of treating or preventing an autophagy associated disease.

Autophagy is a lysosome-dependent process whereby proteins or damaged organelles within a cell are degraded (Mizushima et al., 2008. Nature 451(7182):1069-75). During this process an autophagosome with a double membrane encloses the component of the cell to be degraded. Then the autophagosome fuses with a lysosome which for example degrades proteins leading to the recycling of amino acids. Autophagy is primarily involved in the degradation of long-lived proteins, protein aggregates, and cellular organelles and other cellular components. In addition to its physiological function autophagy could be expoited for the treatment of a variety of diseases caused by misfolded proteins aggregates, for example neurodegenerative diseases such as Huntington's, Alzheimer's or Parkinon's disease. Further autophagy associated diseases are described in WO-A2009/049242, incorporated herein with reference.

Autophagy inducing compound refers to a compound that induces autophagy in a cell. Autophagy associated disease refers to a disease that can be treated by the induction of autophagy. It has recently been shown that an ATP-competitive mTOR kinase inhibitor can induce autophagy (Thoreen et al., 2009. J. Biol. Chem. 284(12):8023-32). Interestingly, ATP competitive mTOR kinase inhibitors seem to induce autophagy more effectively than rapamycin in mammalian cells. Taken together, compounds of the present invention may be useful to induce autophagy in cells and to treat autophagy associated diseases.

In a further preferred embodiment, the disease or disorder is a viral infection.

Therefore, another aspect of the present invention is a compound or a pharmaceutically acceptable salt thereof of the present invention for use in a method of treating or preventing a viral infection.

All viruses require cellular ribosomes to translate their mRNAs. For example, Human cytomegalovirus (HCMV) infection has been shown to activate the mTORC1 signaling pathway. Treatment of infected cells with Torinl, a mTOR inhibitor that targets the catalytic site of mTOR kinase, blocks the production of virus progeny. In addition, it was shown that Torinl inhibits the replication of representative members of the alpha-, beta-, and gammaherpesvirus families, demonstrating the potential of mTOR kinase inhibitors as broad-spectrum antiviral agents (Moorman and Shenk, 2010. J. Virol. 84(10):5260-9). Further viral infections that may be treated or prevented by mTOR inhibitors are described in WO-A 2011/011716 incorporated herein with reference.

Yet another aspect of the present invention is the use of a compound of the present invention or a pharmaceutically acceptable salt thereof for the manufacture of a medicament for the treatment or prophylaxis of diseases and disorders associated with mTOR.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

Yet another aspect of the present invention is the use of a compound of the present invention or a pharmaceutically acceptable salt thereof for the manufacture of a medicament for treating or preventing a cardiovascular disease, a metabolic disease or a neurodegenerative disease.

Yet another aspect of the present invention is the use of a compound of the present invention or a pharmaceutically acceptable salt thereof for the manufacture of a medicament for treating or preventing an autophagy associated disease.

Yet another aspect of the present invention is the use of a compound of the present invention or a pharmaceutically acceptable salt thereof for the manufacture of a medicament for treating or preventing a viral infection.

In the context of these uses of the invention, diseases and disorders associated with mTOR are as defined above.

Yet another aspect of the present invention is a method for treating, controlling, delaying or preventing in a mammalian patient in need thereof one or more conditions selected from the group consisting of diseases and disorders associated with mTOR, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of a cardiovascular disease, a metabolic disease or a neurodegenerative disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof an autophagy associated disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a viral infection, wherein the method comprises the administration to said patient a therapeutically effective amount of a compound according to present invention or a pharmaceutically acceptable salt thereof.

In the context of these methods of the invention, diseases and disorders associated with mTOR are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

All embodiments discussed above with respect to the pharmaceutical composition of the invention also apply to the above mentioned first or second medical uses or methods of the invention.

Exemplary routes for the preparation of compounds of the present invention are described below. It is clear to a practitioner in the art to combine or adjust such routes especially in combination with the introduction of activating or protective chemical groups.

A general route refers to a method for preparing a compound of the present invention comprising the step of reacting a compound of formula (II)

(II)

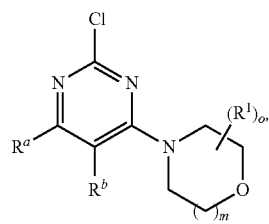

wherein $R^a$, $R^b$, $R^1$, o, m have the meaning as indicated in above, with a compound of formula $T^1$-X, wherein $T^1$ has the meaning as indicated in above and X is a suitable group for a Suzuki reaction, like 4,4,5,5-tertamethyl-1,3,2-dioxaborolan-2-yl, to yield a compound of formula (I).

By way of examples the following Schemes are provided. It is clear to a practitioner in the art to vary reaction conditions accordingly, especially to introduce steps for the activation of functional groups and/or for the protection of functional groups.

Scheme 1

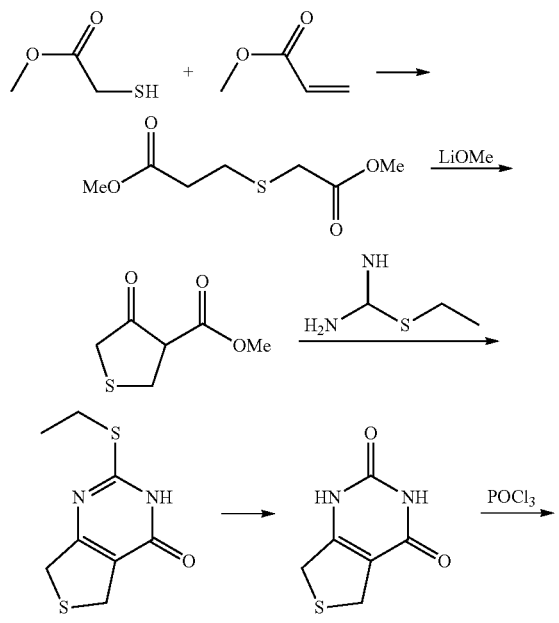

Scheme 2

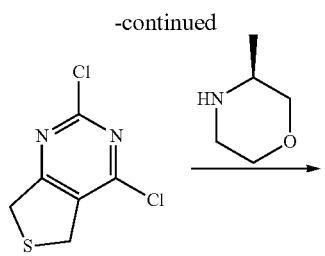

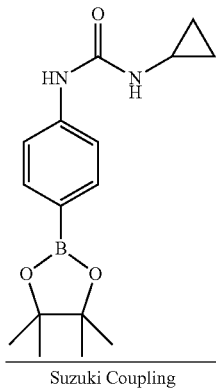

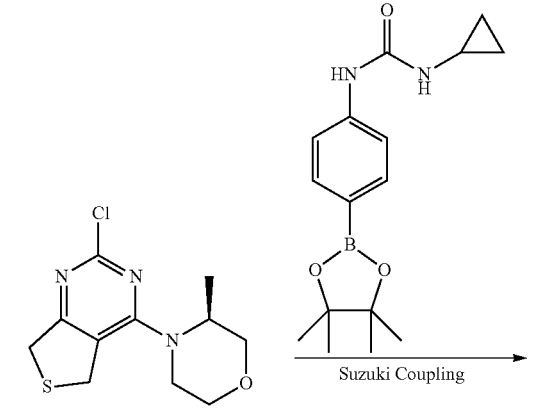

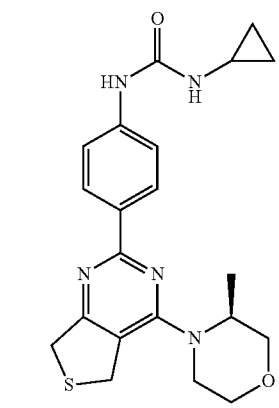

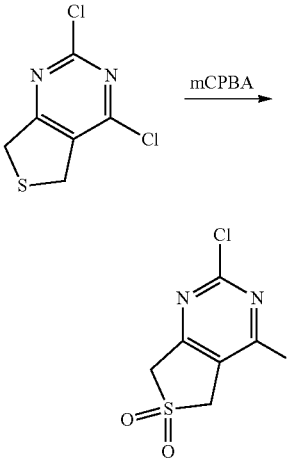

31
-continued
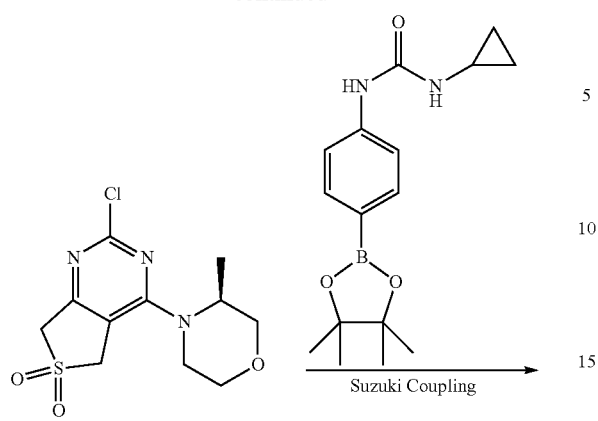
32
-continued
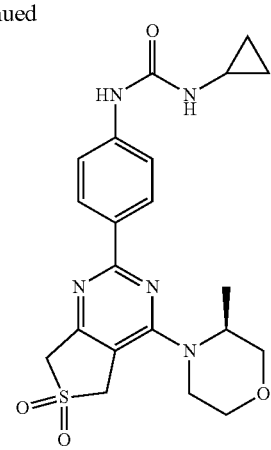
Scheme 3
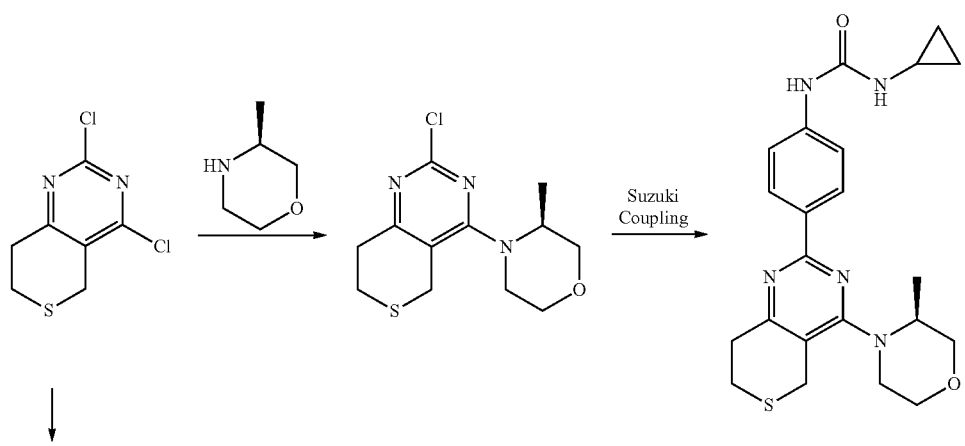
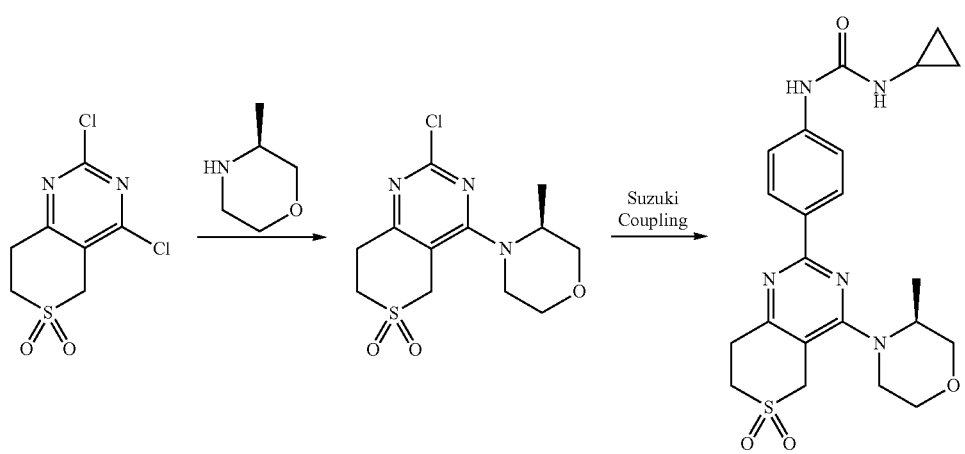

33    34
Scheme 4
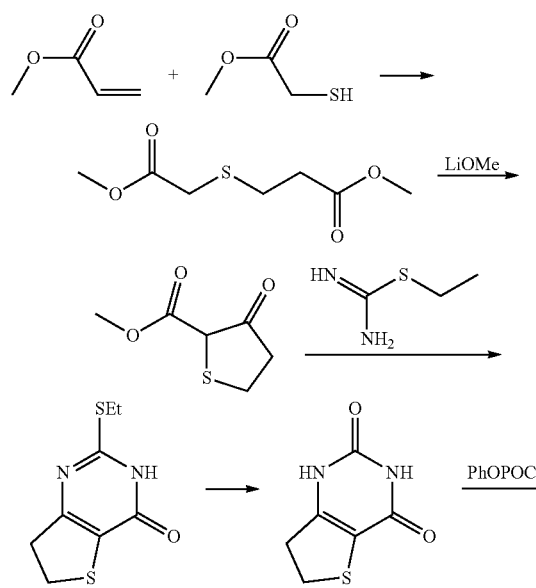
Scheme 5
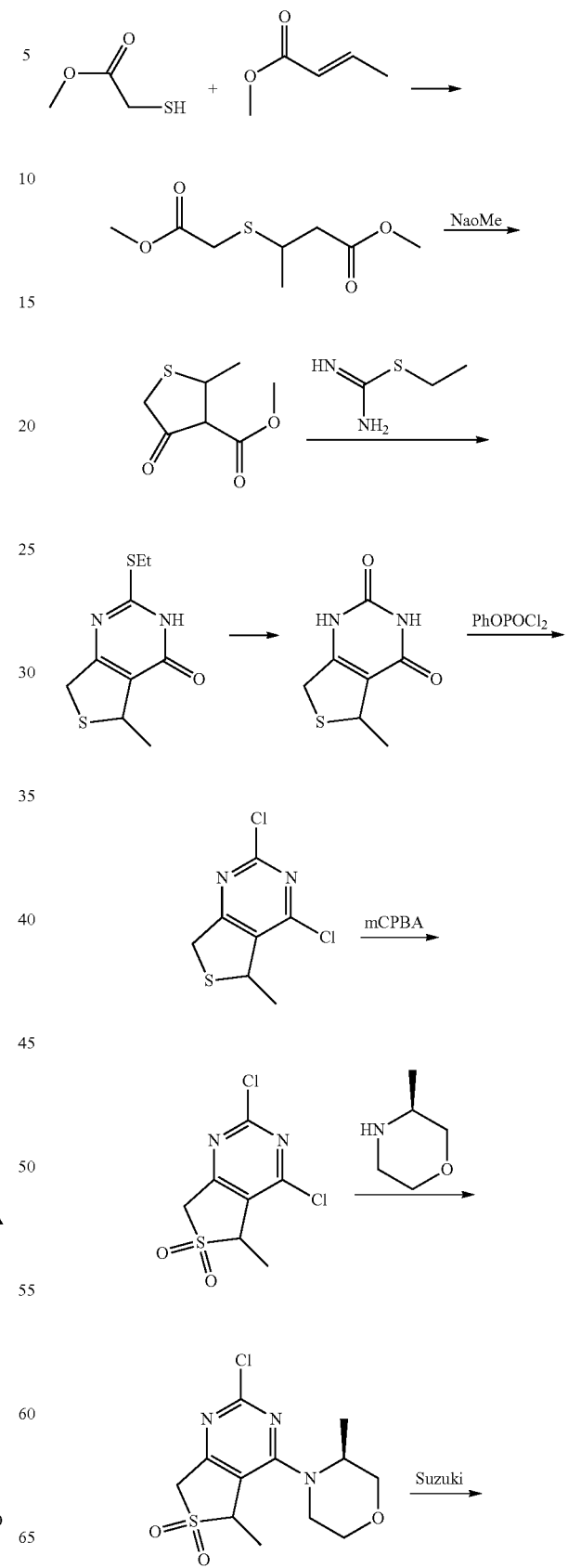

35
-continued
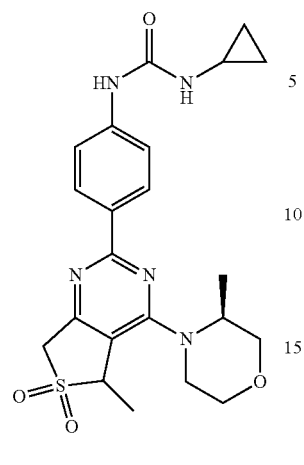
36
-continued
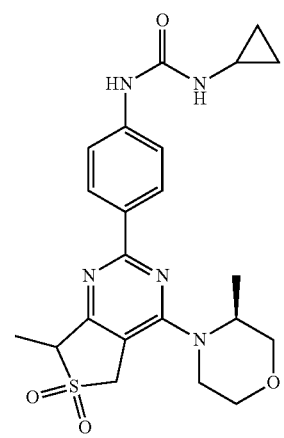
Scheme 6
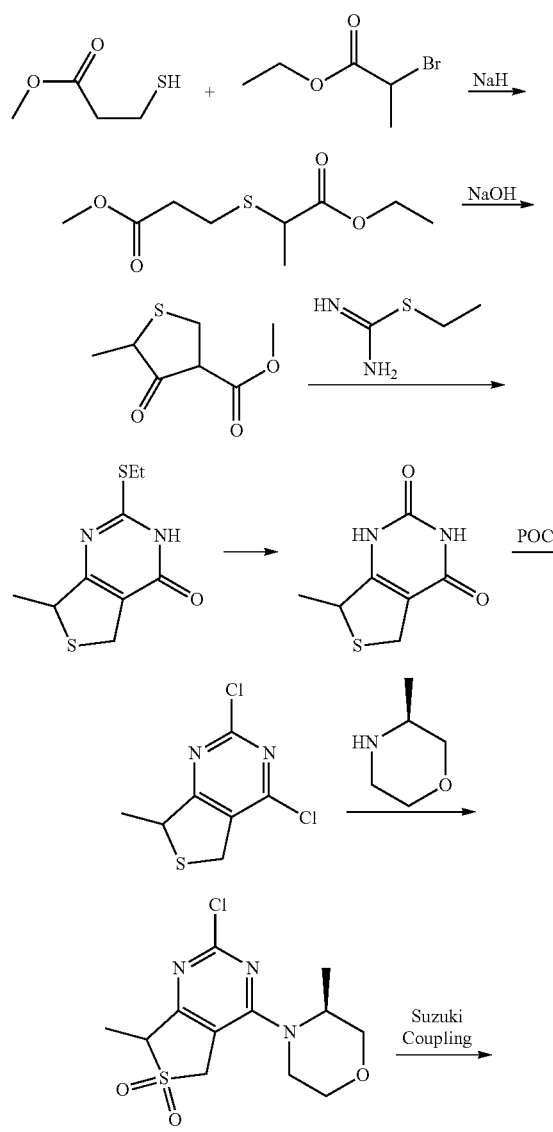
Scheme 7
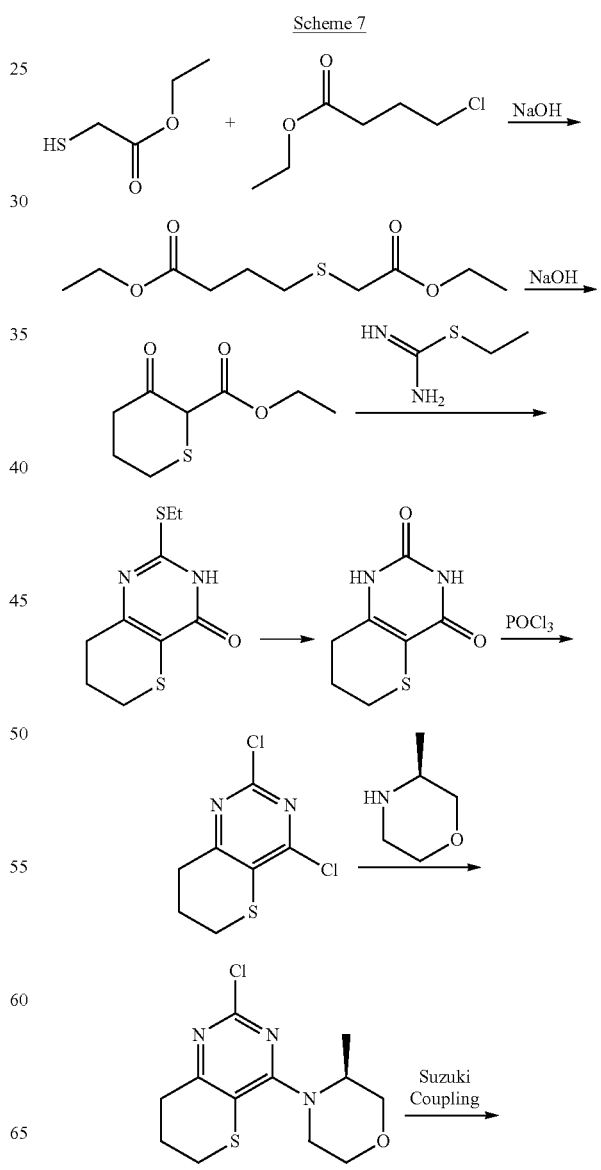

37
-continued

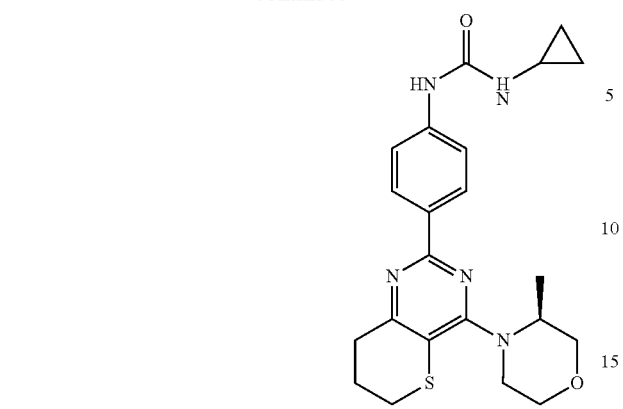

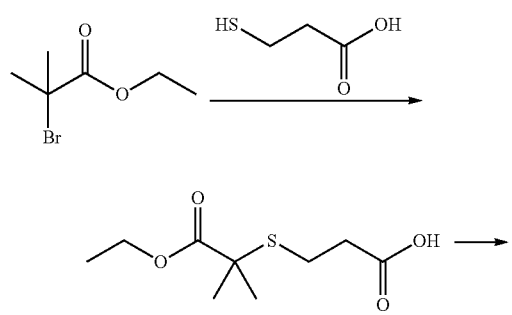

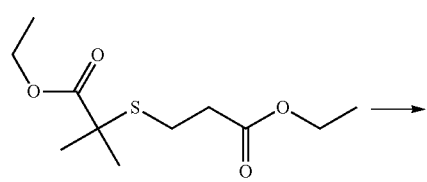

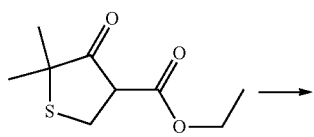

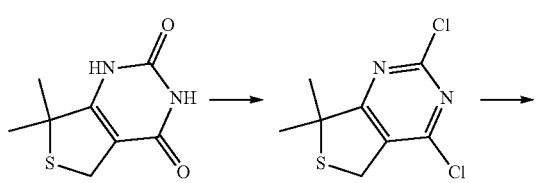

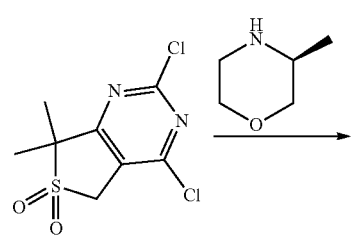

38
-continued

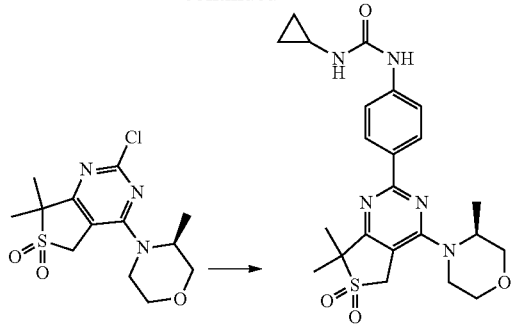 [SMILES: CC1c2c(N3CCOC[C@@H]3C)nc(Cl)nc2C(C)(C)S1(=O)=O ; CC1c2c(N3CCOC[C@@H]3C)nc(-c3ccc(NC(=O)NC4CC4)cc3)nc2C(C)(C)S1(=O)=O]

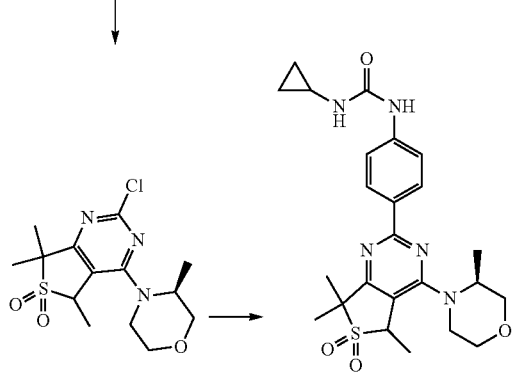

EXAMPLES

Materials and Methods

NMR $^1$H NMR spectra were recorded at 400 MHz using a Bruker AVANCE 400 MHz spectrometer.

LC-MS Equipment and Conditions as Follows:

LC-MS Method A:

Analysis was run on an Agilent Technologies 1200 series with binary pump,

Column: Waters xTerra, 3.5 m, 2.1×50 mm

Solvents: A=Water+0.07% Formic acid

B=Methanol

Flow Rate: 0.4 ml/min

Temperature: 25° C.

TABLE 1

| Time (min) | B (%) | A (%) |
| --- | --- | --- |
| 0 | 10 | 90 |
| 1 | 10 | 90 |
| 1.5 | 95 | 5 |
| 7.0 | 95 | 5 |
| 7.2 | 10 | 90 |
| 10 | 10 | 90 |

Wavelength: PDA detection from 200-400 nm

Mass spec conditions: G6110A, Quadrupole LCThe mass spec data were gathered in positive mode, scanning for masses between 50 and 900 amu LC/MS Method B:

Analysis was run on a Waters—ZQ system using the following conditions:

Column: Phenomenex Gemini NX C18 30×3 mm 3 μm

Solvents:

A=Water+0.1% Formic acid

B=(95% Acetonitrile: 5% Water)+0.1% Formic acid

Flow Rate: 1.5 ml/min
Temperature: Room temperature

TABLE 2

| Time (min) | % A | % B |
| --- | --- | --- |
| 0.00 | 95.0 | 5.0 |
| 0.50 | 95.0 | 5.0 |
| 3.00 | 0.0 | 100.0 |
| 4.50 | 0.0 | 100.0 |
| 4.60 | 95.0 | 5.0 |
| 6.00 | 95.0 | 5.0 |

Gradient:

Wavelength: PDA detection from 200-400 nm
Mass spec conditions: The mass spec data were gathered in positive and negative mode, scanning for masses between 150 and 700 amu, using a 20V cone voltage.
LC-MS Method C:
Analysis was run on an Agilent Technologies 1200 series with binary pump,
Column: Venusil XBP-C18 2.1×50 mm, 5 μm
Solvents: A=Water+0.04% TFA
B=Acetonitrile+0.02% TFA
Flow Rate: 0.6 mL/min
Temperature: 40° C.

TABLE 3

| Time (min) | B (%) | A (%) |
| --- | --- | --- |
| 0 | 0 | 100 |
| 0.4 | 0 | 100 |
| 3.4 | 80 | 20 |
| 3.85 | 100 | 0 |
| 3.86 | 0 | 100 |
| 4.50 | 0 | 100 |

Wavelength: PDA detection from 200-400 nm
Mass spec conditions: G6110A, Quadrupole LC The mass spec data were gathered in positive mode, scanning for masses between 100 and 1000 amu
LC-MS Method D:
Analysis was run on an Agilent Technologies 1200 series with binary pump,
Column: Venusil XBP-C18 2.1×50 mm, 5 μm
Solvents: A=Water+0.04% TFA
B=Acetonitrile+0.02% TFA
Flow Rate: 0.8 mL/min
Temperature: 40° C.

TABLE 4

| Time (min) | B (%) | A (%) |
| --- | --- | --- |
| 0.00 | 1 | 99 |
| 0.40 | 1 | 99 |
| 3.40 | 90 | 10 |
| 3.85 | 100 | 0 |
| 3.86 | 1 | 99 |
| 4.50 | 1 | 99 |

Wavelength: PDA detection from 200-400 nm
Mass spec conditions: The mass spec data were gathered in positive and negative mode, scanning for masses between 150 and 700 amu, using a 20V cone voltage.
LC-MS Method E:
Analysis was run on an Agilent Technologies 1200 series with binary pump,
Column: Waters Acquity UPLC BEH C18, 30×2.1 mm, 1.7 μm
Solvents: A=Water+0.1% formic acid
B=Acetonitrile+0.1% formic acid
Flow Rate: 0.5 mL/min
Temperature: 40° C.

TABLE 5

| Time (min) | B (%) | A (%) |
| --- | --- | --- |
| 0.00 | 5.0 | 95.0 |
| 0.20 | 5.0 | 95.0 |
| 1.00 | 95.0 | 5.0 |
| 1.50 | 95.0 | 5.0 |
| 1.70 | 5.0 | 95.0 |
| 2.70 | 5.0 | 95.0 |

Wavelength: PDA detection from 210-400 nm
Mass spec conditions: The mass spec data were gathered in positive and negative mode, scanning for masses between 150 and 1000 amu, using a 25 V cone voltage.
LC-MS Method F:
Analysis was run on an Agilent Technologies 1200 series with binary pump,
Column: Waters Acquity UPLC BEH C18, 50×2.1 mm, 1.7 μm
Solvents: A=Water+0.1% formic acid
B=Acetonitrile+0.1% formic acid
Flow Rate: 0.5 mL/min
Temperature: 40° C.

TABLE 6

| Time (min) | B (%) | A (%) |
| --- | --- | --- |
| 0.00 | 5.0 | 95.0 |
| 0.20 | 5.0 | 95.0 |
| 4.20 | 95.0 | 5.0 |
| 4.70 | 95.0 | 5.0 |
| 4.75 | 5.0 | 95.0 |
| 6.00 | 5.0 | 95.0 |

Wavelength: PDA detection from 210-400 nm
Mass spec conditions: The mass spec data were gathered in positive and negative mode, scanning for masses between 150 and 1000 amu, using a 25 V cone voltage.
LC-MS Method G:
Analysis was run on Shimadzu Technologies LC-20AD binary pump,
Column: HALO-C18 2.1×30 mm, 2.7 μm
Solvents: A=4 L Water (0.04% TFA)
B=4 L Acetonitrile (0.02% TFA)
Flow Rate: 1.0 ml/min
Temperature: 40° C.

TABLE 7

| Time (min) | B (%) | A (%) |
| --- | --- | --- |
| 0.00 | 10 | 90 |
| 1.15 | 90 | 10 |
| 1.55 | 90 | 10 |
| 1.56 | 10 | 90 |
| 2 | 10 | 90 |

Wavelength: PDA detection from 200-400 nm
Mass spec conditions: LCMS-2010EV, Quadrupole LC The mass spec data were gathered in positive mode, scanning for masses between 100 and 1000 amu

TABLE 8

| Abbreviations | |
|---|---|
| ACN | Acetonitrile |
| Ar | Aryl |
| aq | Aqueous |
| br | Broad |
| Boc | Tert-Butoxycarbonyl |
| BuLi | Butyllithium |
| d | Doublet |
| DCM | Dichloromethane |
| dd | Double doublet |
| ddd | Double doublet of doublets |
| DEAD | Diethyl azodicarboxylate |
| DIAD | Diisopropyl azodicarboxylate |
| DIPEA | Diisopropylethylamine |
| DME | 1,2-Dimethoxyethane |
| DMF | N,N'-Dimethylformamide |
| DMF-DMA | N,N-dimethylformamide dimethylacetal |
| DMSO | N,N'-dimethylsulfoxide |
| DP | Drug pulldown |
| dt | Doublet of triplets |
| DTT | Dithiothreitol |
| EDC | 1-Ethyl-3-(3-dimethylaminopropyl)carbodiimide |
| EDTA | Ethylenediaminetetraacetic acid |
| EtOAc | Ethyl acetate |
| EtOH | Ethanol |
| eq | Equivalents |
| g | Grams |
| h | Hours |
| HCl | Hydrochloric acid |
| $H_2O$ | Water |
| $H_2S$ | Hydrogen sulfide |
| HOBt | 1-Hydroxybenzotriazole |
| HPLC | High performance liquid chromatography |
| $IC_{50}$ | 50% inhibition concentration |
| iPr | Isopropyl |
| L | Litres |
| LC-MS | Liquid chromatography mass spectroscopy |
| m | Multiplet |
| M | Molar |
| MeOH | Methanol |
| Mesyl | Methanesulfonyl chloride |
| mg | Milligrams |
| $MgSO_4$ | Magnesium Sulphate |
| min | Minutes |
| mL | Millilitres |
| mm | Millimetres |
| mmol | Millimoles |
| mol % | Molar percent |
| μL | Microlitres |
| nm | Nanometres |
| NMR | Nuclear magnetic resonance |
| PBS | Phosphate buffered saline |
| q | Quartet |
| qu | Quintet |
| rpm | Revolutions per minute |
| rt | Room temperature |
| RT | Retention time |
| s | Singlet |
| sat. | Saturated |
| t | Triplet |
| td | Triplet of doublets |
| tdd | Triple doublet of doublets |
| THF | Tetrahydrofuran |
| tt | Triplet of triplets |
| tert | Tertiary |

Example 1

(S)-1-cyclopropyl-3-(4-(4-(3-methylmorpholino)-5,7-dihydrothieno[3,4-d]pyrimidin-2-yl)phenyl)urea

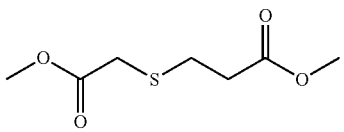

Step (i)

Methyl acrylate (99.2 mL, 1.1 mmol) was added slowly to a solution of methyl thioglycolate (91 mL, 1.0 mmol) and piperidine (2.0 mL, 0.02 mol) while maintaining the temperature of the reaction mixture at 50° C. The reaction was stirred for 2 h then the excessive methyl acrylate and piperidine were distilled off under high vacuum to give the target product methyl 3-((methoxycarbonyl)methylthio) propanoate (185 g, 96%).

LC-MS (Method A): (ES+) 193, RT=4.29 min.

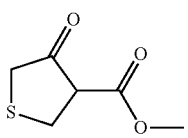

Step (ii)

Lithium metal (2.12 g, 0.30 mol) in toluene (250 mL) was treated with methanol (80 mL) at rt. After all the lithium had dissolved, methyl 3-((methoxycarbonyl)methylthio) propanoate was added over 0.5 h at 70° C. The reaction temperature was then raised (methanol was distilled off) to a final temperature 110° C. and this temperature maintained for 18 h. The mixture obtained contained the desired product and methyl 3-oxo-tetrahydrothiophene-2-carboxylate as a 1:1 mixture. The reaction was cooled and the solid collected by filtration, to provide an enriched solid containing the lithium salt of the desired product. The solid was acidified with 1 N HCl solution and extracted with DCM. The organic phase was concentrated and the residue was purified by column chromatography, eluting with EtOAc in petroleum ether (2% to 10%) to remove any remaining methyl 3-oxo-tetrahydrothiophene-2-carboxylate. Methyl tetrahydro-4-oxothiophene-3-carboxylate (14.7 g, 33%) was obtained as the second eluting fraction from the column.

LC-MS (Method A), (ES+) 161, RT=4.92 min.

Step (iii)

To a solution of S-ethyl isothiouronium bromide (3.0 g, 16.2 mmol) in water (60 mL) were added sodium carbonate (1.71 g, 16.2 mmol) and methyl tetrahydro-4-oxothiophene- 3-carboxylate (2.51 g, 16.2 mmol) dropwise. The mixture was stirred overnight at rt in the dark. The solid precipitant in the resulting mixture was collected by filtration, washed with water, diethyl ether, methanol and acetone, then the solid was dried under vacuum to obtain 2-(ethylthio)thieno[3,4-d]pyrimidin-4-(3H, 5H, 7H)-one as a white solid (2.88 g, 83%). Without further purification, the crude product was used directly in the next step.

LC-MS (Method A), (ES+) 215, RT=4.99 min.

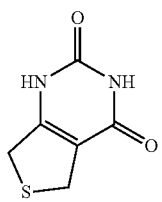

Step (iv)

To the suspension of 2-(ethylthio)thieno[3,4-d]pyrimidin-4-(3H, 5H, 7H)-one (2.88 g, 13.45 mmol) in water (20 mL) was added 2.0 mL of conc. HCl and 4.0 mL of AcOH. The reaction was heated at reflux overnight then cooled and the solid collected by filtration, washed with water and methanol, evaporated and dried to obtain a white solid thieno[3,4-d]pyrimidine-2,4-(1H, 3H, 5H, 7H)-dione (1.80 g, 80%). Without further purification, the crude product was used directly in the next step.

LC-MS (Method A), (ES+) 171, RT=1.66 min.

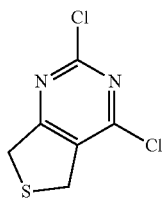

Step (v)

To thieno[3,4-d]pyrimidine-2,4-(1H, 3H, 5H, 7H)-dione (1.6 g, 9.41 mmol) was suspended in 4.0 mL of phenylphosphonyl dichloride and the suspension heated overnight at 135° C., then for 1 hour at 165° C. The resulting reaction mixture was cooled down and poured into ice-water. The aqueous layer was extracted with ethyl acetate. The organic layers were combined, washed with saturated NaHCO$_3$ solution and brine, dried over anhydrous Na$_2$SO$_4$ and evaporated. The crude product was then purified by column chromatography on silica gel (eluent: PE/EA=20/1-10/1) to give 2,4-dichloro-5,7-dihydrothieno[3,4-d]pyrimidine as a light yellow solid (1.6 g, 83%).

LC-MS (Method A), (ES+) 207/209, RT=4.96 min.

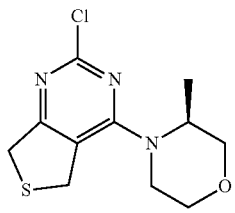 [SMILES: C[C@H]1COCCN1c1nc(Cl)nc2c1CSC2]

Step (vi)

To a solution of 2,4-dichloro-5,7-dihydrothieno[3,4-d]pyrimidine (300 mg, 1.45 mmol) and Et$_3$N (294 mg, 2.9 mmol) in DMF (5.0 mL) at 0° C. was added 3-(S)-methylmorpholine (161 mg, 1.59 mmol) dropwise. After the addition was complete, the mixture was stirred overnight at rt. The solvent was removed under vacuum to give a residue which was partitioned between water and ethyl acetate. The organic layer was washed with brine, dried and concentrated to give the crude product which was purified by preparative TLC (Eluent: petroleum ether/ethyl acetate=2/1) to provide 2-chloro-5,7-dihydro-4-((S)-3-methylmorpholino)thieno[3,4-d]pyrimidine as a light yellow solid (283 mg, 72%).

LC-MS (Method A), (ES+) 272, RT=5.00 min.

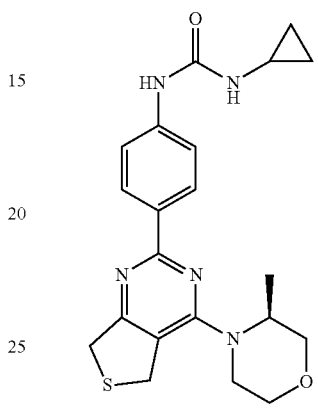

Step (vii)

To a solution of 2-chloro-5,7-dihydro-4-((S)-3-methylmorpholino)thieno[3,4-d]pyrimidine (100 mg, 0.37 mmol) in DME/H$_2$O (4:1, 10 mL) was added 1-cyclopropyl-3-(4-(4,4,5,5-tetramethyl-1,3,2-dioxaborolan-2-yl)phenyl)urea (124 mg, 0.41 mmol), and Na$_2$CO$_3$ (118 mg, 1.11 mmol) followed by addition of PdCl$_2$(dppf) (15 mg, 0.02 mmol). The resulting mixture was heated to 70° C. and stirred overnight under nitrogen. The solvent was removed under reduced pressure to give a residue which was partitioned between ethyl acetate and water. The organic layer was washed with brine dried (Na$_2$SO$_4$) and concentrated to give a crude product which was purified by preparative TLC (DCM/MeOH=20/1) to give the desired product, as a yellow solid (20 mg, 13%).

$^1$H NMR (d$_4$-Methanol) δ 8.24 (d, 2H), 7.51 (d, 2H), 4.69 (s, 1H), 4.60-4.58 (m, 1H), 4.37-4.35 (m, 1H), 4.24-4.17 (m, 3H), 4.03-3.99 (m, 1H), 3.80 (s, 2H), 3.70-3.65 (m, 1H), 3.55-3.48 (m, 1H), 2.64-2.60 (m, 1H), 1.40 (d, 3H), 0.79-0.77 (m, 2H), 0.55-0.54 (m, 2H).

LC-MS (Method A), (ES+) 412, RT=4.90 min.

Example 2

(S)-1-cyclopropyl-3-(4-(4-(3-methylmorpholino)-6,6-dioxido-5,7-dihydrothieno[3,4-d]pyrimidin-2-yl)phenyl)urea

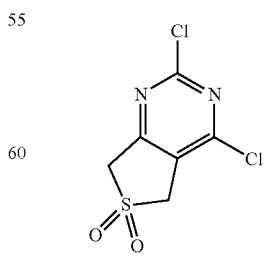

Step (i)

To a solution of 2,4-dichloro-5,7-dihydrothieno[3,4-d]pyrimidine (400 mg, 1.93 mmol) (Example 1, Step v) in CH$_2$Cl$_2$ (5 mL) was added m-CPBA (830 mg, 4.83 mmol) portionwise. The reaction mixture was stirred at rt overnight. The resulting mixture was washed with saturated NaHSO$_3$ and saturated Na$_2$CO$_3$, extracted with CH$_2$Cl$_2$, dried over anhydrous Na$_2$SO$_4$, and evaporated. The residue was then purified by column chromatography on silica gel (eluent: petroleum ether/ethyl acetate=2/1) to provide 2,4-dichloro-5,7-dihydrothieno[3,4-d]pyrimidine 6,6-dioxide as a white solid (260 mg, 57%).

LC-MS (Method A), (ES+) 239/241, RT=4.04 min.

Step (ii)

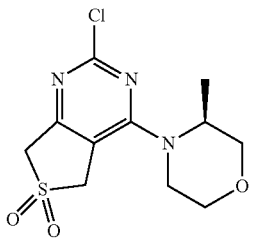 [SMILES: C[C@H]1COCCN1c1nc(Cl)nc2c1CS(=O)(=O)C2]

To a solution of 2,4-dichloro-5,7-dihydrothieno[3,4-d]pyrimidine 6,6-dioxide (120 mg, 0.5 mmol) and Et$_3$N (101 mg, 1.0 mmol) in DMF (5.0 mL) at 0° C. was added a mixture of(S)-3-methylmorpholine (51 mg, 0.5 mmol) dropwise. After the addition was complete, the mixture was stirred overnight at rt. The solvent was removed under vacuum to give a residue which was partitioned between water and ethyl acetate. The organic layer was washed with brine, dried (Na$_2$SO$_4$) and concentrated to give the product which was purified by preparative TLC (Eluent: petroleum ether/ethyl acetate=2/1) to provide 2-chloro-5,7-dihydro-4-((S)-3-methylmorpholino)thieno[3,4-d]pyrimidine 6,6-dioxide as a light yellow solid (100 mg, 66%).

LC-MS (Method A), (ES+) 304, RT=2.50 min.

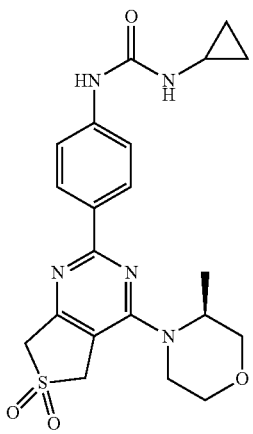 [SMILES: C[C@H]1COCCN1c1nc(-c2ccc(NC(=O)NC3CC3)cc2)nc2c1CS(=O)(=O)C2]

Step (iii)

To a solution of 2-chloro-5,7-dihydro-4-((S)-3-methylmorpholino)thieno[3,4-d]pyrimidine 6,6-dioxide (96 mg, 0.32 mmol) in DME/H$_2$O (4:1, 10 mL) was added 1-cyclopropyl-3-(4-(4,4,5,5-tetramethyl-1,3,2-dioxaborolan-2-yl)phenyl)urea (106 mg, 0.35 mmol), and Na$_2$CO$_3$ (102 mg, 0.96 mmol) followed by PdCl$_2$(dppf) (15 mg, 0.02 mmol). The resulting mixture was heated to 70° C. and stirred overnight under nitrogen. The solvent was removed under vacuum to give a residue which was partitioned between ethyl acetate and water. The organic layer was separated, dried (Na$_2$SO$_4$) and the solvent removed to give crude product which was purified by preparative TLC (DCM/MeOH=20/1) to give the desired product as a yellow solid (15 mg, 11%).

$^1$H NMR (d$_6$-DMSO) 68.66 (s, 1H) 8.20 (d, 2H), 7.53 (d, 2H), 6.52 (s, 1H), 4.75-4.44 (m, 5H), 3.98-3.93 (m, 2H), 3.66 (s, 2H), 3.54-3.40 (m, 2H), 2.50 (m, 1H, covered by DMSO), 1.29 (d, 3H), 0.66-0.64 (m, 2H), 0.43-0.39 (m, 2H).

LC-MS (Method A), (ES+) 444, RT=4.64 min.

Example 3

(S)-1-cyclopropyl-3-(4-(4-(3-methylmorpholino)-7,8-dihydro-5H-thiopyrano[4,3-d]pyrimidin-2-yl)phenyl)urea

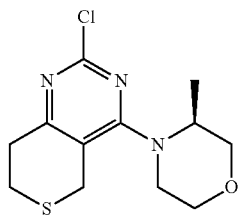 [SMILES: C[C@H]1COCCN1c1nc(Cl)nc2c1CSCC2]

Step (i)

To a solution of 2,4-dichloro-7,8-dihydro-5H-thiopyrano[4,3-d]pyrimidine (200 mg, 0.9 mmol), and Et$_3$N (182 mg, 1.8 mmol) in DMF (3 mL) at 0° C. was added 3-(S)-methylmorpholine (100 mg, 0.99 mmol). The resultant mixture was stirred at rt overnight. The solvent was removed under vacuum to give a residue which was partitioned between water and ethyl acetate. The organic layer was washed with brine dried and concentrated to give the product which was purified by preparative TLC (petroleum ether/ethyl acetate=2/1) to produce (S)-2-chloro-4-(3-methylmorpholino)-7,8-dihydro-5H-thiopyrano[4,3-d]pyrimidine (150 mg, 58%).

LC-MS (Method A), (ES+) 286, RT=4.75 min.

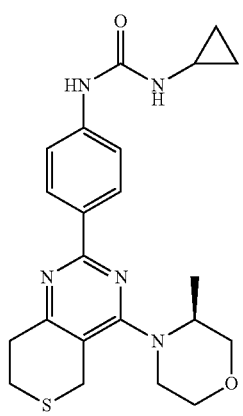 [SMILES: C[C@H]1COCCN1c1nc(-c2ccc(NC(=O)NC3CC3)cc2)nc2c1CSCC2]

Step (ii)

To a solution of (S)-2-chloro-4-(3-methylmorpholino)-7,8-dihydro-5H-thiopyrano[4,3-d]pyrimidine (100 mg, 0.35 mmol) in DME/H$_2$O (4:1, 10 mL) was added 1-cyclopropyl-3-(4-(4,4,5,5-tetramethyl-1,3,2-dioxaborolan-2-yl)phenyl)urea (116 mg, 0.38 mmol) and Na$_2$CO$_3$ (111 mg, 1.05 mmol) followed by PdCl$_2$(dppf) (15 mg, 0.02 mmol). The resulting mixture was stirred overnight at 70° C. under nitrogen. The solvent was removed under vacuum to give a residue which was partitioned between ethyl acetate and water. The organic layer was separated, dried over Na$_2$SO$_4$ filtered and evaporated to give the crude product which was purified by preparative TLC (DCM/MeOH=20/1) to give the desired product as a yellow solid (40 mg, 27%).

$^1$H NMR (CDCl3)8.37 (d, 2H), 7.53 (d, 2H), 7.12 (s, 1H), 5.09 (s, 1H), 3.93-3.75 (m, 4H), 3.67-3.58 (m, 3H), 3.52-3.40 (m, 1H), 3.35-3.32 (m, 1H), 3.20 (t, 2H), 3.03 (t, 2H), 2.66-2.63 (m, 1H), 1.30-1.27 (m, 3H), 0.89-0.87 (m, 2H), 0.72-0.68 (m, 2H).

LC-MS (Method A), (ES+) 426, RT=4.50 min.

Example 4

(S)-1-cyclopropyl-3-(4-(4-(3-methylmorpholino)-6,6-dioxido-7,8-dihydro-5H-thiopyrano[4,3-d]pyrimidin-2-yl)phenyl)urea

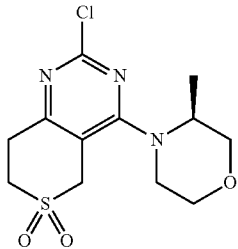 [SMILES: C[C@H]1COCCN1c1nc(Cl)nc2c1CS(=O)(=O)CC2]

Step (i)

Using a method analogous to example 2 step (ii) starting with 2,4-dichloro-7,8-dihydro-5H-thiopyrano[4,3-d]pyrimidine 6,6 dioxide, (S)-2-chloro-4-(3-methylmorpholino)-7,8-dihydro-5H-thiopyrano[4,3-d]pyrimidine 6,6 dioxide was synthesised.

LC-MS (Method A), (ES+) 318/320, RT=4.43 min.

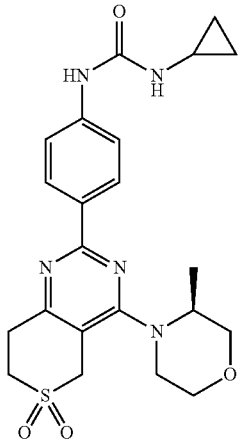 [SMILES: C[C@H]1COCCN1c1nc(-c2ccc(NC(=O)NC3CC3)cc2)nc2c1CS(=O)(=O)CC2]

Step (ii)

To a solution of (S)-2-chloro-4-(3-methylmorpholino)-7,8-dihydro-5H-thiopyrano[4,3-d]pyrimidine 6,6 dioxide (160 mg, 0.5 mmol) in DME/H$_2$O (4:1, 10 mL) were added 1-cyclopropyl-3-(4-(4,4,5,5-tetramethyl-1,3,2-dioxaborolan-2-yl)phenyl)urea (167 mg, 0.55 mmol) and Na$_2$CO$_3$ (159 mg, 1.5 mmol) followed by PdCl$_2$(dppf) (20 mg, 0.025 mmol).

The resulting mixture was heated to 70° C. and stirred overnight under nitrogen. The solvent was removed under vacuum to give a residue which was partitioned between ethyl acetate and water. The organic layer was separated, dried over Na$_2$SO$_4$ filtered and the solvent removed to give a crude product which was purified by preparative TLC (DCM/MeOH=20/1) to give the desired product as a yellow solid (36 mg, 16%).

$^1$H NMR (CDCl$_3$) 8.61 (s, 1H), 8.22 (d, 2H), 7.53 (d, 2H), 6.48 (s, 1H), 4.41-4.37 (m, 1H), 4.27-4.23 (m, 1H), 3.87-3.27 (m, 10H), 2.60-2.54 (m, 1H), 1.20 (d, 3H), 0.65-0.63 (m, 2H), 0.43-0.40 (m, 2H).

LC-MS (Method A), (ES+) 458, RT=4.52 min.

Example 5

(S)-1-cyclopropyl-3-(4-(4-(3-methylmorpholino)-5,5-dioxido-6,7-dihydrothieno[3,2-d]pyrimidin-2-yl)phenyl)urea

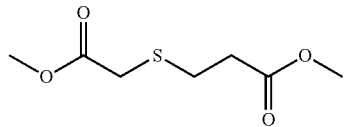

Step (i)

To a solution of methyl thioglycolate (91.0 mL, 1.0 mol) and piperidine (2 mL, 4.05 mmol) was added methyl acrylate (99.2 mL, 1.1 mol) dropwise. The reaction mixture was stirred at 50° C. for 2 h. The excess methyl acrylate and piperidine were then removed by distillation to afford methyl-3-(2-methoxy-2-oxoethylthio)-propanoate as a colourless oil (185 g, 96%). Without further purification, the crude product was used directly to the next step.

LC-MS (Method A), (ES+) 193, RT=4.29 min

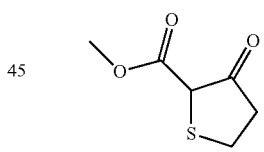

Step (ii)

Lithium metal (2.70 g, 390.15 mmol) was added to 500 mL of methanol in an ice-bath. Then at rt methyl 3-(2-methoxy-2-oxoethylthio)propanoate (50.0 g, 260.10 mmol) was added dropwise to the solution. The reaction mixture was stirred overnight. The resulting reaction mixture was evaporated to remove the solvent. The mixture was neutralized to pH=7-8 with 3N HCl and extracted with dichloromethane. The organic layers were combined, washed with brine, dried over anhydrous Na$_2$SO$_4$, filtered and evaporated. The crude residue obtained contained the target as the only isolable product. Purification by column chromatography on silica gel (eluent: PE/EA=20/1-5/1) provided methyl 3-oxo-tetrahydrothiophene-2-carboxylate as a colourless oil (18.0 g, 43%).

$^1$H NMR (CDCl$_3$) 4.04 (s, 1H), 3.78 (s, 3H), 3.34 (m, 1H), 3.06 (m, 1H), 2.83 (m, 1H), 2.69 (m, 1H).

LC-MS (Method A), (ES+) 183, RT=4.15 min.

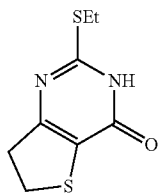

Step (iii)

To a solution of S-ethyl isothiouronium bromide (6.06 g, 32.7 mmol) in water (60 mL) was added sodium carbonate (3.64 g, 34.33 mmol) and methyl 3-oxo-tetrahydrothiophene-2-carboxylate (5.00 g, 31.20 mmol) dropwise. The mixture was stirred in the dark for 3 days. The solid precipitate in the resulting mixture was collected by filtration, washed with water, ether and ethyl acetate, and then dried under vacuum to obtain 2-(ethylthio)-6,7-dihydrothieno[3,2-d]pyrimidin-4 (3H)-one as a white solid, (2.8 g, 42.4%). Without further purification, the crude product was used directly in the next step.

LC-MS (Method A), (ES+) 215, RT=4.51 min.

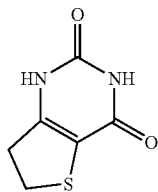 [SMILES: O=c1[nH]c2c(c(=O)[nH]1)SCC2]

Step (iv)

To a suspension of 2-(ethylthio)-6,7-dihydrothieno[3,2-d]pyrimidin-4(3H)-one (2.80 g, 13.06 mmol) in water (2.0 mL) was added 2.0 mL of conc. HCl and 4.0 mL of AcOH. The mixture was heated at 110° C. overnight. The reaction was cooled and the solid that formed collected by filtration washed with water and methanol, and dried to afford a white solid, 6,7-dihydrothieno[3,2-d]pyrimidine-2,4(1H,3H)-dione, (1.80 g, 82%). Without further purification, the crude product was used directly to the next step.

LC-MS (Method A), (ES+) 171, RT=4.21 min

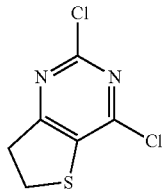

Step (v)

6,7-dihydrothieno[3,2-d]pyrimidine-2,4(1H,3H)-dione (1.8 g, 10.57 mmol) was suspended in 4.0 mL of phenylphosphonyl dichloride. The suspension was heated to 130-140° C. and stirred for 6 h. The resulting reaction mixture was cooled down and poured into 10.0 ml of ice-water. The mixture was extracted with ethyl acetate, the organic layers were combined, washed with saturated NaHCO₃ and brine, dried over anhydrous Na₂SO₄, filtered and evaporated. The crude product was then purified by column chromatography on silica gel (eluent: PE/EA=20:1-10/1) to provide 2,4-dichloro-6,7-dihydrothieno[3,2-d]pyrimidine an off-white solid (1.0 g, 46%).

LC-MS (Method A), (ES+) 207/209, RT=4.68 min

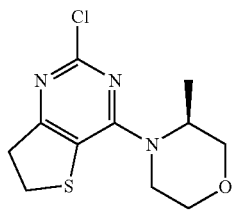 [SMILES: C[C@H]1COCCN1c1nc(Cl)nc2c1SCC2]

Step (vi)

To a solution of 2,4-dichloro-6,7-dihydrothieno[3,2-d]pyrimidine (200.0 mg, 0.96 mmol) and Et₃N (195.5 mg, 1.93 mmol) in DMF (2.0 mL) at 0° C. was added (S)-3-methylmorpholine (97.7 mg) dropwise. The mixture was stirred overnight at rt then was partitioned between H₂O and ethyl acetate. The aqueous layer was extracted with ethyl acetate and the combined organic layers washed with brine, dried over anhydrous Na₂SO₄, filtered, evaporated and then the crude product which was purified by column chromatography on silica gel (eluent: PE/EA=20:1-2/1) to provide (S)-2-chloro-4-(3-methylmorpholino)-6,7-dihydrothieno[3,2-d]pyrimidine as a light yellow solid (120 mg, 46%).

LC-MS (Method A), (ES+) 272/274, RT=4.88 min.

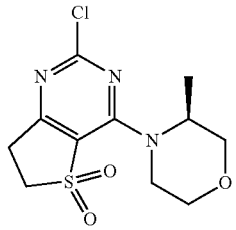 [SMILES: C[C@H]1COCCN1c1nc(Cl)nc2c1S(=O)(=O)CC2]

Step (vii)

(S)-2-chloro-4-(3-methylmorpholino)-6,7-dihydrothieno[3,2-d]pyrimidine (120 mg, 0.44 mmol) was dissolved in 4.0 mL of dichloromethane. To the solution was added m-CPBA (190.4 mg, 1.10 mmol) portion wise. The reaction mixture was stirred at rt for 5 h. The resulting mixture was diluted with dichloromethane, washed with saturated NaHSO₃ and saturated Na₂CO₃. The organic layer was dried over anhydrous Na₂SO₄, filtered and evaporated. The residue was then purified by prep.TLC (eluent: petroleum ether/ethyl acetate, 2/1) to provide 2-chloro-4-[(3S)-3-methylmorpholin-4-yl]-6,7-dihydrothieno[3,2-d]pyrimidine 5,5-dioxide as a white solid, (50.0 mg, 37%).

LC-MS (Method A), (ES+) 304/306, RT=3.44 min.

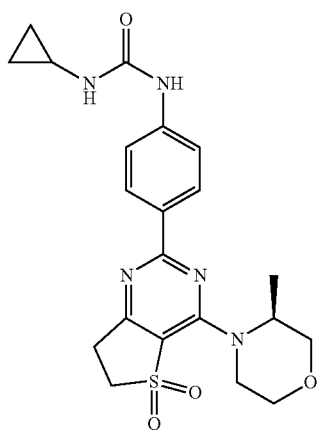 [SMILES: C[C@H]1COCCN1c1nc(-c2ccc(NC(=O)NC3CC3)cc2)nc2c1S(=O)(=O)CC2]

Step (viii)

To solution of 2-chloro-4-[(3S)-3-methylmorpholin-4-yl]-6,7-dihydrothieno[3,2-d]pyrimidine 5,5-dioxide (50 mg, 0.16 mmol), in 2.0 mL of DME/H$_2$O (4/1, v/v) was added 1-cyclopropyl-3-(4-(4,4,5,5-tetramethyl-1,3,2-dioxaborolan-2-yl)phenyl)urea (59.7 mg, 0.20 mmol) and Na$_2$CO$_3$ (52.3 mg, 0.49 mmol). The mixture was degassed twice, and then catalytic amount of Pd(dppf)Cl$_2$ (10 mg, 0.013 mmol) was added. The mixture was heated to 80° C. and stirred for 3 h under nitrogen. The resulting mixture was then cooled and diluted with EtOAc and H$_2$O the aqueous layer was extracted with ethyl acetate and the combined organic layers were combined, washed by brine, dried over anhydrous Na$_2$SO$_4$, filtered, and then evaporated to give the crude which was purified by column chromatography on silica gel (eluent: CH$_2$Cl$_2$/ethyl acetate=30/1~1/1) to provide 1-cyclopropyl-3-[4-[4-[(3S)-3-methylmorpholin-4-yl]-5,5-dioxo-6,7-dihydrothieno[3,2-d]pyrimidin-2-yl]phenyl]urea as a white solid, (30.0 mg, 41%).

$^1$H NMR (d6-DMSO):8.68 (s, 1H), 8.24 (d, 2H), 7.54(d, 2H),6.51 (s, 1H), 4.90 (s, 1H), 4.39 (s, 1H), 4.01-4.02 (d, 1H), 3.80(d, 1H), 3.69-3.66 (m, 3H), 3.53-3.51 (d, 2H), 2.56-2.51 (m, 1H), 1.35 (d, 3H), 1.24 (s, 1H),0.66-0.64 (m, 2H), 0.42 (m, 2H).

LC-MS (Method A), (ES+) 444, RT=3.32 min.

Example 6

1-cyclopropyl-3-(4-(5-methyl-4-((S)-3-methylmorpholino)-6,6-dioxido-5,7-dihydrothieno[3,4-d]pyrimidin-2-yl)phenyl)urea

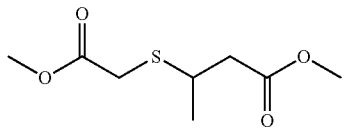

Step (i)

To a mixture of methyl thioglycolate (21.2 g, 199.7 mmol) and piperidine (0.5 mL, 5.06 mmol) at 0° C. was added methyl crotonate (25.0 g, 249.70 mmol) dropwise. Additional piperidine (0.3 mL, 3.04 mmol) was added in two portions after 10 mins. The mixture was then stirred at rt overnight. The excess methyl crotonate and piperidne were removed by distillation to leave methyl 3-(2-methoxy-2-oxoethylthio)butanoate as a light yellow oil, (40 g, 97%). Without further purification, the crude product was used directly to the next step.

LC-MS (Method A), (ES+) 207, RT=4.78 min

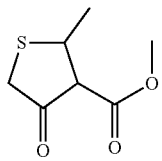

Step (ii)

To a suspension of sodium methoxide (5.89 g, 109.2 mmol) in toluene (150 mL) was added methyl 3-(2-methoxy-2-oxoethylthio)butanoate (150 g, 72.8 mmol) dropwise. The resultant mixture was heated to reflux and stirred overnight. The resulting reaction mixture was cooled then poured into a mixture of 10.0 mL of acetic acid in 150.0 g of crushed ice. The solution was made basic (pH=8-9) by addition of saturated Na$_2$CO$_3$ and the resulting mixture extracted with ethyl acetate. The combined organic layers were then combined and washed with brine, dried over anhydrous Na$_2$SO$_4$, filtered, evaporated, and the residue purified by column chromatography (eluent: petroleum ether/ethyl acetate=20/1-5/1) to provide methyl 2-methyl-4-oxo-tetrahydrothiophene-3-carboxylate as a colorless oil (4.0 g, 32%).

LC-MS (Method A), (ES+) 175, RT=4.40 min

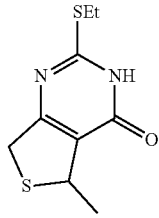

Step (iii)

To a solution of S-ethyl isothiouronium bromide (5.09 g, 22.7 mmol) in water (35.0 mL) were added, sodium carbonate (3.65 g, 34.4 mmol) and methyl 2-methyl-4-oxo-tetrahydrothiophene-3-carboxylate (4.00 g, 22.9 mmol) portionwise. The resultant mixture was stirred in the dark for 3 days and the solid which precipitated from the reaction was collected by filtration, washed with water, ether and ethyl acetate, then dried under vacuum to obtain 2-(ethylthio)-5-methylthieno[3,4-d]pyrimidin-4(3H,5H,7H)-one as a white solid (4.0 g, 76%). Without further purification, the crude product was used directly to the next step.

LC-MS (Method A), (ES+) 229, RT=4.90 min

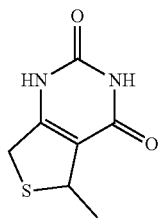

Step (iv)

2-(ethylthio)-5-methylthieno[3,4-d]pyrimidin-4(3H,5H,7H)-one (4.0 g, 17.5 mmol), was suspended in 4.0 mL of conc. HCl and 6.0 mL of glacial acetic acid and the suspension heated at reflux overnight. The mixture was cooled and the precipitated solid collected by filtration, washed with water, and dried to provide 5-methylthieno[3,4-d]pyrimidine-2,4(1H,3H,5H,7H)-dione as a white solid (3.20 g, 100%).

$^1$H NMR (d$_6$-DMSO): 11.19 (s, 1H), 11.04 (s, 1H), 4.36-4.34 (m, 1H), 4.07-4.02 (dd, J=16, 4.4 Hz, 1H), 3.87-3.83 (dd, J=16, 1.2 Hz, 1H), 1.48-1.48 (d, J=6.4 Hz, 3H).

LC-MS (Method A), (ES+) 185, RT=4.11 min

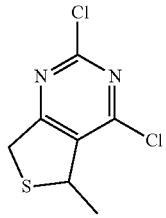

Step (v)

5-methylthieno[3,4-d]pyrimidine-2,4(1H,3H,5H,7H)-dione (3.2 g, 17.2 mmol) was suspended in phenylphosphonyl dichloride (8.0 mL) then the suspension heated to 130-140° C. and stirred for 6 h. The resulting reaction mixture was cooled and poured into 30 mL of ice-water. The mixture was extracted with ethyl acetate and the combined organic layers were washed with saturated NaHCO$_3$, brine, dried over anhydrous Na$_2$SO$_4$, filtered and evaporated. The crude product was then purified by column chromatography on silica gel (eluent: petroleum ether/ethyl acetate=20/1-10/1) to provide 2,4-dichloro-5-methyl-5,7-dihydrothieno[3,4-d]pyrimidine as a light yellow solid (2.0 g, 53%).

$^1$H NMR (CDCl$_3$): 4.66-4.64 (m, 1H), 4.47-4.42 (dd, J=2.8, 2.4 Hz, 1H), 4.19-4.14 (m, 1H), 1.71-1.69 (d, J=6.8 Hz, 3H).

LC-MS (Method A), (ES+) 221/223, RT=4.94 min

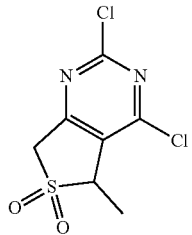

Step (vi)

2,4-dichloro-5-methyl-5,7-dihydrothieno[3,4-d]pyrimidine (1.0 g, 4.5 mmol) was dissolved in dichloromethane (10 mL). m-CPBA (2.3 g, 13.6 mmol) was added portionwise and the reaction stirred at rt overnight. The reaction was diluted with dichloromethane, and washed with saturated NaHSO$_3$ and saturated Na$_2$CO$_3$. The organic layer was dried with anhydrous Na$_2$SO$_4$, filtered and evaporated to provide a crude residue that was purified by column chromatography on silica gel (eluent: petroleum ether/ethyl acetate=2/1). The product, 2,4-dichloro-5-methyl-5,7-dihydrothieno[3,4-d]pyrimidine 6,6-dioxide, was obtained as a white solid (0.60 g, 53%).

LC-MS (Method A), (ES+) 253/255, RT=4.36 min

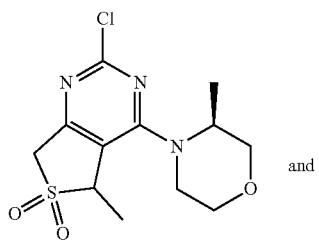

(A)

and (B)

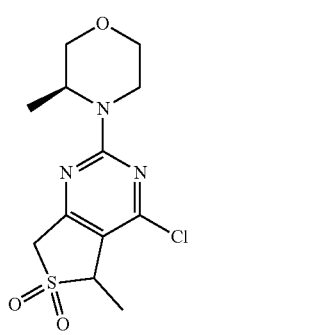

Step (vii)

To a solution of 2,4-dichloro-5-methyl-5,7-dihydrothieno[3,4-d]pyrimidine 6,6-dioxide (150.0 mg, 0.5926 mmol) and Et$_3$N (119.9 mg, 1.2 mmol) in DMF (2.0 mL) was added (S)-3-methylmorpholine (59.9 mg, 0.6 mmol) dropwise. The reaction mixture stirred overnight, then quenched by addition of H$_2$O and the resulting mixture extracted with ethyl acetate. The organic layers were combined, washed with brine, dried over anhydrous Na$_2$SO$_4$, filtered and evaporated. The crude product was purified by column chromatography on silica gel (eluent: petroleum ether/ethyl acetate=20:1-2/1) to provide 4-chloro-5-methyl-2-[(3S)-3-methylmorpholin-4-yl]-5,7-dihydrothieno[3,4-d]pyrimidine 6,6-dioxide (B) as a light yellow solid (50 mg, 13.5%). Further elution then provides 2-chloro-5-methyl-4-[(3S)-3-methylmorpholin-4-yl]-5,7-dihydrothieno[3,4-d]pyrimidine 6,6-dioxide (A) as an off-white soild (100 mg, 27%), A: $^1$H NMR (CDCl$_3$): 4.35-4.29 (m, 2H), 4.26-4.21 (m, 3H), 4.06-4.00 (m, 1H), 3.89-3.86 (m, 1H), 3.80 (s, 2H), 3.73-3.72 (m, 1H), 3.62-3.59 (m, 1H), 3.57-3.51 (m, 2H), 1.37-1.36 (d, J=7.8 Hz, 3H).

LC-MS (Method A), (ES+) 318/320, RT=4.51 min

B: $^1$H NMR (CDCl$_3$): 4.69-4.67 (m, 1H), 4.35-4.24 (m, 3H), 4.20-4.15 (m, 1H), 4.02-3.98 (m, 1H), 3.80-3.77 (m, 1H), 3.69-3.65 (m, 1H), 3.55-3.49 (m, 1H), 3.34-3.27 (m, 1H), 1.68-1.66 (d, J=7.2 Hz, 3H), 1.34-1.66 (d, J=6.8 Hz, 3H).

LC-MS (Method A), (ES+) 318/320, RT=4.73 min

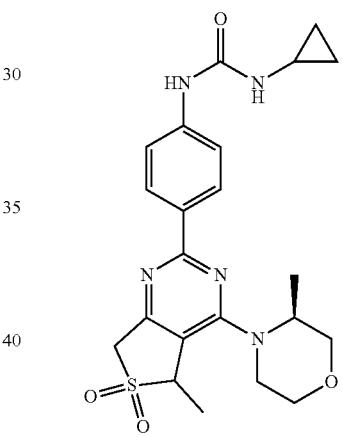

Step (viii)

To a solution of 2-chloro-5-methyl-4-[(3S)-3-methylmorpholin-4-yl]-5,7-dihydrothieno[3,4-d]pyrimidine 6,6-dioxide (100 mg, 0.3147 mmol) in DME/H$_2$O (2 mL, 4/1, v/v) were added 1-cyclopropyl-3-(4-(4,4,5,5-tetramethyl-1,3,2-dioxaborolan-2-yl)phenyl)urea (114.1 mg, 0.37 mmol) and sodium carbonate (100.1 mg, 0.94 mmol) The reaction was degassed twice and a catalytic amount of Pd(dppf)Cl$_2$ (10 mg, 0.013 mmol) was added to the suspension. The mixture was heated at 80° C. for 3 h under a nitrogen atmosphere. The resulting mixture was cooled and H$_2$O was added. The mixture was extracted with ethyl acetate and the combined organic layers washed with brine, dried over anhydrous Na$_2$SO$_4$, filtered, and then evaporated. The residue was purified by column chromatography on silica gel (eluent: CH$_2$Cl$_2$/ethyl acetate=20/1~5/1) and preparative HPLC to provide the product as a white solid (30.0 mg, 21%).

$^1$H NMR (CDCl$_3$):8.32-8.24 (m, 2H), 7.52 (d, 2H), 7.12 (s, 1H), 5.05 (s, 1H), 4.42-4.20 (m, 4H), 4.07-3.98 (m, 1H), 3.88-3.77 (m, 3H), 3.75-3.49 (m, 2H), 2.67-2.62 (m, 1H), 1.65-1.62 (m, 3H), 0.90-0.84 (m, 2H), 0.72-0.67 (m, 2H)

LC-MS (Method A), (ES+) 458, RT=3.47 min.

Example 7

1-cyclopropyl-3-(4-(7-methyl-4-((S)-3-methylmorpholino)-6,6-dioxido-5,7-dihydrothieno[3,4-d]pyrimidin-2-yl)phenyl)urea

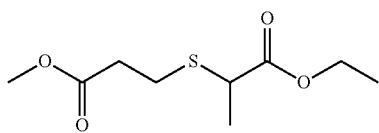

Step (i)

To a mixture of methyl 3-mercaptopropanoate (34.3 g, 0.29 mol), and ethyl 2-bromo propanoate (54.3 g, 0.30 mol) in THF (200 mL) was added NaH (60% dispersion in mineral oil, 12.76 g, 0.32 mol) slowly and the and the reaction stirred at rt overnight. The solvent was removed under reduced pressure and water was added. The mixture was extracted with DCM and the organic phase dried over $Na_2SO_4$ and concentrated to give the crude product methyl 3-(2-ethoxy-1-methyl-2-oxo-ethyl)sulfanylpropanoate (65 g, 100%), which was used in the next step directly.

LC-MS (Method A), (ES+) 221, RT=4.63 min.

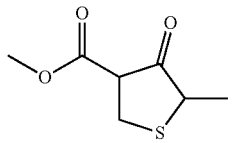

Step (ii)

To a solution of methyl 3-(2-ethoxy-1-methyl-2-oxo-ethyl)sulfanylpropanoate (2.2 g, 10 mmol) in methanol (15 mL) at 0° C. was added sodium methoxide (886 mg, 16.4 mmol). The reaction was warmed to rt and stirred for 3 h. The mixture was acidified with 1 N HCl to pH 2 and extracted with DCM. The organic phase was washed with water and brine, dried ($Na_2SO_4$), concentrated and purified by column chromatography, eluting with EtOAc in petroleum (3%-10%) to give methyl tetrahydro-5-methyl-4-oxothiophene-3-carboxylate as a colourless oil (0.85 g, 50% yield).

LC-MS (Method A), (ES+) 175, RT=4.30 min.

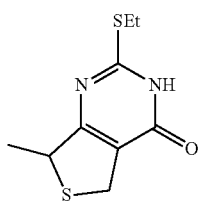

Step (iii)

To a solution of S-ethyl isothiouronium bromide (4.89 g, 26.4 mmol) in water (60 mL) was added, sodium carbonate (2.80 g, 26.4 mmol) and methyl tetrahydro-5-methyl-4-oxothiophene-3-carboxylate (4.60 g, 26.4 mmol) dropwise. The mixture was stirred overnight in the dark at rt. The solid that precipitated in the resulting mixture was collected by filtration, washed with water, diethyl ether, methanol and acetone, then the solid was dried under vacuum to obtain 2-(ethylthio)-7-methylthieno[3,4-d]pyrimidin-4(3H,5H,7H)-one as a white solid (3.96 g, 66%).

LC-MS (Method A), (ES+) 229, RT=3.10 min.

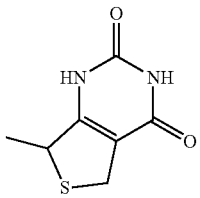

Step (iv)

To a suspension of 2-(ethylthio)-7-methylthieno[3,4-d]pyrimidin-4(3H,5H,7H)-one (3.96 g, 17.3 mmol) in water (20 mL) was added 2.0 mL of conc. HCl and 4.0 mL of AcOH. The mixture was heated to reflux overnight then cooled and the precipitated solid collected by filtration, washed with water and methanol, evaporated and dried to obtain 7-methylthieno[3,4-d]pyrimidine-2,4(1H,3H,5H,7H)-dione as a white solid (2.52 g, 80%). Without further purification, the crude product was used directly in the next step.

LC-MS (Method A), (ES+) 185, RT=2.58 min.

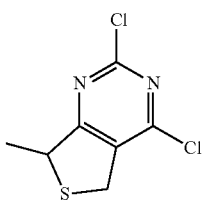

Step (v)

7-methylthieno[3,4-d]pyrimidine-2,4(1H,3H,5H,7H)-dione (2.52 g, 13.7 mmol) was suspended in $POCl_3$ (20 mL) and heated at reflux overnight. The solvent was removed under reduced pressure and the residue was poured into 10.0 ml of ice-water. The mixture was extracted with ethyl acetate (3×10.0 mL) and the combined organic layers washed with saturated $NaHCO_3$ and brine, dried over anhydrous $Na_2SO_4$, filtered and concentrated. The crude product was then purified through column chromatography on silica gel (eluting: PE/EA=20:1~10/1) to provide 2,4-dichloro-5,7-dihydro-7-methylthieno[3,4-d]pyrimidine an off-white solid (670 mg, 23%).

LC-MS (Method A), (ES+) 221/223, RT=3.32 min.

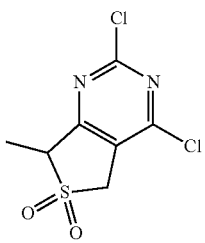

Step (vi)

To a solution of 2,4-dichloro-5,7-dihydro-7-methylthieno[3,4-d]pyrimidine (221 mg, 1.0 mmol) in DCM (10 mL) at 0° C. was added m-CPBA (432 mg, 2.5 mmol) in portions. The reaction was stirred at rt for 2 h then quenched by addition of saturated Na₂CO₃ solution. The mixture was extracted with DCM and the combined organic layers washed with water and brine, dried and concentrated to give the crude product, 2,4-dichloro-7-methyl-5,7-dihydrothieno[3,4-d]pyrimidine 6,6-dioxide as a white solid (230 mg, 92% yield). This material was used directly in the next step without further purification.

LC-MS (Method A), (ES+) 275 (M+Na), RT=2.73 min.

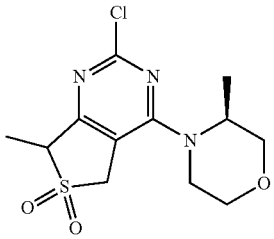 [SMILES: CC1c2nc(Cl)nc(N3CCOC[C@@H]3C)c2CS1(=O)=O]

Step (vii)

To a solution of 2,4-dichloro-7-methyl-5,7-dihydrothieno [3,4-d]pyrimidine 6,6-dioxide (160 mg, 0.63 mmol), and triethylamine (64 mg, 0.63 mmol) in DMF (3 mL) at 0° C. was added 3-(S)-methylmorpholine (57 mg, 0.57 mmol). The resultant mixture was stirred at rt for 2 h. The solvent was removed under vacuum and the residue obtained partitioned between water and ethyl acetate. The organic layer was dried (Na₂SO₄) and concentrated to give the product which was purified by preparative TLC (petroleum ether/ethyl acetate=2/1) to produce 2-chloro-7-methyl-4-[(3S)-3-methylmorpholin-4-yl]-5,7-dihydrothieno[3,4-d]pyrimidine 6,6-dioxide (72 mg, 36% yield).

LC-MS (Method A), (ES+) 318/320, RT=2.95 min.

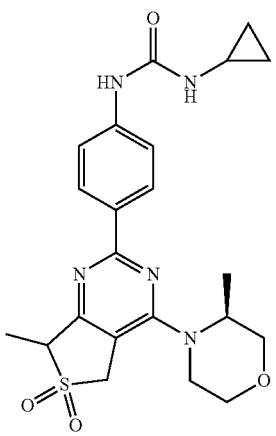 [SMILES: CC1c2nc(-c3ccc(NC(=O)NC4CC4)cc3)nc(N3CCOC[C@@H]3C)c2CS1(=O)=O]

Step (viii)

To a solution of 2-chloro-7-methyl-4-[(3S)-3-methylmorpholin-4-yl]-5,7-dihydrothieno[3,4-d]pyrimidine 6,6-dioxide (32 mg, 0.10 mmol) in DME/H₂O (4:1, 10 mL) was added 1-cyclopropyl-3-(4-(4,4,5,5-tetramethyl-1,3,2-dioxaborolan-2-yl)phenyl)urea (45 mg, 0.15 mmol) and Na₂CO₃ (32 mg, 0.30 mmol) followed by PdCl₂(dppf) (10 mg, 0.013 mmol). The resulting mixture was stirred overnight at 80° C. under nitrogen. The solvent was removed under vacuum to give a residue which was partitioned between ethyl acetate and water. The organic layer was separated, dried (Na₂SO₄), filtered and evaporated to provide the crude product which was purified by preparative TLC (DCM/MeOH=10/1) to give the desired product as a white solid (10 mg, 22%).

¹H NMR (d₆-DMSO) 9.30 (s, 1H), 8.20 (d, 2H), 7.52 (d, 2H), 7.00 (s, 1H), 4.75-4.35 (m, 4H), 4.02-3.85 (m, 2H), 3.73-3.42 (m, 4H), 2.57-2.49 (m, 1H partially under DMSO) 1.54 (d, 3H), 1.24 (d, 3H), 0.65-0.59 (m, 2H), 0.41-0.35 (m, 2H).

LC-MS (Method A), (ES+) 458, RT=3.06 min.

Example 8

(S)-1-cyclopropyl-3-(4-(4-(3-methylmorpholino)-7, 8-dihydro-6H-thiopyrano[3,2-d]pyrimidin-2-yl)phenyl)urea

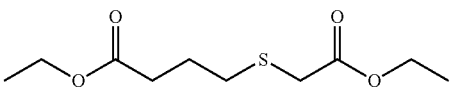

Step (i)

Sodium metal (4.3 g, 0.18 mol) was added cautiously in small portions to ethanol (150 mL). After the sodium completely dissolved, the mixture was cooled to 0° C. and ethyl 2-sulfanylacetate (21.9 g, 0.18 mol), was added. Ethyl 4-chlorobutanoate (27.4 g, 0.18 mol) was then added slowly and the resulting mixture stirred overnight at rt. The solid was filtered off, and then the filtrate concentrated under reduced pressure. The oil obtained was partitioned between water and ethyl acetate. The organic layer was collected, dried over anhydrous Na₂SO₄ and concentrated under vacuum to give the desired ethyl 4-((ethoxycarbonyl)methylthio)butanoate (40.2 g, 95%) as colorless oil. The crude material was used without further purification in the follow step.

LC-MS (Method A), (ES+) 235, RT=4.74 min.

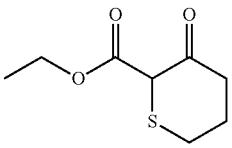

Step (ii)

Sodium metal (4.6 g, 0.2 mol) was added cautiously in portions to ethanol (150 mL). After the solid was consumed, the mixture was cooled to 0° C. and Ethyl 4-((ethoxycarbonyl)methylthio)butanoate (40.2 g, 0.17 mol) in toluene (80 mL) was added. The mixture was stirred at r.t for 3 hours, and then heated to 50° C. for another hour. The mixture was left at rt for 24 hours. The solvent was then removed under reduced pressure and the residue was partitioned between ethyl acetate and water. The organic layer was washed with brine, dried over anhydrous Na₂SO₄, and evaporated. The crude product was then purified by column chromatography on silica gel (eluent: petroleum ether/ethyl acetate=30/1) to give a mixture of ethyl tetrahydro-3-oxo-2H-thiopyran-2-carboxylate and methyl 3-oxotetrahydro-2H-thiopyran-4-carboxylate in a 10:1 ratio (4.8 g, 15%). This product was used in the next step without further purification.

LC-MS (Method A), (ES+) 189, RT=4.39 min.

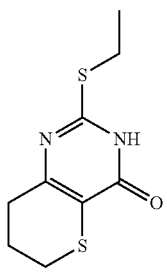

Step (iii)

To a solution of S-ethyl isothiouronium bromide (4.4 g, 24 mmol) in water (50 mL) was added, sodium carbonate (2.5 g, 24 mmol) and ethyl tetrahydro-3-oxo-2H-thiopyran-2-carboxylate (4.5 g, 24 mmol) dropwise. The mixture was stirred overnight in the dark at rt. The solid which precipitates from the reaction was collected by filtration, washed with water, diethyl ether, methanol and acetone. The solid was dried under vacuum to obtain 2-(ethylthio)-7,8-dihydro-3H-thiopyrano[3,2-d]pyrimidin-4(6H)-one as a white solid (4.5 g, 82%). Without further purification, the crude product was used directly to the next step.

LC-MS (Method A), (ES+) 229, RT=4.60 min.

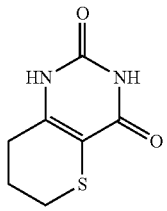

Step (iv)

To a suspension of 2-(ethylthio)-7,8-dihydro-3H-thiopyrano[3,2-d]pyrimidin-4(6H)-one (4.5 g, 19.7 mmol) in water (20 mL) was added 3.0 mL of conc. HCl and 6.0 mL of AcOH. The mixture was heated to reflux and stirred overnight. The reaction was cooled and the solid that formed was collected by filtration, washed with water and methanol, evaporated and dried to obtain 7,8-dihydro-1H-thiopyrano[3,2-d]pyrimidine-2,4(3H,6H)-dione as a white solid (2.6 g, 72%). Without further purification, the crude product was used directly in the next step.

LC-MS (Method A), (ES+) 185, RT=2.17 min.

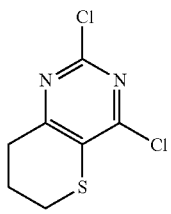 [SMILES: Clc1nc(Cl)c2c(n1)CCCS2]

Step (v)

To 7,8-dihydro-1H-thiopyrano[3,2-d]pyrimidine-2,4(3H,6H)-dione (2.6 g, 14.13 mmol) was added 6.0 mL of phosphoryl trichloride and the suspension heated overnight at 135° C. and then for 1 hour at 165° C. The resulting reaction mixture was cooled down and poured into ice-water. The aqueous layer was extracted with ethyl acetate and the combined organic layers washed with saturated NaHCO$_3$, brine, dried over anhydrous Na$_2$SO$_4$, and evaporated. The crude product was then purified by column chromatography on silica gel (eluent: petroleum ether/ethyl acetate=20/1) to get 2,4-dichloro-7,8-dihydro-6H-thiopyrano[3,2-d]pyrimidine as a light yellow solid (2.7 g, 87%). The regioisomeric product arising from methyl 3-oxotetrahydro-2H-thiopyran-4-carboxylate (Example 8, Step ii) was not detected and was assumed lost in purification.

LC-MS (Method A), (ES+) 221, RT=2.88 min.

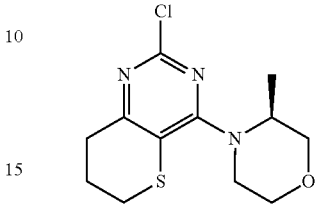

Step (vi)

To a solution of 2,4-dichloro-7,8-dihydro-6H-thiopyrano[3,2-d]pyrimidine (500 mg, 2.26 mmol) and Et$_3$N (457 mg, 4.52 mmol) in DMF (5.0 mL) at 0° C. was added 3-(S)-methylmorpholine (252 mg, 2.49 mmol) dropwise. The reaction was stirred overnight at rt, then the solvent removed under vacuum to give a residue which was partitioned between water and ethyl acetate. The organic layer was separated, dried and concentrated to give the crude product which was purified by column chromatography on silica gel (eluent: petroleum ether/ethyl acetate=10/1) to give 2-chloro-7,8-dihydro-4-((S)-3-methylmorpholino)-6H-thiopyrano[3,2-d]pyrimidine (380 mg, 87%) as a light yellow solid.

LC-MS (Method A), (ES+) 286, RT=3.69 min.

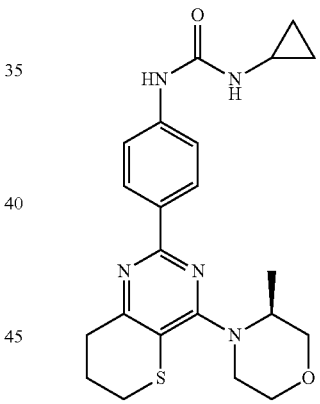

Step (vii)

To a solution of 2-chloro-7,8-dihydro-4-((S)-3-methylmorpholino)-6H-thiopyrano[3,2-d]pyrimidine (150 mg, 0.53 mmol) in DME/H$_2$O (4:1, 10 mL) was added 1-cyclopropyl-3-(4-(4,4,5,5-tetramethyl-1,3,2-dioxaborolan-2-yl)phenyl) urea (175 mg, 0.58 mmol) and Na$_2$CO$_3$ (170 mg, 1.60 mmol) followed by PdCl$_2$(dppf) (15 mg, 0.02 mmol). The resulting mixture was stirred overnight at 70° C. under nitrogen. The solvent was removed under vacuum to give a residue which was partitioned between ethyl acetate and water. The organic layer was separated and dried over anhydrous Na$_2$SO$_4$. The solvent was removed to give crude material which was purified by preparative TLC (DCM/MeOH=20/1) to give the desired product as a white solid (180 mg, 80%).

$^1$H NMR (CDCl$_3$) δ8.34 (d, 2H), 7.52 (d, 2H), 7.10 (s, 1H), 5.08 (s, 1H), 4.20-4.14 (m, 1H), 3.92-3.84 (m, 3H), 3.65-3.58 (m, 3H), 3.04-2.98 (m, 4H), 2.66-2.63 (m, 1H), 2.30-2.24 (qu, 2H), 1.30 (d, 3H), 0.88-0.86 (m, 2H), 0.71-0.68 (m, 2H).

LC-MS (Method A), (ES+) 426, RT=3.29 min.

Examples 9 and 10

1-cyclopropyl-3-(4-((R)-5-methyl-4-((S)-3-methyl-morpholino)-6,6-dioxido-5,7-dihydrothieno[3,4-d]pyrimidin-2-yl)phenyl)urea; and 1-cyclopropyl-3-(4-((S)-5-methyl-4-((S)-3-methylmorpholino)-6,6-dioxido-5,7-dihydrothieno[3,4-d]pyrimidin-2-yl)phenyl)urea

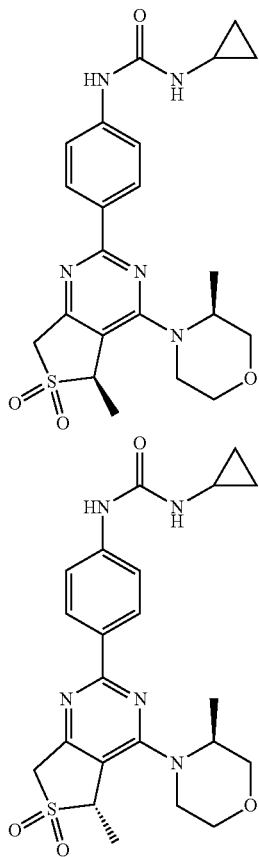

The compound of example 6(1-cyclopropyl-3-(4-(5-methyl-4-((S)-3-methylmorpholino)-6,6-dioxido-5,7-dihydrothieno[3,4-d]pyrimidin-2-yl)phenyl)urea) is a mixture of diastereoisomers. The individual diastereoisomers were separated under the following super critical fluid chromatography conditions.

Instrument: MG II preparative SFC

Column: ChiralPak AS-H, 250×30 mm I.D.

Mobile phase: A for $CO_2$ and B for Ethanol

Gradient: B 40%

Flow rate: 50 mL/min

Back pressure: 100 bar

Column temperature: 38° C.

Wavelength: 220 nm

Cycletime: 14 min

Sample preparation: Compound was dissolved in ethanol to ~5 mg/ml

Injection: 4.7 ml per injection.

Work up: After separation, the fractions were dried off via rotary evaporator at bath temperature 40° C. to get the desired diastereoisomers.

From 275 mg of diastereomer mixture

Example 9 the first eluting diastereomer (92 mg)

$^1$H NMR (DMSO) δ 8.65 (s, 1H), 8.18 (d, 2H), 7.52 (d, 2H), 6.53 (s, 1H), 4.77 (q, 1H), 4.71 (d, 1H), 4.61-4.51 (m, 1H), 4.40 (d, 1H), 3.99-3.83 (m, 2H), 3.81-3.65 (m, 2H), 3.57 (ddd, 7.9 Hz, 1H), 3.46-3.38 (m, 1H), 2.56 (m, 1H), 1.50 (d, 3H), 1.35 (d, 3H), 0.65 (ddd, 2H), 0.40 (ddd, 2H).

Example 10 the second eluting diastereomer (145 mg)

$^1$H NMR (DMSO) δ 8.70 (s, 1H), 8.24 (d, 2H), 7.57 (d, 2H), 6.58 (d, 1H), 4.77 (q, 1H), 4.73 (d, 1H), 4.54 (d, 1H), 4.50-4.41 (m, 1H), 4.08-3.93 (m, 2H), 3.85-3.73 (m, 2H), 3.67-3.55 (m, 1H), 3.55-3.43 (m, 1H), 2.64-2.58 (m, 1H), 1.54 (d, 3H), 1.27 (d, 3H), 0.70 (ddd, 2H), 0.47 (ddd, 2H).

The following compounds were synthesized by procedures analogous to those described above:

TABLE 9

| Structure | Name | Example Number | LCMS Method | ES+ | RT (mins) | Purity (%) |
|---|---|---|---|---|---|---|
| 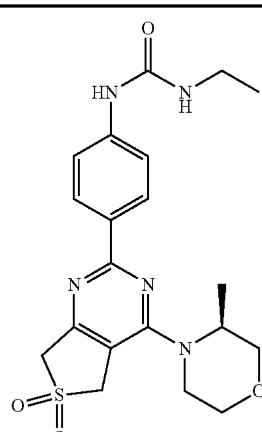 | (S)-1-ethyl-3-(4-(4-(3-methylmorpholino)-6,6-dioxido-5,7-dihydrothieno[3,4-d]pyrimidin-2-yl)phenyl)urea | Ex 11 | B | 432 | 2.10 | 90-95% |

TABLE 9-continued

| Structure | Name | Example Number | LCMS Method | ES+ | RT (mins) | Purity (%) |
|---|---|---|---|---|---|---|
| 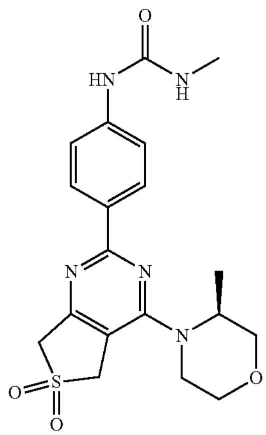 [SMILES: CNC(=O)Nc1ccc(-c2nc3c(c(N4CCOC[C@@H]4C)n2)CS(=O)(=O)C3)cc1] | (S)-1-methyl-3-(4-(4-(3-methylmorpholino)-6,6-dioxido-5,7-dihydrothieno[3,4-d]pyrimidin-2-yl)phenyl)urea | Ex 12 | B | 418 | 2.00 | 90-95% |
| 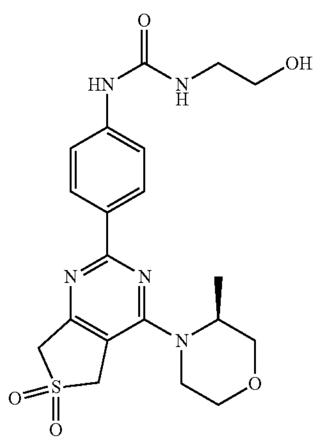 [SMILES: C[C@H]1COCCN1c1nc(-c2ccc(NC(=O)NCCO)cc2)nc2c1CS(=O)(=O)C2] | (S)-1-(2-hydroxyethyl)-3-(4-(4-(3-methylmorpholino)-6,6-dioxido-5,7-dihydrothieno[3,4-d]pyrimidin-2-yl)phenyl)urea | Ex 13 | B | 448 | 1.93 | 90-95% |
| 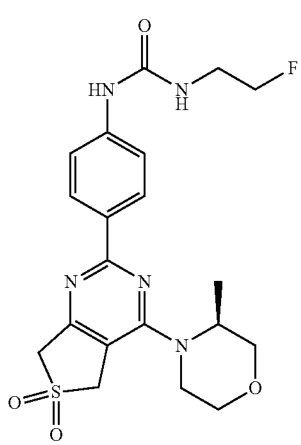 [SMILES: C[C@H]1COCCN1c1nc(-c2ccc(NC(=O)NCCF)cc2)nc2c1CS(=O)(=O)C2] | (S)-1-(2-fluoroethyl)-3-(4-(4-(3-methylmorpholino)-6,6-dioxido-5,7-dihydrothieno[3,4-d]pyrimidin-2-yl)phenyl)urea | Ex 14 | B | 450 | 2.08 | >95% |

TABLE 9-continued

| Structure | Name | Example Number | LCMS Method | ES+ | RT (mins) | Purity (%) |
|---|---|---|---|---|---|---|
| 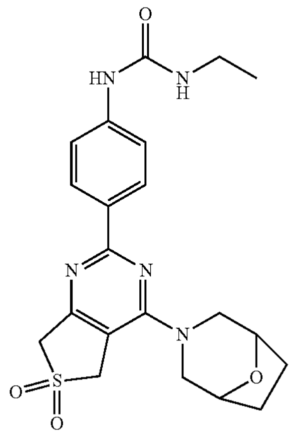 [SMILES: CCNC(=O)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-ethylurea | Ex 15 | B | 444 | 2.07 | >95% |
| 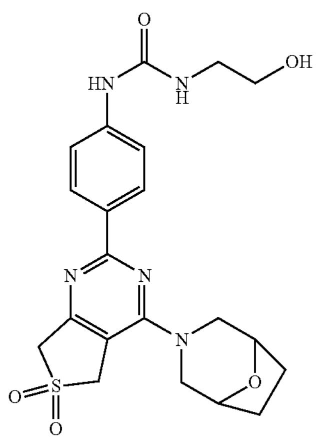 [SMILES: O=C(NCCO)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-(2-hydroxyethyl)urea | Ex 16 | B | 460 | 1.93 | 90-95% |
| 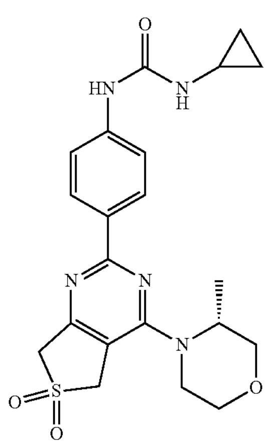 [SMILES: C[C@@H]1COCCN1c1nc(-c2ccc(NC(=O)NC3CC3)cc2)nc2c1CS(=O)(=O)C2] | (R)-1-cyclopropyl-3-(4-(4-(3-methylmorpholino)-6,6-dioxido-5,7-dihydrothieno[3,4-d]pyrimidin-2-yl)phenyl)urea | Ex 17 | B | 444 | 2.10 | 90-95% |

TABLE 9-continued

| Structure | Name | Example Number | LCMS Method | ES+ | RT (mins) | Purity (%) |
|---|---|---|---|---|---|---|
| 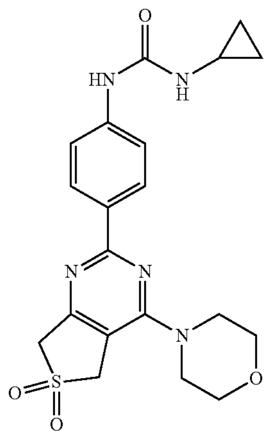 [SMILES: O=C(Nc1ccc(-c2nc3c(c(N4CCOCC4)n2)CS(=O)(=O)C3)cc1)NC1CC1] | 1-cyclopropyl-3-(4-(4-morpholino-6,6-dioxido-5,7-dihydrothieno[3,4-d]pyrimidin-2-yl)phenyl)urea | Ex 18 | B | 430 | 2.05 | >95% |
| 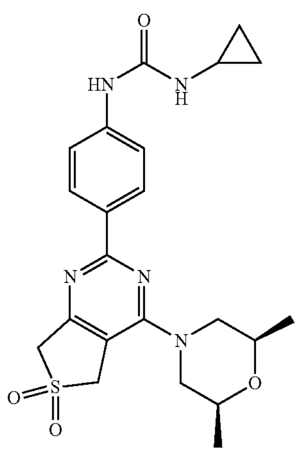 [SMILES: C[C@@H]1CN(c2nc(-c3ccc(NC(=O)NC4CC4)cc3)nc3c2CS(=O)(=O)C3)C[C@H](C)O1] | 1-cyclopropyl-3-(4-(4-((2S,6R)-2,6-dimethylmorpholino)-6,6-dioxido-5,7-dihydrothieno[3,4-d]pyrimidin-2-yl)phenyl)urea | Ex 19 | B | 458 | 2.20 | >95% |
| 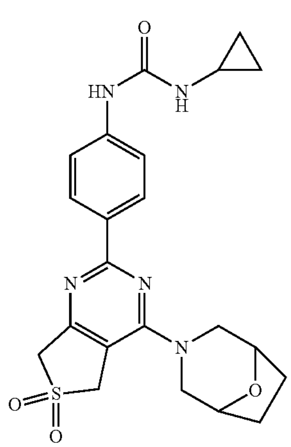 [SMILES: O=C(Nc1ccc(-c2nc3c(c(N4CC5CCC(C4)O5)n2)CS(=O)(=O)C3)cc1)NC1CC1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-cyclopropylurea | Ex 20 | B | 456 | 2.08 | 90-95% |

TABLE 9-continued

| Structure | Name | Example Number | LCMS Method | ES+ | RT (mins) | Purity (%) |
|---|---|---|---|---|---|---|
| 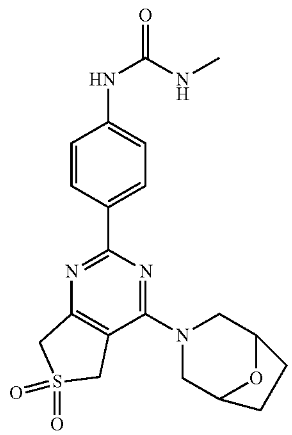 [SMILES: CNC(=O)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-methylurea | Ex 21 | B | 430 | 1.98 | >95% |
| 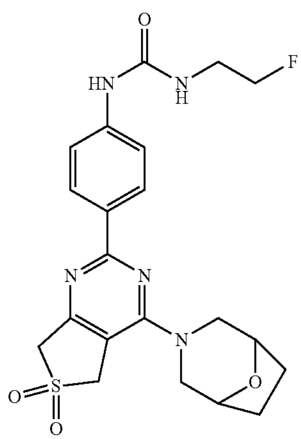 [SMILES: O=C(NCCF)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-(2-fluoroethyl)urea | Ex 22 | B | 462 | 4.50 | >95% |
| 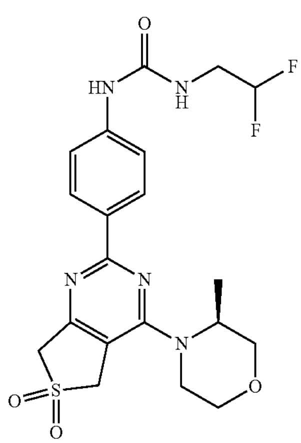 [SMILES: C[C@H]1COCCN1c1nc(-c2ccc(NC(=O)NCC(F)F)cc2)nc2c1CS(=O)(=O)C2] | (S)-1-(2,2-difluoroethyl)-3-(4-(4-(3-methylmorpholino)-6,6-dioxido-5,7-dihydrothieno[3,4-d]pyrimidin-2-yl)phenyl)urea | Ex 23 | B | 468 | 4.56 | 90-95% |

TABLE 9-continued
| Structure | Name | Example Number | LCMS Method | ES+ | RT (mins) | Purity (%) |
|---|---|---|---|---|---|---|
| 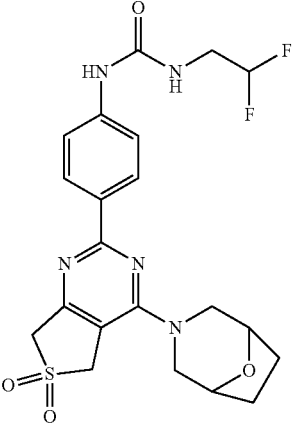 [SMILES: O=C(NCC(F)F)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-(2,2-difluoroethyl)urea | Ex 24 | B | 480 | 4.58 | >95% |
| 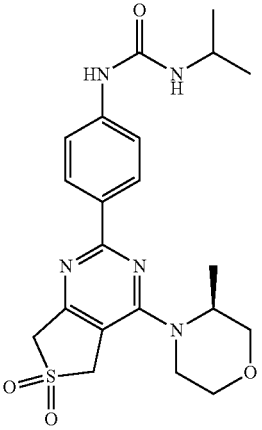 [SMILES: CC(C)NC(=O)Nc1ccc(-c2nc3c(c(N4CCOC[C@@H]4C)n2)CS(=O)(=O)C3)cc1] | (S)-1-isopropyl-3-(4-(4-(3-methylmorpholino)-6,6-dioxido-5,7-dihydrothieno[3,4-d]pyrimidin-2-yl)phenyl)urea | Ex 25 | B | 446 | 4.67 | >95% |
| 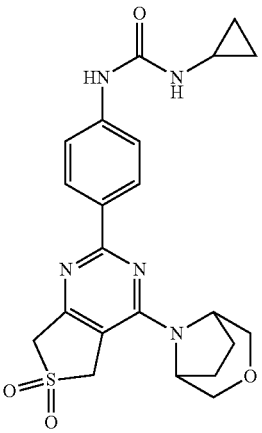 [SMILES: O=C(Nc1ccc(-c2nc3c(c(N4C5CCC4COC5)n2)CS(=O)(=O)C3)cc1)NC1CC1] | 1-(4-(4-(3-oxa-8-azabicyclo[3.2.1]octan-8-yl)-6,6-dioxido-5,7-dihydrothieno[3,4-d]pyrimidin-2-yl)phenyl)-3-cyclopropylurea | Ex 26 | B | 456 | 4.61 | >95% |

TABLE 9-continued

| Structure | Name | Example Number | LCMS Method | ES+ | RT (mins) | Purity (%) |
|---|---|---|---|---|---|---|
| 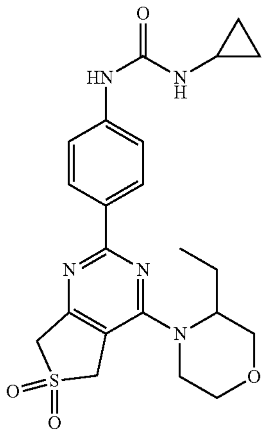 [SMILES: CCC1COCCN1c1nc(-c2ccc(NC(=O)NC3CC3)cc2)nc2c1CS(=O)(=O)C2] | 1-cyclopropyl-3-(4-(4-(3-ethylmorpholino)-6,6-dioxido-5,7-dihydrothieno[3,4-d]pyrimidin-2-yl)phenyl)urea | Ex 27 | B | 458 | 4.64 | >95% |
| 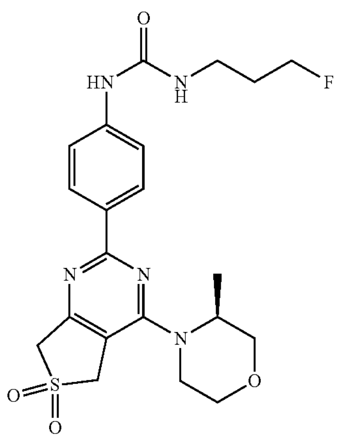 [SMILES: C[C@H]1COCCN1c1nc(-c2ccc(NC(=O)NCCCF)cc2)nc2c1CS(=O)(=O)C2] | (S)-1-(3-fluoropropyl)-3-(4-(4-(3-methylmorpholino)-6,6-dioxido-5,7-dihydrothieno[3,4-d]pyrimidin-2-yl)phenyl)urea | Ex 28 | B | 464 | 4.53 | 90-95% |
| 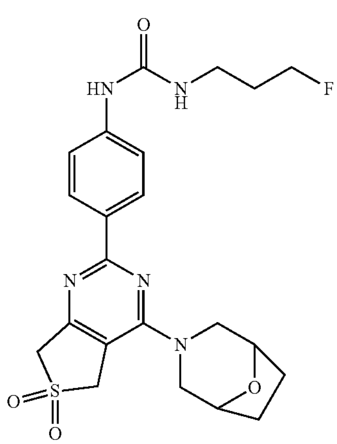 [SMILES: O=C(NCCCF)Nc1ccc(-c2nc3c(c(N4CC5CCC(C4)O5)n2)CS(=O)(=O)C3)cc1] | 1-(4-(4-(8-oxa-3-azabicyclo[3.2.1]octan-3-yl)-6,6-dioxido-5,7-dihydrothieno[3,4-d]pyrimidin-2-yl)phenyl)-3-(3-fluoropropyl)urea | Ex 29 | B | 476 | 4.57 | >95% |

TABLE 9-continued

| Structure | Name | Example Number | LCMS Method | ES+ | RT (mins) | Purity (%) |
|---|---|---|---|---|---|---|
| 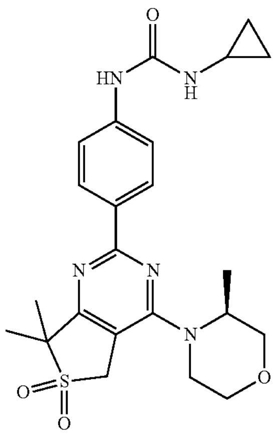 [SMILES: C[C@H]1COCCN1c1nc(-c2ccc(NC(=O)NC3CC3)cc2)nc2c1CS(=O)(=O)C2(C)C] | (S)-1-cyclopropyl-3-(4-(7,7-dimethyl-4-(3-methylmorpholino)-6,6-dioxido-5,7-dihydrothieno[3,4-d]pyrimidin-2-yl)phenyl)urea | Ex 30 | B | 472 | 2.30 | >95% |
| 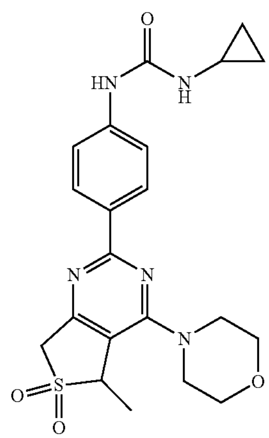 [SMILES: CC1c2c(nc(-c3ccc(NC(=O)NC4CC4)cc3)nc2N2CCOCC2)CS1(=O)=O] | 1-cyclopropyl-3-(4-(5-methyl-4-morpholino-6,6-dioxido-5,7-dihydrothieno[3,4-d]pyrimidin-2-yl)phenyl)urea | Ex 31 | B | 444 | 2.07 | >95% |
| 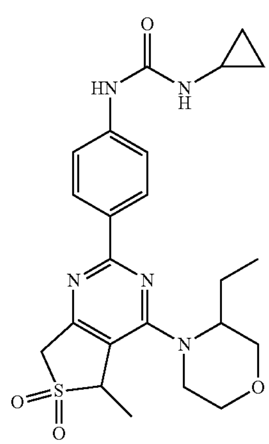 [SMILES: CCC1COCCN1c1nc(-c2ccc(NC(=O)NC3CC3)cc2)nc2c1C(C)S(=O)(=O)C2] | 1-cyclopropyl-3-(4-(4-(3-ethylmorpholino)-5-methyl-6,6-dioxido-5,7-dihydrothieno[3,4-d]pyrimidin-2-yl)phenyl)urea | Ex 32 | B | 472 | 2.20 | >95% |

| Structure | Name | Example Number | LCMS Method | ES+ | RT (mins) | Purity (%) |
|---|---|---|---|---|---|---|
| 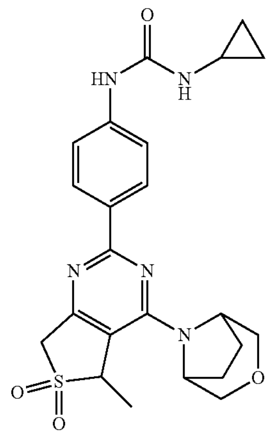 [SMILES: CC1c2c(nc(-c3ccc(NC(=O)NC4CC4)cc3)nc2N2C3CCC2COC3)CS1(=O)=O] | 1-(4-(4-(3-oxa-8-azabicyclo[3.2.1]octan-8-yl)-5-methyl-6,6-dioxido-5,7-dihydrothieno[3,4-d]pyrimidin-2-yl)phenyl)-3-cyclopropylurea | Ex 33 | B | 470 | 2.12 | >95% |
| 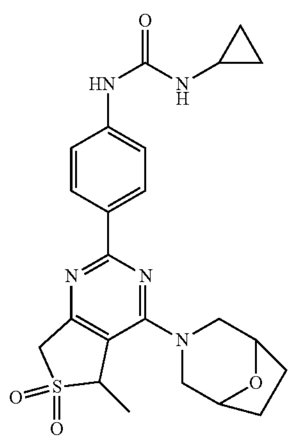 [SMILES: CC1c2c(nc(-c3ccc(NC(=O)NC4CC4)cc3)nc2N2CC3CCC(C2)O3)CS1(=O)=O] | 1-(4-(4-(8-oxa-3-azabicyclo[3.2.1]octan-3-yl)-5-methyl-6,6-dioxido-5,7-dihydrothieno[3,4-d]pyrimidin-2-yl)phenyl)-3-cyclopropylurea | Ex 34 | B | 470 | 2.10 | 90-95% |
| 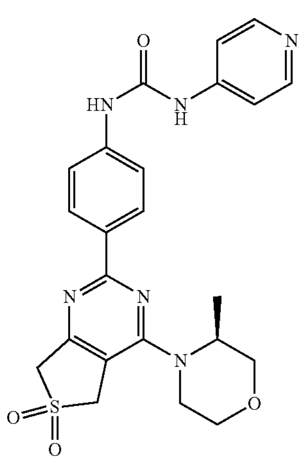 [SMILES: C[C@H]1COCCN1c1nc(-c2ccc(NC(=O)Nc3ccncc3)cc2)nc2c1CS(=O)(=O)C2] | (S)-1-(4-(4-(3-methylmorpholino)-6,6-dioxido-5,7-dihydrothieno[3,4-d]pyrimidin-2-yl)phenyl)-3-(pyridin-4-yl)urea | Ex 35 | A | 481 | 2.97 | 90-95% |

TABLE 9-continued

| Structure | Name | Example Number | LCMS Method | ES+ | RT (mins) | Purity (%) |
|---|---|---|---|---|---|---|
| 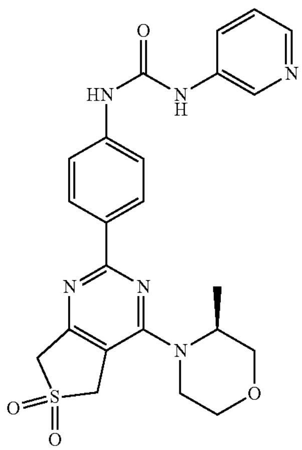 [SMILES: C[C@H]1COCCN1c1nc(-c2ccc(NC(=O)Nc3cccnc3)cc2)nc2c1CS(=O)(=O)C2] | (S)-1-(4-(4-(3-methylmorpholino)-6,6-dioxido-5,7-dihydrothieno[3,4-d]pyrimidin-2-yl)phenyl)-3-(pyridin-3-yl)urea | Ex 36 | A | 481 | 3.06 | 90-95% |
| 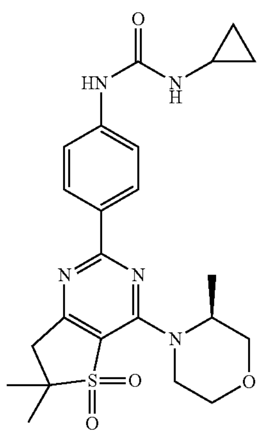 [SMILES: C[C@H]1COCCN1c1nc(-c2ccc(NC(=O)NC3CC3)cc2)nc2c1S(=O)(=O)C(C)(C)C2] | (S)-1-cyclopropyl-3-(4-(6,6-dimethyl-4-(3-methylmorpholino)-5,5-dioxido-6,7-dihydrothieno[3,2-d]pyrimidin-2-yl)phenyl)urea | Ex 37 | A | 472 | 3.31 | >95% |
| 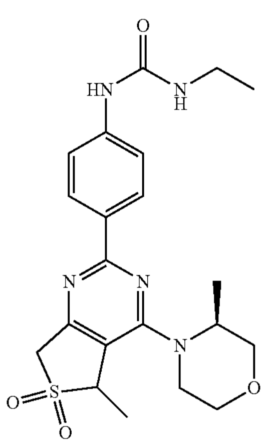 [SMILES: CCNC(=O)Nc1ccc(-c2nc3c(c(N4CCOC[C@@H]4C)n2)C(C)S(=O)(=O)C3)cc1] | 1-ethyl-3-(4-(5-methyl-4-((S)-3-methylmorpholino)-6,6-dioxido-5,7-dihydrothieno[3,4-d]pyrimidin-2-yl)phenyl)urea | Ex 38 | A | 446 | 4.73 | >95% |

TABLE 9-continued
| Structure | Name | Example Number | LCMS Method | ES+ | RT (mins) | Purity (%) |
|---|---|---|---|---|---|---|
| 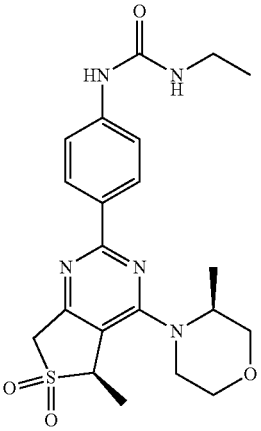 [SMILES: CCNC(=O)Nc1ccc(-c2nc3c(c(N4CCOC[C@@H]4C)n2)[C@@H](C)S(=O)(=O)C3)cc1] | 1-ethyl-3-(4-((R)-5-methyl-4-((S)-3-methylmorpholino)-6,6-dioxido-5,7-dihydrothieno[3,4-d]pyrimidin-2-yl)phenyl)urea | Ex 39 | D | 446 | 2.68 | >95% |
| 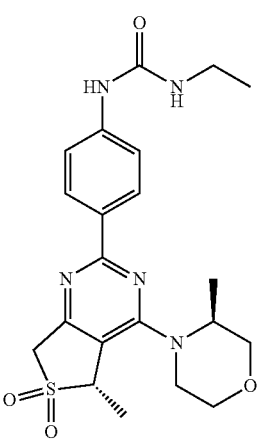 [SMILES: CCNC(=O)Nc1ccc(-c2nc3c(c(N4CCOC[C@@H]4C)n2)[C@H](C)S(=O)(=O)C3)cc1] | 1-ethyl-3-(4-((S)-5-methyl-4-((S)-3-methylmorpholino)-6,6-dioxido-5,7-dihydrothieno[3,4-d]pyrimidin-2-yl)phenyl)urea | Ex 40 | D | 446 | 2.68 | >95% |
| 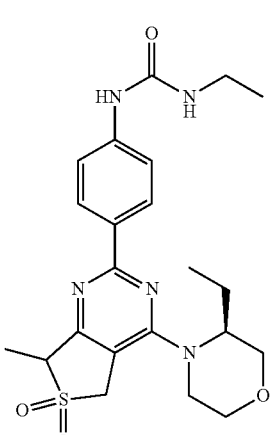 | 1-ethyl-3-(4-(4-((S)-3-ethylmorpholino)-7-methyl-6,6-dioxido-5,7-dihydrothieno[3,4-d]pyrimidin-2-yl)phenyl)urea | Ex 41 | C | 460 | 2.90 | >95% |

Example 42

1-ethyl-3-(4-(5,7,7-trimethyl-4-((S)-3-methylmorpholino)-6,6-dioxido-5,7-dihydrothieno[3,4-d]pyrimidin-2-yl)phenyl)urea Step (i)

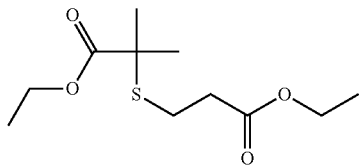 [SMILES: CCOC(=O)CCSC(C)(C)C(=O)OCC]

To a solution of EtONa (6.5 g, 95.4 mmol) in EtOH (185 mL) was added 1 (18.50 g, 95.4 mmol) and 3-mercaptopropionic acid ethyl ester (1.28 g, 95.4 mmol). The mixture was stirred at room temperature for overnight. After reaction, the mixture was filtered and the filtered cake was washed with ethylacetate, then the filtrate was concentrated in vacuum. The concentration was diluted with ethylacetate and washed with water for three times. The organic phase was dried over $MgSO_4$ and concentrated in vacuum to give compound 2 (2.1 g) as a liquid which was used directly for the next step.

Step (ii)

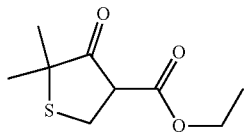

To a solution of EtONa (5.76 g, 84.60 mmol) in THF (105 mL) was added drop wise compound 2 (10.50 g, 42.30 mmol), then the mixture was heated to 60□ and stirred for overnight. After reaction, the mixture was poured into sat. $NH_4Cl$ solution and extracted with ethyl acetate. The organic phase was dried over $MgSO_4$, then filtered and concentrated in vacuum to give crude compound 3 (7.5 g) which was used directly for the next step.

Step (iii)

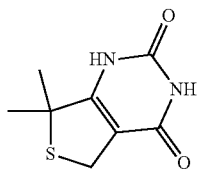

The mixture of compound 3 (2.50 g, 12.30 mmol) and urea (2.25 g, 37.50 mmol) was heated to 160° C. in an open flask (water and EtOH formed in the reaction were evaporated at high temperature) then the brown oil was further stirred at the same temperature for 3 hrs. After reaction, water (12 mL) was added to the hot reaction mixture, the precipitate was filtered and the filtered cake was washed with water, the residue was dried in vacuum to give crude compound 4 (1.6 g) as a yellow solid.

Step (iv)

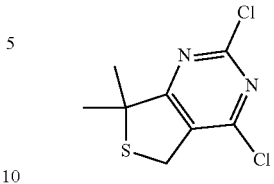

To a solution of compound 4 (2.0 g, 10 mmol) in $PhPOCl_2$ (6.0 g, 31 mmol) was heated to 160° C., then the mixture was stirred for 3 hrs. After reaction, the mixture was cooled to room temperature and then poured into ice water, the aqueous phase was extracted with ethyl acetate. The organic phase was dried over $MgSO_4$ and concentrated in vacuum. The residue was purified by silica gel chromatography (petroleum ether: ethyl acetate=50:1) to give dichloro-Core (1.35 g, yield 57%) as a white solid. $^1H$ NMR ($CDCl_3$, 400 MHz) δ 1.710 (s, 6H), 4.107 (s, 2H); LCMS ($ESI^-$): m/z 235 $(M+H)^+$.

Step (v)

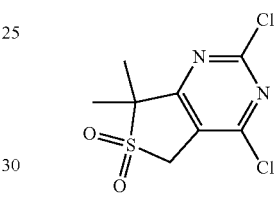

To a solution of Dichloro-Core (6.0 g, 23.8 mmol) in DCM (60 mL) was added m-CPBA (12.26 g, 71.30 mmol) in portions under an ice-bath and stirred at room temperature overnight. After the reaction was complete, the solution was added DCM (40 mL) and aq. $NH_4Cl$ (100 mL). The solid was removed by filtration and the organic layer was washed with aq. $NaHCO_3$ and brine, dried over $Na_2SO_4$ and concentrated to give compound 6 (6 g, yield 91.6%) as white solid. $^1H$ NMR ($CDCl_3$, 400 MHz) δ 1.70 (s, 6H), 4.34 (s, 2H);

LCMS ($ESI^-$): m/z 267 $(M+H)^+$.

Step (vi)

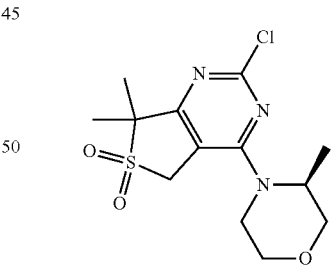

To a solution of Compound 6 (1.4 g, 5.2 mmol) and TEA (1.1 g, 10.5 mmol) in DMF (14 mL) was added (S)-3-methylmorpholine (0.52 g, 5.20 mmol) dropwise and stirred at room temperature overnight. After the reaction was complete, EtOAc (20 mL) and $H_2O$ (50 mL) was added. The organic layer was washed with brine, dried over $Na_2SO_4$ and concentrated to give crude product, which was purified by column chromatography on silica gel (elute: petroleum ether/ethyl acetate=5/1-2/1) to give (S)-2-chloro-7,7-dimethyl-4-(3-methylmorpholino)-5,7-dihydrothieno[3,4-d]pyrimidine 6,6-dioxide (0.8 g, yield 46%) as a white solid. $^1H$ NMR ($CDCl_3$, 400 MHz) δ 1.39 (d, 3H), 1.60 (s, 6H), 3.46-3.56 (m, 2H), 3.70-3.77 (m, 2H), 3.96-3.98 (m, 2H), 4.16-4.26 (m, 3H); LCMS (ESI⁻): m/z 332 (M+H)⁺.

Step (vii)

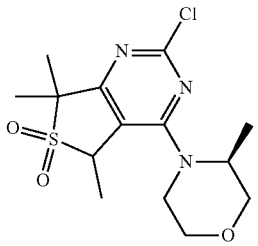 [SMILES: CC1c2c(N3CCOC[C@@H]3C)nc(Cl)nc2C(C)(C)S1(=O)=O]

LDA (2.5 mL, 5 mmol) was added dropwise to a solution of (S)-2-chloro-7,7-dimethyl-4-(3-methylmorpholino)-5,7-dihydrothieno[3,4-d]pyrimidine 6,6-dioxide (Step vi, 1.5 g, 4.5 mmol) in THF (30 mL) at −78° C. The mixture was stirred at this temperature for 0.5 h, MeI (0.7 g, 5 mmol) in THF (5 mL) was added dropwise to the above mixture. The resulted mixture was stirred at room temperature for 2 h. Then the mixture was poured into sat.NH₄Cl, extracted with EtOAc (3×30 mL). The organic layer was washed with brine, dried over Na₂SO₄ and concentrated in vacuo. The residue was purified by column chromatography to give 2-chloro-5,7,7-trimethyl-4-((S)-3-methylmorpholino)-5,7-dihydrothieno[3,4-d]pyrimidine 6,6-dioxide (1.2 g, yield 77%) as a yellow solid. ¹H NMR (400 MHz, CDCl₃) 1.38-4.31 (m, 1H), 4.29-4.21 (m, 1H), 3.99-3.96 (m, 1H), 3.78-3.43 (m, 5H), 1.65-1.25 (m, 12H).

Step (iii)

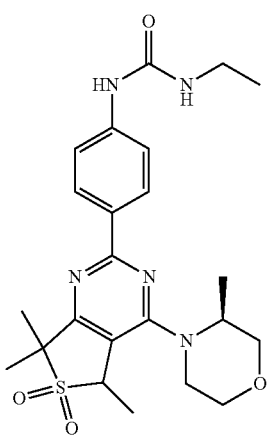 [SMILES: CCNC(=O)Nc1ccc(-c2nc(N3CCOC[C@@H]3C)c3c(n2)C(C)(C)S(=O)(=O)C3C)cc1]

The title compound was synthesised following the procedure in Example 5 (step viii) using 2-chloro-5,7,7-trimethyl-4-((S)-3-methylmorpholino)-5,7-dihydrothieno[3,4-d]pyrimidine 6,6-dioxide and 1-ethyl-3-(4-(4,4,5,5-tetramethyl-1,3,2-dioxaborolan-2-yl)phenyl)urea. LC-MS (Method D), (ES+) 474, RT=3.00 min.

Example 43

1-cyclopropyl-3-(4-(7-fluoro-7-methyl-4-((S)-3-methylmorpholino)-6,6-dioxido-5,7-dihydrothieno[3,4-d]pyrimidin-2-yl)phenyl)urea Step (i)

To a solution of 2,4-dichloro-7-methyl-5,7-dihydrothieno[3,4-d]pyrimidine 6,6-dioxide (Example 7, step (vi)) (160 mg, 0.63 mmol), and triethylamine (64 mg, 0.63 mmol) in DMF (3 mL) at 0° C. was added 3-(S)-methylmorpholine (57 mg, 0.57 mmol). The resultant mixture was stirred at rt for 2 h. The solvent was removed under vacuum and the residue obtained partitioned between water and ethyl acetate. The organic layer was dried (Na₂SO₄) and concentrated to give the product which was purified by preparative TLC (petroleum ether/ethyl acetate=2/1) to produce 2-chloro-7-methyl-4-[(3S)-3-methylmorpholin-4-yl]-5,7-dihydrothieno[3,4-d]pyrimidine 6,6-dioxide (72 mg, 36% yield). LC-MS (Method A), (ES+) 318/320, RT=2.95 min.

Step (ii)

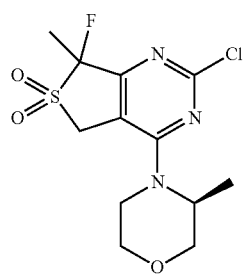 [SMILES: C[C@H]1COCCN1c1nc(Cl)nc2c1CS(=O)(=O)C2(C)F]

A solution of 2-chloro-7-methyl-4-[(3S)-3-methylmorpholin-4-yl]-5,7-dihydrothieno[3,4-d]pyrimidine 6,6-dioxide (0.15 g, 0.47 mmol) in absolute THF (10 mL) was cooled to −70° C., LDA (2M, 0.26 mL) was added dropwise and stirred for 30 min. NFSI (0.15 g, 0.47 mmol) in THF (2 mL) was added slowly. Then it was allowed to warm to room temperature gradually and stirred for 1 hrs. After reaction, it was poured into NH₄Cl solution, extracted with EA, the organic layer was washed with brine, dried over Na₂SO₄, evaporated and purified by Pre-TLC to give 2-chloro-7-fluoro-7-methyl-4-((S)-3-methylmorpholino)-5,7-dihydrothieno[3,4-d]pyrimidine 6,6-dioxide (0.10 g, yield 63%) as a white solid. ¹H NMR (400 MHz, CDCl₃) 4.44-4.38 (m, 1H), 4.19-3.99 (m, 3H), 3.78-3.40 (m, 5H), 2.03 (d, 3H), 1.57-1.35 (m, 3H).

Step (iii)

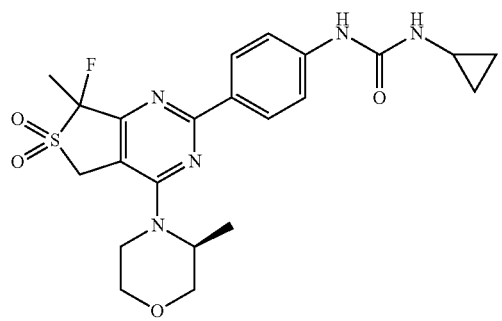 [SMILES: C[C@H]1COCCN1c1nc(-c2ccc(NC(=O)NC3CC3)cc2)nc2c1CS(=O)(=O)C2(C)F]

The title compound was synthesised following the procedure in Example 5 (step viii) using 2-chloro-7-fluoro-7-methyl-4-((S)-3-methylmorpholino)-5,7-dihydrothieno[3,4-d]pyrimidine 6,6-dioxide and 1-cyclopropyl-3-(4-(4,4,5,5-tetramethyl-1,3,2-dioxaborolan-2-yl)phenyl)urea.

LC-MS (Method D), (ES+) 476, RT=2.90 min.

Example 44

1-cyclopropyl-3-(4-(5,7-dimethyl-4-((S)-3-methyl-morpholino)-6,6-dioxido-5,7-dihydrothieno[3,4-d]pyrimidin-2-yl)phenyl)urea Step (i)

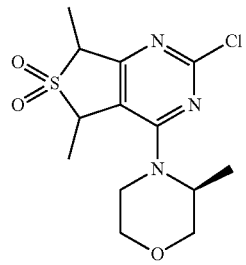 [SMILES: CC1c2nc(Cl)nc(N3CCOC[C@@H]3C)c2C(C)S1(=O)=O]

A solution of 2-chloro-7-methyl-4-[(3S)-3-methylmorpholin-4-yl]-5,7-dihydrothieno[3,4-d]pyrimidine (Example 6, step (vii))(0.5 g, 1.58 mmol) in THF (10 mL) was cooled to −70° C., LDA (2M, 0.86 mL) was added dropwise and stirred for 30 min. MeI (0.24 g, 1.73 mmol) in THF (2 mL) was added slowly. The mixture was allowed to warm to room temperature gradually and stirred for 2 h. After reaction, it was poured into NH$_4$Cl solution, extracted with EtOAc, the organic layer was washed with brine, dried over Na$_2$SO$_4$, evaporated and purified by column to give 2-chloro-5,7-dimethyl-4-((S)-3-methylmorpholino)-5,7-dihydrothieno[3,4-d]pyrimidine 6,6-dioxide (0.2 g, yield 38%) as a slight yellow solid. LC-MS (Method G), (ES+) 332, RT=1.27 min.

Step (ii)

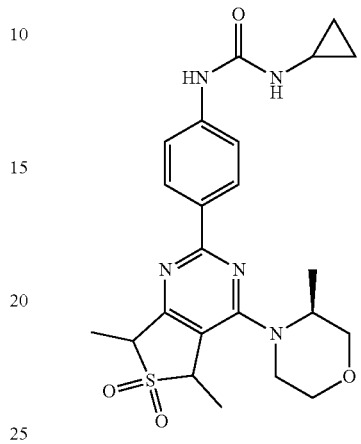

The title compound was synthesised following the procedure in Example 5 (step viii) using 2-chloro-5,7-dimethyl-4-((S)-3-methylmorpholino)-5,7-dihydrothieno[3,4-d]pyrimidine 6,6-dioxide and 1-cyclopropyl-3-(4-(4,4,5,5-tetramethyl-1,3,2-dioxaborolan-2-yl)phenyl)urea.

LC-MS (Method D), (ES+) 472, RT=2.90 min.

The following compounds were synthesized by procedures analogous to those described above:

TABLE 10

| Structure | Name | Example Number | LCMS Method | ES+ | RT (mins) | Purity (%) |
|---|---|---|---|---|---|---|
| 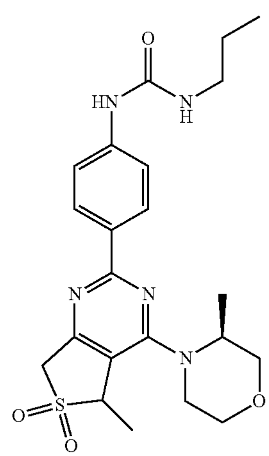 [SMILES: CCCNC(=O)Nc1ccc(-c2nc3c(c(N4CCOC[C@@H]4C)n2)C(C)S(=O)(=O)C3)cc1] | 1-(4-(5-methyl-4-((S)-3-methylmorpholino)-6,6-dioxido-5,7-dihydrothieno[3,4-d]pyrimidin-2-yl)phenyl)-3-propylurea | 45 | C | 460 | 3.27 | >95% |

TABLE 10-continued

| Structure | Name | Example Number | LCMS Method | ES+ | RT (mins) | Purity (%) |
|---|---|---|---|---|---|---|
| 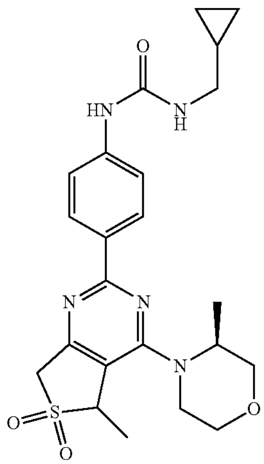 [SMILES: CC1c2c(nc(-c3ccc(NC(=O)NCC4CC4)cc3)nc2N2CCOC[C@@H]2C)CS1(=O)=O] | 1-(cyclopropylmethyl)-3-(4-(5-methyl-4-((S)-3-methylmorpholino)-6,6-dioxido-5,7-dihydrothieno[3,4-d]pyrimidin-2-yl)phenyl)urea | 46 | C | 472 | 3.32 | >95% |
| 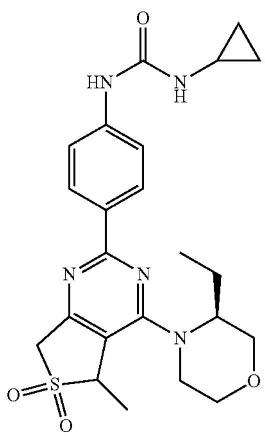 [SMILES: CC[C@H]1COCCN1c1nc(-c2ccc(NC(=O)NC3CC3)cc2)nc2c1C(C)S(=O)(=O)C2] | 1-cyclopropyl-3-(4-(4-((S)-3-ethylmorpholino)-5-methyl-6,6-dioxido-5,7-dihydrothieno[3,4-d]pyrimidin-2-yl)phenyl)urea | 47 | C | 472 | 3.26 | >95% |
| 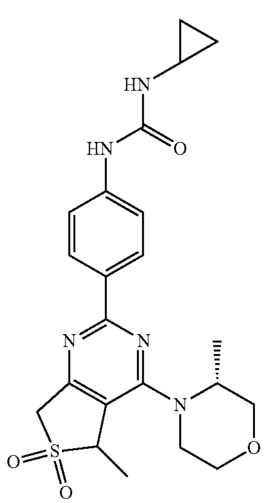 [SMILES: CC1c2c(nc(-c3ccc(NC(=O)NC4CC4)cc3)nc2N2CCOC[C@H]2C)CS1(=O)=O] | 1-cyclopropyl-3-(4-(5-methyl-4-((R)-3-methylmorpholino)-6,6-dioxido-5,7-dihydrothieno[3,4-d]pyrimidin-2-yl)phenyl)urea | 48 | D | 458 | 2.63 | >95% |

TABLE 10-continued

| Structure | Name | Example Number | LCMS Method | ES+ | RT (mins) | Purity (%) |
|---|---|---|---|---|---|---|
| 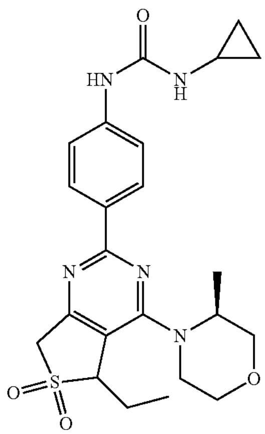 [SMILES: CCC1c2c(nc(-c3ccc(NC(=O)NC4CC4)cc3)nc2N2CCOC[C@@H]2C)CS1(=O)=O] | 1-cyclopropyl-3-(4-(5-ethyl-4-((S)-3-methylmorpholino)-6,6-dioxido-5,7-dihydrothieno[3,4-d]pyrimidin-2-yl)phenyl)urea | 49 | C | 472 | 3.3 | >95% |
| 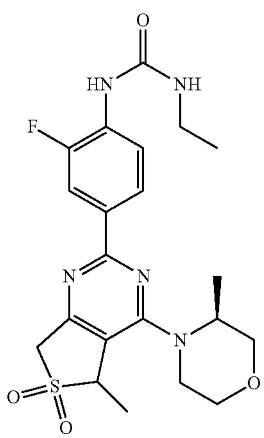 [SMILES: CCNC(=O)Nc1ccc(-c2nc3c(c(N4CCOC[C@@H]4C)n2)C(C)S(=O)(=O)C3)cc1F] | 1-ethyl-3-(2-fluoro-4-(5-methyl-4-((S)-3-methylmorpholino)-6,6-dioxido-5,7-dihydrothieno[3,4-d]pyrimidin-2-yl)phenyl)urea | 50 | D | 464 | 2.7 | >95% |
| 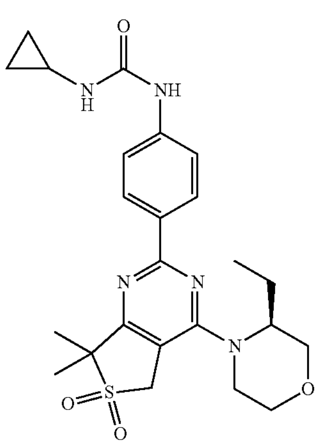 [SMILES: CC[C@H]1COCCN1c1nc(-c2ccc(NC(=O)NC3CC3)cc2)nc2c1CS(=O)(=O)C2(C)C] | (S)-1-cyclopropyl-3-(4-(4-(3-ethylmorpholino)-7,7-dimethyl-6,6-dioxido-5,7-dihydrothieno[3,4-d]pyrimidin-2-yl)phenyl)urea | 51 | D | 486 | 3 | >95% |

TABLE 10-continued

| Structure | Name | Example Number | LCMS Method | ES+ | RT (mins) | Purity (%) |
|---|---|---|---|---|---|---|
| 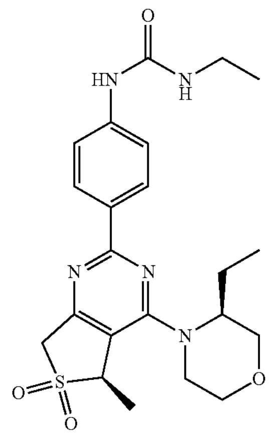 [SMILES: CCNC(=O)Nc1ccc(-c2nc3c(c(N4CCOC[C@@H]4CC)n2)[C@@H](C)S(=O)(=O)C3)cc1] | 1-ethyl-3-(4-((R)-4-((S)-3-ethylmorpholino)-5-methyl-6,6-dioxido-5,7-dihydrothieno[3,4-d]pyrimidin-2-yl)phenyl)urea | 52 | D | 460 | 3.27 | >95% |
| 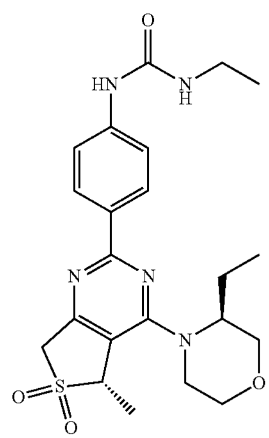 [SMILES: CCNC(=O)Nc1ccc(-c2nc3c(c(N4CCOC[C@@H]4CC)n2)[C@H](C)S(=O)(=O)C3)cc1] | 1-ethyl-3-(4-((S)-4-((S)-3-ethylmorpholino)-5-methyl-6,6-dioxido-5,7-dihydrothieno[3,4-d]pyrimidin-2-yl)phenyl)urea | 53 | D | 460 | 3.27 | >95% |
| 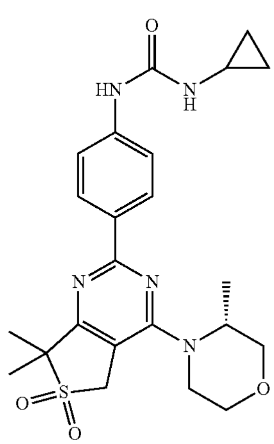 [SMILES: C[C@@H]1COCCN1c1nc(-c2ccc(NC(=O)NC3CC3)cc2)nc2c1CS(=O)(=O)C2(C)C] | (R)-1-cyclopropyl-3-(4-(7,7-dimethyl-4-(3-methylmorpholino)-6,6-dioxido-5,7-dihydrothieno[3,4-d]pyrimidin-2-yl)phenyl)urea | 54 | D | 472 | 2.97 | >95% |

TABLE 10-continued

| Structure | Name | Example Number | LCMS Method | ES+ | RT (mins) | Purity (%) |
|---|---|---|---|---|---|---|
| 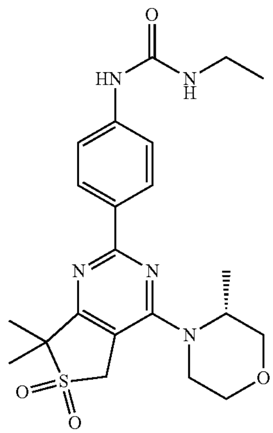 [SMILES: CCNC(=O)Nc1ccc(-c2nc(N3CCOC[C@H]3C)c3c(n2)C(C)(C)S(=O)(=O)C3)cc1] | (R)-1-(4-(7,7-dimethyl-4-(3-methylmorpholino)-6,6-dioxido-5,7-dihydrothieno[3,4-d]pyrimidin-2-yl)phenyl)-3-ethylurea | 55 | D | 460 | 2.94 | >95% |
| 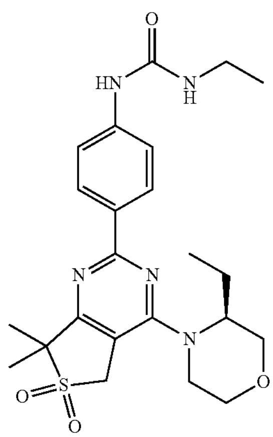 [SMILES: CCNC(=O)Nc1ccc(-c2nc(N3CCOC[C@@H]3CC)c3c(n2)C(C)(C)S(=O)(=O)C3)cc1] | (S)-1-ethyl-3-(4-(4-(3-ethylmorpholino)-7,7-dimethyl-6,6-dioxido-5,7-dihydrothieno[3,4-d]pyrimidin-2-yl)phenyl)urea | 56 | D | 474 | 3.48 | >95% |
| 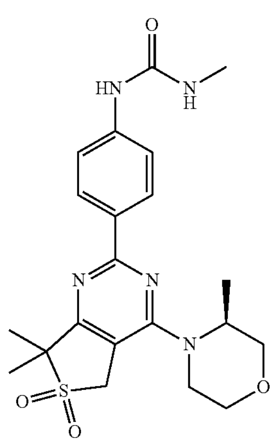 [SMILES: CNC(=O)Nc1ccc(-c2nc(N3CCOC[C@@H]3C)c3c(n2)C(C)(C)S(=O)(=O)C3)cc1] | (S)-1-(4-(7,7-dimethyl-4-(3-methylmorpholino)-6,6-dioxido-5,7-dihydrothieno[3,4-d]pyrimidin-2-yl)phenyl)-3-methylurea | 57 | D | 446 | 2.79 | >95% |

TABLE 10-continued

| Structure | Name | Example Number | LCMS Method | ES+ | RT (mins) | Purity (%) |
|---|---|---|---|---|---|---|
| 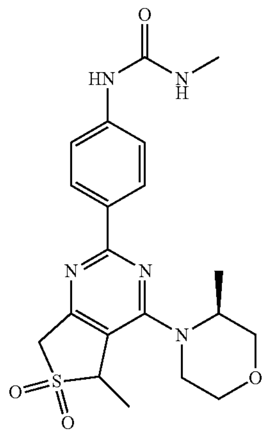 [SMILES: CNC(=O)Nc1ccc(-c2nc3c(c(N4CCOC[C@@H]4C)n2)C(C)S(=O)(=O)C3)cc1] | 1-methyl-3-(4-(5-methyl-4-((S)-3-methylmorpholino)-6,6-dioxido-5,7-dihydrothieno[3,4-d]pyrimidin-2-yl)phenyl)urea | 58 | D | 432 | 2.48 | >95% |
| 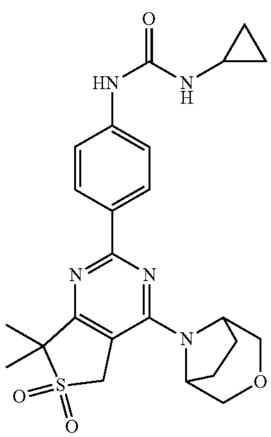 [SMILES: CC1(C)c2nc(-c3ccc(NC(=O)NC4CC4)cc3)nc(N3C4CCC3COC4)c2CS1(=O)=O] | 1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-cyclopropylurea | 59 | D | 484 | 2.92 | >95% |
| 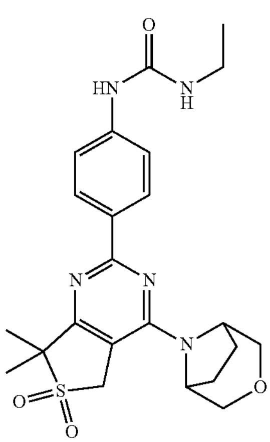 [SMILES: CCNC(=O)Nc1ccc(-c2nc(N3C4CCC3COC4)c3c(n2)C(C)(C)S(=O)(=O)C3)cc1] | 1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-ethylurea | 60 | D | 472 | 2.89 | >95% |

TABLE 10-continued

| Structure | Name | Example Number | LCMS Method | ES+ | RT (mins) | Purity (%) |
|---|---|---|---|---|---|---|
| 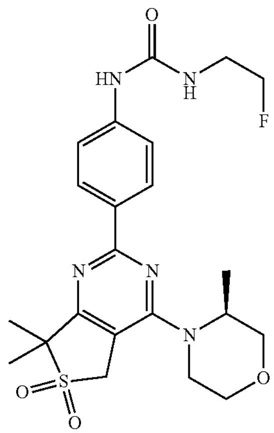 [SMILES: C[C@H]1COCCN1c1nc(-c2ccc(NC(=O)NCCF)cc2)nc2c1CS(=O)(=O)C2(C)C] | (S)-1-(4-(7,7-dimethyl-4-(3-methylmorpholino)-6,6-dioxido-5,7-dihydrothieno[3,4-d]pyrimidin-2-yl)phenyl)-3-(2-fluoroethyl)urea | 61 | D | 478 | 2.94 | >95% |
| 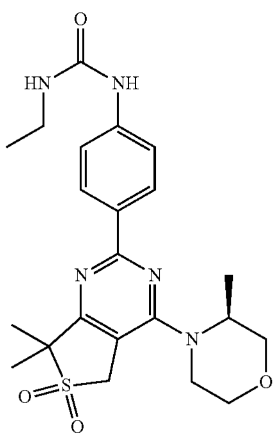 [SMILES: CCNC(=O)Nc1ccc(-c2nc(N3CCOC[C@@H]3C)c3c(n2)C(C)(C)S(=O)(=O)C3)cc1] | (S)-1-(4-(7,7-dimethyl-4-(3-methylmorpholino)-6,6-dioxido-5,7-dihydrothieno[3,4-d]pyrimidin-2-yl)phenyl)-3-ethylurea | 62 | D | 460 | 2.90 | >95% |
| 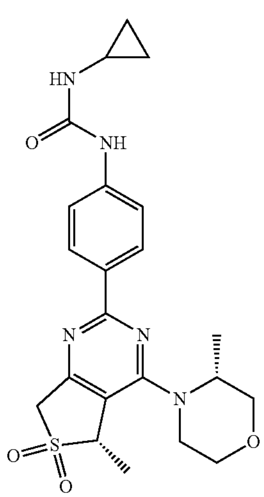 [SMILES: C[C@@H]1COCCN1c1nc(-c2ccc(NC(=O)NC3CC3)cc2)nc2c1[C@H](C)S(=O)(=O)C2] | 1-cyclopropyl-3-(4-((S)-5-methyl-4-((R)-3-methylmorpholino)-6,6-dioxido-5,7-dihydrothieno[3,4-d]pyrimidin-2-yl)phenyl)urea | 63 | D | 457 | 2.59 | >95% |

TABLE 10-continued

| Structure | Name | Example Number | LCMS Method | ES+ | RT (mins) | Purity (%) |
|---|---|---|---|---|---|---|
| 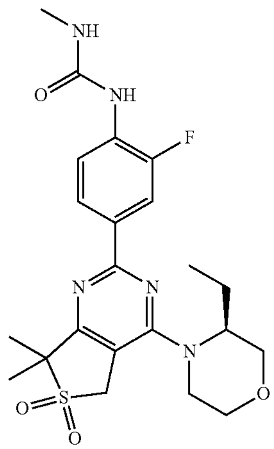 [SMILES: CC[C@H]1COCCN1c1nc(-c2ccc(NC(=O)NC)c(F)c2)nc2c1CS(=O)(=O)C2(C)C] | (S)-1-(4-(4-(3-ethylmorpholino)-7,7-dimethyl-6,6-dioxido-5,7-dihydrothieno[3,4-d]pyrimidin-2-yl)-2-fluorophenyl)-3-methylurea | 64 | D | 478 | 3.07 | >95% |
| 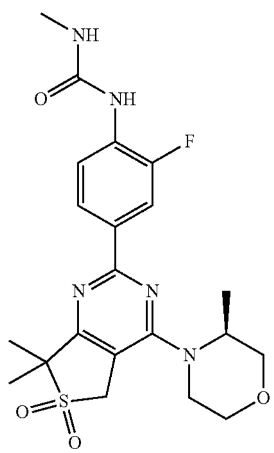 [SMILES: CNC(=O)Nc1ccc(-c2nc(N3CCOC[C@@H]3C)c3c(n2)C(C)(C)S(=O)(=O)C3)cc1F] | (S)-1-(4-(7,7-dimethyl-4-(3-methylmorpholino)-6,6-dioxido-5,7-dihydrothieno[3,4-d]pyrimidin-2-yl)-2-fluorophenyl)-3-methylurea | 65 | D | 464 | 2.86 | >95% |
| 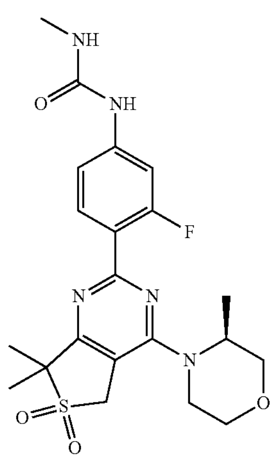 [SMILES: CNC(=O)Nc1ccc(-c2nc(N3CCOC[C@@H]3C)c3c(n2)C(C)(C)S(=O)(=O)C3)c(F)c1] | (S)-1-(4-(7,7-dimethyl-4-(3-methylmorpholino)-6,6-dioxido-5,7-dihydrothieno[3,4-d]pyrimidin-2-yl)-3-fluorophenyl)-3-methylurea | 66 | D | 464 | 2.73 | >95% |

TABLE 10-continued

| Structure | Name | Example Number | LCMS Method | ES+ | RT (mins) | Purity (%) |
|---|---|---|---|---|---|---|
| 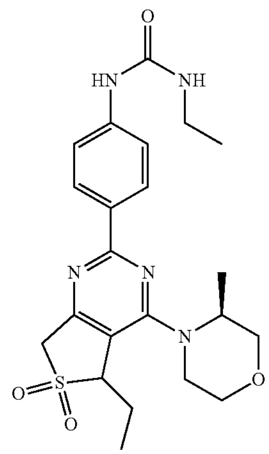 [SMILES: CCNC(=O)Nc1ccc(-c2nc3c(c(N4CCOC[C@@H]4C)n2)C(CC)S(=O)(=O)C3)cc1] | 1-ethyl-3-(4-(5-ethyl-4-((S)-3-methylmorpholino)-6,6-dioxido-5,7-dihydrothieno[3,4-d]pyrimidin-2-yl)phenyl)urea | 67 | D | 460 | 2.77 | >95% |
| 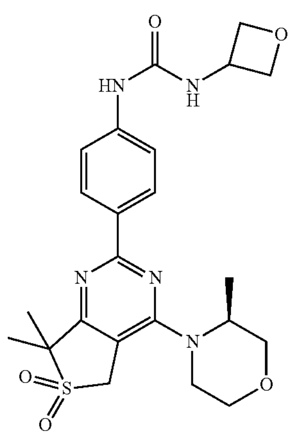 [SMILES: C[C@H]1COCCN1c1nc(-c2ccc(NC(=O)NC3COC3)cc2)nc2c1CS(=O)(=O)C2(C)C] | (S)-1-(4-(7,7-dimethyl-4-(3-methylmorpholino)-6,6-dioxido-5,7-dihydrothieno[3,4-d]pyrimidin-2-yl)phenyl)-3-(oxetan-3-yl)urea | 68 | E | 488 | 0.95 | >95% |
| 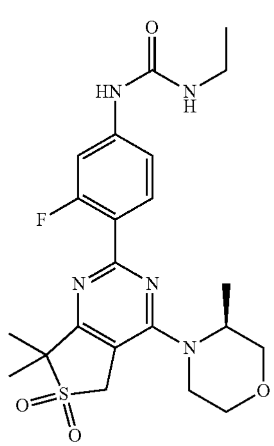 [SMILES: CCNC(=O)Nc1ccc(-c2nc(N3CCOC[C@@H]3C)c3c(n2)C(C)(C)S(=O)(=O)C3)c(F)c1] | (S)-1-(4-(7,7-dimethyl-4-(3-methylmorpholino)-6,6-dioxido-5,7-dihydrothieno[3,4-d]pyrimidin-2-yl)-3-fluorophenyl)-3-ethylurea | 69 | F | 478 | 2.46 | >95% |

TABLE 10-continued

| Structure | Name | Example Number | LCMS Method | ES+ | RT (mins) | Purity (%) |
|---|---|---|---|---|---|---|
| 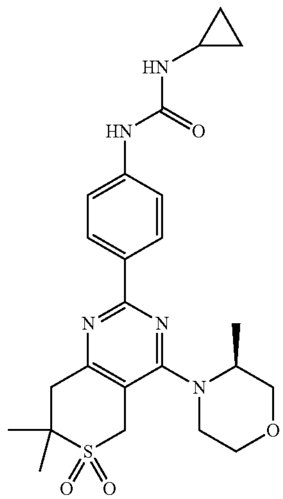 [SMILES: C[C@H]1COCCN1c1nc(-c2ccc(NC(=O)NC3CC3)cc2)nc2c1CS(=O)(=O)C(C)(C)C2] | (S)-1-cyclopropyl-3-(4-(7,7-dimethyl-4-(3-methylmorpholino)-6,6-dioxido-7,8-dihydro-5H-thiopyrano[4,3-d]pyrimidin-2-yl)phenyl)urea | 70 | C | 486 | 2.46 | >95% |
| 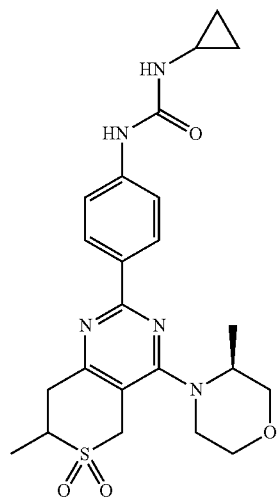 [SMILES: CC1Cc2nc(-c3ccc(NC(=O)NC4CC4)cc3)nc(N3CCOC[C@@H]3C)c2CS1(=O)=O] | 1-cyclopropyl-3-(4-(7-methyl-4-((S)-3-methylmorpholino)-6,6-dioxido-7,8-dihydro-5H-thiopyrano[4,3-d]pyrimidin-2-yl)phenyl)urea | 71 | C | 472 | 2.97 | >95% |
| 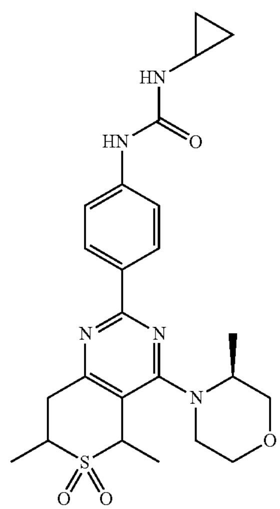 [SMILES: CC1Cc2nc(-c3ccc(NC(=O)NC4CC4)cc3)nc(N3CCOC[C@@H]3C)c2C(C)S1(=O)=O] | 1-cyclopropyl-3-(4-(5,7-dimethyl-4-((S)-3-methylmorpholino)-6,6-dioxido-7,8-dihydro-5H-thiopyrano[4,3-d]pyrimidin-2-yl)phenyl)urea | 72 | C | 486 | 2.78 | >95% |

TABLE 10-continued

| Structure | Name | Example Number | LCMS Method | ES+ | RT (mins) | Purity (%) |
|---|---|---|---|---|---|---|
| 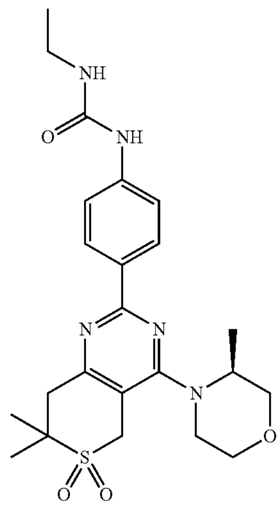 [SMILES: CCNC(=O)Nc1ccc(-c2nc3c(c(N4CCOC[C@@H]4C)n2)CS(=O)(=O)C(C)(C)C3)cc1] | (S)-1-(4-(7,7-dimethyl-4-(3-methylmorpholino)-6,6-dioxido-7,8-dihydro-5H-thiopyrano[4,3-d]pyrimidin-2-yl)phenyl)-3-ethylurea | 73 | C | 474 | 3.19 | >95% |
| 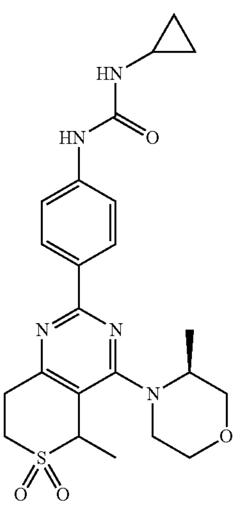 [SMILES: CC1c2c(nc(-c3ccc(NC(=O)NC4CC4)cc3)nc2N2CCOC[C@@H]2C)CCS1(=O)=O] | 1-cyclopropyl-3-(4-(5-methyl-4-((S)-3-methylmorpholino)-6,6-dioxido-7,8-dihydro-5H-thiopyrano[4,3-d]pyrimidin-2-yl)phenyl)urea | 74 | D | 472 | 3.07 | >95% |
| 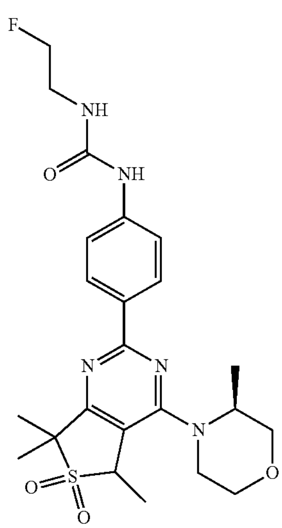 [SMILES: CC1c2c(N3CCOC[C@@H]3C)nc(-c3ccc(NC(=O)NCCF)cc3)nc2C(C)(C)S1(=O)=O] | 1-(2-fluoroethyl)-3-(4-(5,7,7-trimethyl-4-((S)-3-methylmorpholino)-6,6-dioxido-5,7-dihydrothieno[3,4-d]pyrimidin-2-yl)phenyl)urea | 75 | C | 492 | 3.07 | >95% |

TABLE 10-continued

| Structure | Name | Example Number | LCMS Method | ES+ | RT (mins) | Purity (%) |
|---|---|---|---|---|---|---|
| 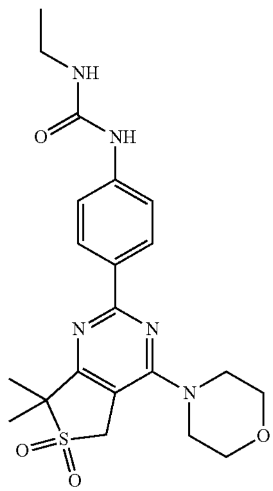 [SMILES: CCNC(=O)Nc1ccc(-c2nc(N3CCOCC3)c3c(n2)C(C)(C)S(=O)(=O)C3)cc1] | 1-(4-(7,7-dimethyl-4-morpholino-6,6-dioxido-5,7-dihydrothieno[3,4-d]pyrimidin-2-yl)phenyl)-3-ethylurea | 76 | C | 446 | 2.87 | >95% |
| 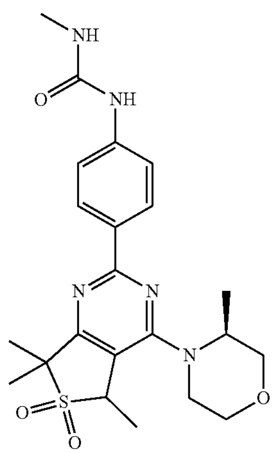 [SMILES: CNC(=O)Nc1ccc(-c2nc(N3CCOC[C@@H]3C)c3c(n2)C(C)(C)S(=O)(=O)C3C)cc1] | 1-methyl-3-(4-(5,7,7-trimethyl-4-((S)-3-methylmorpholino)-6,6-dioxido-5,7-dihydrothieno[3,4-d]pyrimidin-2-yl)phenyl)urea | 77 | C | 460 | 2.95 | >95% |
| 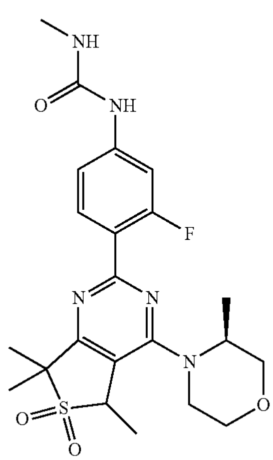 [SMILES: CNC(=O)Nc1ccc(-c2nc(N3CCOC[C@@H]3C)c3c(n2)C(C)(C)S(=O)(=O)C3C)c(F)c1] | 1-(3-fluoro-4-(5,7,7-trimethyl-4-((S)-3-methylmorpholino)-6,6-dioxido-5,7-dihydrothieno[3,4-d]pyrimidin-2-yl)phenyl)-3-methylurea | 78 | C | 478 | 2.94 | >95% |

TABLE 10-continued
| Structure | Name | Example Number | LCMS Method | ES+ | RT (mins) | Purity (%) |
|---|---|---|---|---|---|---|
| 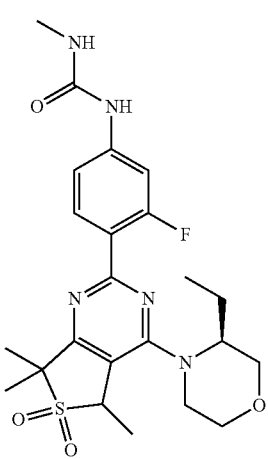 [SMILES: CC[C@H]1COCCN1c1nc(-c2ccc(NC(=O)NC)cc2F)nc2c1C(C)S(=O)(=O)C2(C)C] | 1-(4-(4-((S)-3-ethylmorpholino)-5,7,7-trimethyl-6,6-dioxido-5,7-dihydrothieno[3,4-d]pyrimidin-2-yl)-3-fluorophenyl)-3-methylurea | 79 | C | 492 | 3.03 | >95% |
| 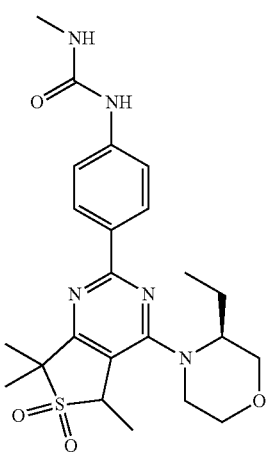 [SMILES: CC[C@H]1COCCN1c1nc(-c2ccc(NC(=O)NC)cc2)nc2c1C(C)S(=O)(=O)C2(C)C] | 1-(4-(4-((S)-3-ethylmorpholino)-5,7,7-trimethyl-6,6-dioxido-5,7-dihydrothieno[3,4-d]pyrimidin-2-yl)phenyl)-3-methylurea | 80 | C | 474 | 3.03 | >95% |
| 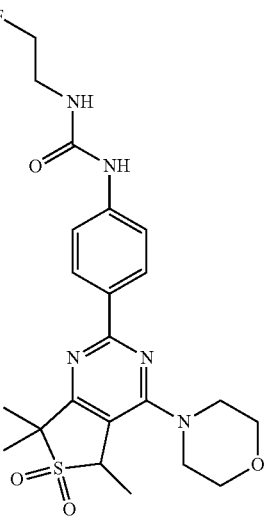 | 1-(2-fluoroethyl)-3-(4-(5,7,7-trimethyl-4-morpholino-6,6-dioxido-5,7-dihydrothieno[3,4-d]pyrimidin-2-yl)phenyl)urea | 81 | C | 478 | 2.87 | >95% |

TABLE 10-continued

| Structure | Name | Example Number | LCMS Method | ES+ | RT (mins) | Purity (%) |
|---|---|---|---|---|---|---|
| 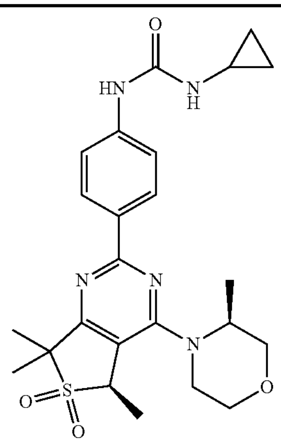 | 1-cyclopropyl-3-(4-((R)-5,7,7-trimethyl-4-((S)-3-methylmorpholino)-6,6-dioxido-5,7-dihydrothieno[3,4-d]pyrimidin-2-yl)phenyl)urea | 82 | C | 486 | 3.14 | >95% |

Kinobeads Assay Description
Determination of the Effect of the Compounds According to the Invention on mTOR The compounds of the present invention as described were tested in the mTOR kinobeads assay as described below. Briefly, test compounds (at various concentrations) and the affinity matrix (1:1 mixture of beads with immobilized phenylthiazole ligand 1 and beads with immobilized phenylmorpholin-chromen ligand; WO 2009/098021) were added to cell lysate aliquots and allowed to bind to the proteins in the lysate sample. After the incubation time the beads with captured proteins were separated from the lysate. Bound proteins were then eluted and the presence of mTOR, PI3K alpha (PI3Ka), PI3K beta (PI3 Kb), PI3K gamma (PI3 Kg), PI3K delta (PI3 Kd) and DNA-dependent protein kinase (DNA-PK) was detected and quantified using a specific antibody in a dot blot procedure and the Odyssey infrared detection system. Dose response curves for individual kinases were generated and $IC_{50}$ values calculated. Kinobeads assays for PI3 kinases (WO-A 2008/015013) and for kinase selectivity profiling (WO 2009/098021) have been previously described.

Washing of Affinity Matrix

The affinity matrix (beads with immobilized phenylmorpholin-chromen ligand) was washed three times with 15 ml of 1×DP buffer containing 0.2% NP40 (IGEPAL® CA-630, Sigma, #13021) and then resuspended in 5.5 ml of 1×DP buffer containing 0.2% NP40 (10% beads slurry).

5×DP buffer: 250 mM Tris-HCl pH 7.4, 25% Glycerol, 7.5 mM $MgCl_2$, 750 mM NaCl, 5 mM $Na_3VO_4$, filter the 5×-lysis buffer through 0.22 µm filter and store in aliquots at −80° C. The 5×DP buffer is diluted to 1×DP buffer containing 1 mM DTT and 25 mM NaF.

Preparation of Test Compounds

Stock solutions of test compounds were prepared in DMSO. In a 96 well plate 30 µl solution of diluted test compounds at 5 mM in DMSO were prepared. Starting with this solution a 1:3 dilution series (9 steps) was prepared. For control experiments (no test compound) a buffer containing 2% DMSO was used. Compound PI-103 served as a positive control (Calbiochem catalogue number 528100).

Cell Culture and Preparation of Cell Lysates

Jurkat cells (ATCC catalogue number TIB-152 Jurkat, clone E6-1) were grown in 1 litre Spinner flasks (Integra Biosciences, #182101) in suspension in RPMI 1640 medium (Invitrogen, #21875-034) supplemented with 10% Fetal Bovine Serum (Invitrogen) at a density between $0.15 \times 10^6$ and $1.2 \times 10^6$ cells/ml. Cells were harvested by centrifugation, washed once with 1×PBS buffer (Invitrogen, #14190-094) and cell pellets were frozen in liquid nitrogen and subsequently stored at −80° C.

Jurkat cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1873580) per 25 ml buffer was added. The material was dounced 10 times using a mechanized POTTER S, transferred to 50 ml falcon tubes, incubated for 30 minutes on ice and spun down for 10 min at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Jurkat cell lysate (approximately 50 mg protein per plate) was thawed in a water bath at room temperature and then kept on ice. To the thawed cell lysate 1×DP 0.8% NP40 buffer containing protease inhibitors (1 tablet for 25 ml buffer; EDTA-free protease inhibitor cocktail; Roche Diagnostics 1873580) was added in order to reach a final protein concentration of 5 mg/ml total protein. The diluted cell lysate was stored on ice.

Incubation of Lysate with Test Compound and Affinity Matrix

To a 96 well filter plate (Multiscreen HTS, BV Filter Plates, Millipore #MSBVN1250) were added per well: 50 µl affinity matrix (10% beads slurry), 3 µl of compound solution, and 100 µl of cell diluted lysate. Plates were sealed and incubated for three hours in a cold room on a Thermomixer with shaking (750 rpm). Afterwards the plate was washed three times with 230 µl washing buffer (1×DP 0.4% NP40). The filter plate was placed on top of a collection plate (Greiner bio-one, PP-microplate 96 well V-shape, 65120) and the beads were then eluted with 20 μl of sample buffer (100 mM Tris, pH 7.4, 4% SDS, 0.00025% Bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on Nitrocellulose membranes and using a first antibody directed against the kinase of interest and a fluorescently labelled secondary antibody (anti-mouse or anti-rabbit IRDye™ antibodies from Rockland). The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for one hour at room temperature. Blocked membranes were then incubated for 16 hours at 25° C. (or at 4 C) with the first antibody diluted in Odyssey blocking buffer (LICOR #927-40000). Afterwards the membrane was washed twice for 10 minutes with PBS buffer containing 0.1% Tween 20 at room temperature. Then the membrane was incubated for 60 minutes at room temperature with the detection antibody (IRDye™ labelled antibody from Rockland) diluted in Odyssey blocking buffer (LICOR #927-40000). Afterwards the membrane was washed twice for 10 minutes each with 1×PBS buffer containing 0.1% Tween 20 at room temperature. Then the membrane was rinsed once with PBS buffer to remove residual Tween 20. The membrane was kept in PBS buffer at 4° C. and then scanned with the Odyssey instrument. Fluorescence signals were recorded and analysed according to the instructions of the manufacturer.

Sources and Dilutions of Antibodies

TABLE 11

| Target kinase | Primary antibody (dilution) | Temperature of primary incubation | Secondary antibody (dilution) |
|---|---|---|---|
| PI3K alpha | Cell Signalling Technologies 4255 (1 in 100) | 25° C. | Anti-Rabbit (1 in 2500) |
| PI3K beta | Millipore 04-400 (1 in 1000) | 25° C. | Anti-Rabbit (1 in 2500) |
| PI3K delta | Santa Cruz SC7176 (1 in 1000) | 4° C. | Anti-Rabbit (1 in 2500) |
| PI3K gamma | Jena Bioscience ABD-026L (1 in 100) | 25° C. | Anti-Mouse (1 in 2500) |
| mTOR | Cell Signalling Technologies 2972 (1 in 500) | 25° C. | Anti-Rabbit (1 in 5000) |
| DNAPK | Calbiochem NA57 (1 in 1000) | 4° C. | Anti-Mouse (1 in 5000) |

Kinobeads Results

TABLE 12

Inhibition values (IC50 in μM) as determined in the kinobeads ™ assay (Activity level: A < 0.1 μM ≤ B < 1uM ≤ C ≤ 10 μM < D)

| Example | mTor | PI3Ka | PI3Kb | PI3Kg | PI3Kd | DNA-PK |
|---|---|---|---|---|---|---|
| 1 | A | D | D | D | D | D |
| 2 | A | D | D | D | D | D |
| 3 | A | D | | | | |
| 4 | A | D | | | | D |
| 5 | A | D | | | | D |
| 6 | A | C | | | | D |
| 7 | A | D | | | | D |
| 8 | A | D | | | | D |
| 9 | A | C | >3 | | >3 | D |
| 10 | A | D | >3 | >3 | >3 | D |
| 11 | B | D | D | D | D | D |
| 12 | A | C | D | D | D | D |
| 13 | A | C | D | D | D | C |
| 14 | A | D | D | D | D | >3 |
| 15 | A | D | D | D | D | D |
| 16 | A | D | D | D | D | D |
| 17 | B | D | D | D | D | D |
| 18 | A | D | D | D | D | D |
| 19 | C | D | | | | |
| 20 | A | D | | | | D |
| 21 | A | D | | | | |
| 22 | A | D | | | | D |
| 23 | A | D | | | | |
| 24 | B | D | | | | |
| 25 | B | D | | | | |
| 26 | A | D | | | | D |
| 27 | A | D | | | | D |
| 28 | B | D | | | | D |
| 29 | B | D | | | | D |
| 30 | A | D | D | D | D | D |
| 31 | B | D | | | | D |
| 32 | A | D | D | D | D | D |
| 33 | A | D | D | D | D | D |
| 34 | A | D | D | | D | D |
| 35 | A | D | | | | |
| 36 | A | D | | | | |
| 37 | B | D | D | D | D | D |
| 38 | A | C | D | D | D | D |
| 39 | A | C | D | D | D | D |
| 40 | A | C | D | D | D | D |
| 41 | A | C | D | D | D | D |
| 42 | A | D | D | D | D | D |
| 43 | A | D | D | D | D | D |
| 44 | A | C | D | D | D | D |
| 45 | A | C | D | D | D | D |
| 46 | A | C | C | D | D | D |
| 47 | B | D | D | D | D | D |
| 48 | A | D | D | D | D | D |
| 49 | A | C | D | D | D | D |
| 50 | A | D | D | D | D | D |
| 51 | A | D | D | D | D | D |
| 52 | A | D | D | D | D | D |
| 53 | A | D | D | D | D | D |
| 54 | A | C | C | D | D | D |
| 55 | A | C | D | D | D | D |
| 56 | A | D | D | D | D | D |
| 57 | A | D | D | D | D | D |
| 58 | A | D | D | D | D | D |
| 59 | A | D | D | D | D | D |
| 60 | A | D | D | D | D | D |
| 61 | A | D | D | D | D | D |
| 62 | B | D | D | D | D | D |
| 63 | B | D | D | D | D | D |
| 64 | B | C | D | D | D | D |
| 65 | B | D | D | D | D | D |
| 66 | A | D | D | D | D | D |
| 67 | A | D | D | D | D | D |
| 68 | B | D | D | D | D | D |
| 69 | A | D | D | D | D | D |
| 70 | A | D | D | D | D | D |
| 71 | A | D | D | D | D | D |
| 72 | A | D | D | D | D | D |
| 73 | A | D | D | D | D | D |
| 74 | A | D | D | D | D | D |
| 75 | A | D | D | D | — | — |
| 76 | A | D | D | D | — | — |
| 77 | A | D | D | D | — | — |
| 78 | A | D | D | D | — | — |
| 79 | A | D | D | D | — | — |
| 80 | A | D | D | D | — | — |
| 81 | A | D | D | D | — | — |
| 82 | A | D | D | D | — | — |

In Vitro Phospho-S6 and Phospho-Akt Cellular Assay

Activation of mTOR signaling results in phosphorylation of several downstream targets. In cells, mTOR exists in two different protein complexes. The mTOR Complex-1 (mTORC1) phosphorylates and activates S6 Kinase 1 (S6K1) and S6 Kinase 2 (S6K2) (also known as p70S6K) which then phosphorylate S6 Ribosomal Protein (S6RP) (also known as RPS6)3. S6RP is phosphorylated on serine 235, serine 236, serine 240 and serine 244 by both pS6K1 and pS6K2. The mTOR Complex-2 (mTORC2) phosphorylates AKT on serine 473 which activates the AKT signaling pathway.

The assay measures a test compound's inhibition of S6RP serine-240/244 phosphorylation and inhibition of Akt serine-473 phosphorylation in human embryonic kidney derived HEK293T/17 cells (ATCC CRL-11268).

The HEK293T/17 cell line is maintained in DMEM media (Invitrogen catalogue number 41965-039) supplemented with 10% FCS at 37° C. in a 5% CO2 humidified incubator.

Cells are seeded in 96-well plates at 40,000 cells/well (pS6RP S240/244 assay) or 80,000 cells/well (pAkt S473 assay) in 90 µl growth media (DMEM, 2% FCS). Plates are incubated for 1 hour in a humidified incubator to allow the cells to adhere. Cells are treated with 8 concentrations of test compounds or DMSO alone for controls (final DMSO concentration 0.1%) and incubated at 37° C. for 2 hours. Then 20 µl of 5× concentrated lysis buffer (750 mM NaCl, 100 mM Tris pH7.4, 5 mM ADTA, 5 mM EGTA, 5% Triton X-100) is added, plates are sealed and incubated for 15 minutes at 4° C. with gentle shaking. After cell lysis, 25 µl cell lysate is transferred to a MesoScale plate coated with an antibody to pS6RP Ser240/244 (MesoScale Discovery K150DGD-3) or an antibody to pAkt Ser 473 (MesoScale Discovery K151DGD-3). Plates have been blocked before by incubation with 150 µl MesoScale Discovery Blocking Solution-A for 1 hour at room temperature followed by washing with 150 µl 1× Tris wash buffer per well. After the transfer of the cell lysate to the MSD plate, the pS6RP (or pAkt) protein is captured on the coated antibody by incubation at room temperature for 1 hour with gentle shaking. After the capture step the plate is washed three times with 150 µl of 1× Tris wash buffer per well. Then 25 µl detection antibody conjugated with a Sulfo-Tag is added and incubated for 1 hour at room temperature with gentle shaking. Subsequently the antibody solution is removed and the plate is washed 3 times with 150 µl 1× Tris wash buffer per well and 150 µl Read buffer is added. The plates are analysed on a MSD 2400 Plate Reader (MesoScale Discovery). Data analysis is performed using nonlinear regression for a sigmoidal dose-response with a variable slope.

Cellular Assay Results

TABLE 13

Inhibition values (IC50 in uM)
(Activity level: A < 0.1 uM ≤ B < 1 uM ≤ C ≤ 10 uM < D)

| Example | pS6 | pAkt |
| --- | --- | --- |
| 1 | A | A |
| 2 | A | A |
| 3 | A | — |
| 4 | B | — |
| 5 | A | A |
| 6 | A | — |
| 7 | A | — |
| 8 | A | — |
| 9 | A | A |
| 10 | A | A |
| 11 | A | — |
| 12 | B | — |
| 13 | C | — |
| 14 | B | — |
| 15 | A | — |
| 16 | C | — |
| 17 | A | — |
| 18 | B | — |
| 19 | — | — |
| 20 | B | — |
| 21 | B | — |
| 22 | B | — |
| 23 | B | — |
| 24 | A | — |
| 25 | B | — |
| 26 | A | — |
| 27 | A | — |
| 28 | B | — |
| 29 | B | — |
| 30 | A | — |
| 31 | A | — |
| 32 | A | — |
| 33 | A | — |
| 34 | A | — |
| 35 | A | — |
| 36 | — | — |
| 37 | — | — |
| 38 | A | — |
| 39 | A | — |
| 40 | A | — |
| 41 | A | — |
| 42 | A | — |
| 43 | A | — |
| 44 | A | — |
| 45 | A | — |
| 46 | A | — |
| 47 | A | — |
| 48 | A | — |
| 49 | A | — |
| 50 | A | — |
| 51 | A | — |
| 52 | A | — |
| 53 | A | — |
| 54 | A | — |
| 55 | A | — |
| 56 | — | — |
| 57 | — | — |
| 58 | A | — |
| 59 | A | — |
| 60 | A | — |
| 61 | A | — |
| 62 | A | — |
| 63 | A | — |
| 64 | A | — |
| 65 | A | — |
| 66 | A | — |
| 67 | A | — |
| 68 | A | — |
| 69 | A | — |
| 70 | A | — |
| 71 | A | — |
| 72 | A | — |
| 73 | A | — |
| 74 | A | — |
| 75 | A | — |
| 76 | A | — |
| 77 | A | — |
| 78 | A | — |
| 79 | A | — |
| 80 | A | — |
| 81 | — | — |
| 82 | — | — |

In Vitro Human Whole Blood Assay

This assay measures IFNγ release in whole blood after αCD3/αCD28 and IL-2 treatment. The whole blood contains circulating T lymphocytes; αCD3/αCD28 stimulation mimics antigen receptor signalling, resulting in epigenetic changes to the IFNG gene locus, such that when IL-2 is added, IFNγ is produced.

Human whole blood, with Na-heparin as the anticoagulant, is obtained from Clinical Trials Laboratory Services. Blood is diluted 1.4 times with RPMI 1640 (Lonza, BE12-167F) and 175 μl/well is distributed in a low evaporation 96-well plates (Falcon, BD Labware, 353072). Blood is treated with 10 concentrations of test compounds or DMSO alone for controls (final DMSO concentration 0.2%) and incubated at 37° C. for 1 hour. Blood is then stimulated with 1 μg/ml αCD3 (R&D Systems, MAB100), 1 μg/ml αCD28 (BD Pharmingen, 555725) and IL-2 at 10 ng/ml (Peprotech, 200-02). Blood is then left to incubate at 37° C. for 18 hours. After, plates are spun at 250 g for 5 minutes to pellet blood cells and 25 μl of plasma is transferred to a MesoScale plate coated with an antibody to IFNγ (MesoScale Discovery K151AEC-2) containing 25 μl/well MesoScale Discovery Blocking Solution-2. Plates have been blocked by incubating with 25 μl/well MesoScale Discovery Blocking Solution-2 for 30 minutes at room temperature. After the transfer of sera to the MSD plate, the IFNγ protein is captured on the coated antibody by incubation at room temperature for 2 hour with gentle shaking. After the capture step the plate is washed three times with 150 μl/well of 1×PBS-Tween wash buffer and 25 μl/well detection antibody conjugated with a Sulfo-Tag is added and incubated for 2 hours at room temperature with gentle shaking. Subsequently the antibody solution is removed and the plate is washed 3 times with 150 μl/well 1×PBS-Tween wash buffer and 150 μl/well MesoScale Discovery Read buffer is added. The plates are analysed on a MSD 2400 Plate Reader (MesoScale Discovery). Data analysis is performed using nonlinear regression for a sigmoidal dose-response with a variable slope.

Whole Blood Assay Results

TABLE 14

| Inhibition values (pIC50) | |
|---|---|
| Example | WB |
| 38 | 6.8 |
| 39 | 7.0 |
| 40 | 6.7 |
| 41 | 6.6 |
| 42 | 6.6 |
| 43 | 6.0 |
| 44 | 7.4 |
| 45 | 6.4 |
| 46 | 5.7 |
| 47 | 7.1 |
| 48 | 7.1 |
| 49 | 6.7 |
| 50 | 6.0 |
| 51 | 6.8 |
| 52 | 7.5 |
| 53 | 7.2 |
| 54 | 6.7 |
| 55 | 7.0 |
| 56 | 6.5 |
| 57 | 6.6 |
| 58 | 6.6 |
| 59 | 7.0 |
| 60 | 6.7 |
| 61 | 6.6 |
| 62 | 6.7 |
| 63 | 6.6 |
| 64 | 6.8 |
| 65 | — |
| 66 | 6.0 |
| 67 | 6.5 |

TABLE 14-continued

| Inhibition values (pIC50) | |
|---|---|
| Example | WB |
| 68 | 6.5 |
| 69 | 6.9 |
| 70 | 6.8 |
| 71 | 6.1 |
| 72 | 6.4 |
| 73 | 7.2 |
| 74 | 6.3 |
| 75 | 6.9 |
| 76 | 6.2 |
| 77 | 6.7 |
| 78 | 6.3 |
| 79 | 6.2 |
| 80 | 7.0 |
| 81 | — |
| 82 | — |

Caco-2 Permeability

Bi-directional Caco-2 assays to assess the permeability of compounds in the gi tract, were performed as described below.

Caco-2 cells were obtained from European Collection of Cell Cultures (ECACC, cat 86010202) and used after a 21 day cell culture in 24-well Transwell plates (Fisher TKT-545-020B). $2 \times 10^5$ cells/well were seeded in plating medium consisting of DMEM+GlutaMAXI+1% NEAA+10% FBS (FetalClone II)+1% Pen/Strep. The medium was changed every 2-3 days. Test and reference compounds (propranolol and rhodamine123 or vinblastine, all purchased from Sigma) were prepared in Hanks' Balanced Salt Solution containing 25 mM HEPES (pH7.4) and added to either the apical (125 ul) or basolateral (600 ul) chambers of the Transwell plate assembly at a concentration of 10 uM with a final DMSO concentration of 0.25%.

50 uM Lucifer Yellow (Sigma) was added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer. After a 1 hr incubation at 37° C. while shaking at an orbital shaker at 150 rpm, 70 ul aliquots were taken from both apical (A) and basal (B) chambers and added to 100 ul 50:50 acetonitrile: water solution containing analytical internal standard (0.5 uM carbamazepine) in a 96 well plate.

Lucifer yellow was measured with a Spectramax Gemini XS (Ex 426 nm and Em 538 nm) in a clean 96 well plate containing 150 uL of liquid from basolateral and apical side.

Concentrations of compound in the samples were measured by high performance liquid-chromatography/mass spectroscopy (LC-MS/MS).

Apparent permeability (Papp) values were calculated from the relationship:

$$Papp = [\text{compound}]_{acceptor\,final} \times V_{acceptor} / ([\text{compound}]_{donor\,initial} \times V_{donor}) / T_{inc} \times V_{donor} / \text{surface area} \times 60 \times 10^{-6} \text{ cm/s}$$

where V=chamber volume $T_{inc}$=incubation time. Surface area=0.33 cm$^2$

The Efflux ratio, as an indication of active efflux from the apical cell surface of Caco-2 cells, was calculated using the ratio of Papp B>A/Papp A>B.

Caco-2 Assay Results

TABLE 15

| Efflux ratios | |
|---|---|
| Example | ER |
| 2 | 63 |
| 6 | 25 |
| 7 | 29 |
| 9 | 20 |
| 10 | 27 |
| 20 | 39 |
| 27 | 25 |
| 30 | 21 |
| 33 | 23 |
| 34 | 13 |
| 38 | 34 |
| 39 | 61 |
| 42 | 2.1 |
| 44 | 5.5 |
| 45 | 52 |
| 46 | 35 |
| 48 | 30 |
| 49 | 32 |
| 50 | 7 |
| 62 | 22 |
| 82 | 1.6 |

Pharmacokinetic Studies in Rodents

Animals

Sprague-Dawley rats (male, 7-9 weeks old) were obtained from SLAC Laboratory Animal Co Ltd (China). Rats were acclimatized for about 3 days before treatment and were kept on a 12 hr light/dark cycle. Temperature was maintained between 18 and 26° C. and relative humidity between 30 and 70%. Food and water were provided adlibitum. Animals were surgically implanted with either catheters in the carotid artery (for sampling) or in both the jugular vein (for dosing) and the carotid artery (for sampling) using polypropylene tube and heparin (50 i.u./mL)/glucose (50%) solutions as the lumen lock solution. Animals were allowed to recovered for at least 3 days after surgery.

Pharmacokinetic Study

Compounds were formulated in 5% DMSO (v/v), 95% (10% kleptose HPB (w/v) in saline for the intravenous route and in 0.5% HPMC, 2% w/v Poloxamer 188 (PluronicF68) in water for the oral route. Test compounds were orally dosed as a single esophageal gavage at 10 mg/kg in a dosing volume of 2 mg/ml and intravenously dosed as a bolus via the jugular vein at 1 mg/kg in a dosing volume of 0.5 mg/ml. Each group consisted of 3 rats. Blood samples were collected via the jugular vein with K-EDTA as anti-coagulant at the following time points: 0.08, 0.25, 0.5, 1, 2, 4 and 6 hrs (intravenous route), and 0.25, 0.5, 1, 2, 4, 6 and 8 hrs (oral route). Whole blood samples were centrifuged at 7000 rpm at 4° C. within 30 minutes of collection for 10 min and the resulting plasma samples were stored at −20° C. pending analysis.

Quantification of Compound Levels in Plasma

Plasma concentrations of each test compound were determined by an LC-MS/MS method with internal standards.

Determination of Pharmacokinetic Parameters

Pharmacokinetic parameters were calculated using the WinNonlin® software program (Pharsight®, Mountain View, Calif.)

Pharmacokinetics in rat for example compounds 2, 6 and 30 gave plasma levels ($C_{max}$) of 0.16 uM, 0.27 uM and 0.32 uM and oral bioavailabilities of 7%, 26%, and 69%, respectively.

The invention claimed is:

1. A compound of formula (I)

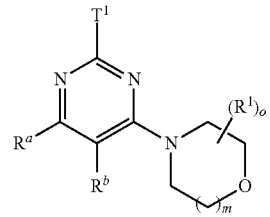

(I)

or a pharmaceutically acceptable salt thereof, wherein m is 1; or 2;

o is 1; 2; 3; or 4;

Each $R^1$ is independently selected from the group consisting of H; halogen; CN; $C(O)OR^2$; $OR^{2a}$; oxo (=O); $C(O)R^2$; $C(O)N(R^2R^{2a})$; $S(O)_2N(R^2R^{2a})$; $S(O)N(R^2R^{2a})$; $S(O)_2R^2$; $S(O)R^2$; $N(R^2)S(O)_2N(R^{2a}R^{2b})$; $N(R^2)S(O)N(R^{2a}R^{2b})$; $SR^2$; $N(R^2R^{2a})$; $NO_2$; $OC(O)R^2$; $N(R^2)C(O)R^{2a}$; $N(R^2)S(O)_2R^{2a}$; $N(R^2)S(O)R^{2a}$; $N(R^2)C(O)N(R^{2a}R^{2b})$; $N(R^2)C(O)OR^{2a}$; $OC(O)N(R^2R^{2a})$; and $C_{1-6}$ alkyl, wherein $C_{1-6}$ alkyl is optionally substituted with one or more $R^3$, which are the same or different;

Optionally two $R^1$ are joined to form together with the ring to which they are attached an 8 to 11 membered heterobicycle;

$R^2$, $R^{2a}$, $R^{2b}$ are independently selected from the group consisting of H; $C_{1-6}$ alkyl, wherein $C_{1-6}$ alkyl is optionally substituted with one or more halogen, which are the same or different;

$R^3$ is halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $NO_2$; $OC(O)R^4$; $N(R^4)C(O)R^{4a}$; $N(R^4)S(O)_2R^{4a}$; $N(R^4)S(O)R^{4a}$; $N(R^4)C(O)N(R^{4a}R^{4b})$; $N(R^4)C(O)OR^{4a}$; or $OC(O)N(R^4R^{4a})$;

$R^4$, $R^{4a}$, $R^{4b}$ are independently selected from the group consisting of H; and $C_{1-6}$ alkyl, wherein $C_{1-6}$ alkyl is optionally substituted with one or more halogen, which are the same or different;

$T^1$ is phenyl; or 5 to 6 membered aromatic heterocycle, wherein $T^1$ is substituted with $N(R^{5a})C(O)N(R^{5b}R^5)$ or $N(R^{5a})C(O)OR^5$ and optionally further substituted with one or more $R^6$, which are the same or different;

$R^6$ is halogen; CN; $C(O)OR^7$; $OR^7$; $C(O)R^7$; $C(O)N(R^7R^{7a})$; $S(O)_2N(R^7R^{7a})$; $S(O)N(R^7R^{7a})$; $S(O)_2R^7$; $S(O)R^7$; $N(R^7)S(O)_2N(R^{7a}R^{7b})$; $N(R^7)S(O)N(R^{7a}R^{7b})$; $SR^7$; $N(R^7R^{7a})$; $NO_2$; $OC(O)R^7$; $N(R^7)C(O)R^{7a}$; $N(R^7)S(O)_2R^{7a}$; $N(R^7)S(O)R^{7a}$; $N(R^7)C(O)N(R^{7a}R^{7b})$; $N(R^7)C(O)OR^{7a}$; $OC(O)N(R^7R^{7a})$; or $C_{1-6}$ alkyl, wherein $C_{1-6}$ alkyl is optionally substituted with one or more halogen, which are the same or different;

$R^{5a}$, $R^{5b}$, $R^7$, $R^{7a}$, $R^{7b}$ are independently selected from the group consisting of H; $C_{1-6}$ alkyl, wherein $C_{1-6}$ alkyl is optionally substituted with one or more halogen, which are the same or different;

$R^5$ is H; $T^2$; and $C_{1-6}$ alkyl, wherein $C_{1-6}$ alkyl is optionally substituted with one or more $R^8$, which are the same or different;

$R^8$ is halogen; CN; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $N(R^9)S(O)N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; $OC(O)N(R^9R^{9a})$; or $T^2$;

R$^9$, R$^{9a}$, R$^{9b}$ are independently selected from the group consisting of H; and C$_{1-6}$ alkyl, wherein C$_{1-6}$ alkyl is optionally substituted with one or more halogen, which are the same or different;

Optionally R$^5$, R$^{5b}$ are joined to form together with the nitrogen atom to which they are attached an at least the nitrogen atom as ring heteroatom containing 4 to 7 membered heterocyclyl ring; or 8 to 11 membered heterobicyclyl ring, wherein the 4 to 7 membered heterocyclyl ring; and the 8 to 11 membered heterobicyclyl ring are optionally substituted with one or more R$^{10}$, which are the same or different;

T$^2$ is C$_{3-7}$ cycloalkyl; 4 to 7 membered heterocyclyl; 8 to 11 membered heterobicyclyl; phenyl; naphthyl; indenyl; or indanyl, wherein T$^2$ is optionally substituted with one or more R$^{10}$, which are the same or different;

R$^{10}$ is halogen; CN; C(O)OR$^{11}$; OR$^{11}$; oxo (=O), where the ring is at least partially saturated; C(O)R$^{11}$; C(O)N(R$^{11}$R$^{11a}$); S(O)$_2$N(R$^{11}$R$^{11a}$); S(O)N(R$^{11}$R$^{11a}$); S(O)$_2$R$^{11}$; S(O)R$^{11}$; N(R$^{11}$)S(O)$_2$N(R$^{11a}$R$^{11b}$); N(R$^{11}$)S(O)N(R$^{11a}$R$^{11b}$); SR$^{11}$; N(R$^{11}$R$^{11a}$); NO$_2$; OC(O)R$^{11}$; N(R$^{11}$)C(O)R$^{11a}$; N(R$^{11}$)S(O)$_2$R$^{11a}$; N(R$^{11}$)S(O)R$^{11a}$; N(R$^{11}$)C(O)N(R$^{11a}$R$^{11b}$); N(R$^{11}$)C(O)OR$^{11a}$; OC(O)N(R$^{11}$R$^{11a}$); or C$_{1-6}$ alkyl, wherein C$_{1-6}$ alkyl is optionally substituted with one or more R$^{12}$, which are the same or different;

R$^{11}$, R$^{11a}$, R$^{11b}$ are independently selected from the group consisting of H; C$_{1-6}$ alkyl, wherein C$_{1-6}$ alkyl is optionally substituted with one or more halogen, which are the same or different;

R$^{12}$ is halogen; CN; C(O)OR$^{13}$; OR$^{13}$; C(O)R$^{13}$; C(O)N(R$^{13}$R$^{13a}$); S(O)$_2$N(R$^{13}$R$^{13a}$); S(O)N(R$^{13}$R$^{13a}$); S(O)$_2$R$^{13}$; S(O)R$^{13}$; N(R$^{13}$)S(O)$_2$N(R$^{13a}$R$^{13b}$); N(R$^{13}$)S(O)N(R$^{13a}$R$^{13b}$); SR$^{13}$; N(R$^{13}$R$^{13a}$); NO$_2$; OC(O)R$^{13}$; N(R$^{13}$)C(O)R$^{13a}$; N(R$^{13}$)S(O)$_2$R$^{13a}$; N(R$^{13}$)S(O)R$^{13a}$; N(R$^{13}$)C(O)N(R$^{13a}$R$^{13b}$); N(R$^{13}$)C(O)OR$^{13a}$; or OC(O)N(R$^{13}$R$^{13a}$);

R$^{13}$, R$^{13a}$, R$^{13b}$ are independently selected from the group consisting of H; and C$_{1-6}$ alkyl, wherein C$_{1-6}$ alkyl is optionally substituted with one or more halogen, which are the same or different;

R$^a$, R$^b$ are joined to form —(CR$^{14}$R$^{14a}$)$_p$—S(O)$_r$—(CR$^{14b}$R$^{14c}$)$_q$—;

r is 0; 1; or 2;

p, q are 0; 1; 2; or 3, provided that p+q is 2; 3; or 4;

R$^{14}$, R$^{14a}$, R$^{14b}$, R$^{14c}$ are independently selected from the group consisting of H; halogen; CN; C(O)OR$^{15}$; OR$^{15}$; C(O)R$^{15}$; C(O)N(R$^{15}$R$^{15a}$); S(O)$_2$N(R$^{15}$R$^{15a}$); S(O)N(R$^{15}$R$^{15a}$); S(O)$_2$R$^{15}$; S(O)R$^{15}$; N(R$^{15}$)S(O)$_2$N(R$^{15a}$R$^{15b}$); N(R$^{15}$)S(O)N(R$^{15a}$R$^{15b}$); SR$^{15}$; N(R$^{15}$R$^{15a}$); NO$_2$; OC(O)R$^{15}$; N(R$^{15}$)C(O)R$^{15a}$; N(R$^{15}$)S(O)$_2$R$^{15a}$; N(R$^{15}$)S(O)R$^{15a}$; N(R$^{15}$)C(O)N(R$^{15a}$R$^{15b}$); N(R$^{15}$)C(O)OR$^{15a}$; OC(O)N(R$^{15}$R$^{5a}$); or C$_{1-6}$ alkyl, wherein C$_{1-6}$ alkyl is optionally substituted with one or more R$^{16}$, which are the same or different;

Optionally one of the pairs R$^{14}$, R$^{14a}$ and R$^{14b}$, R$^{14c}$ or both pairs form an oxo group (=O);

Optionally one of the pairs selected from the group consisting of R$^{14}$, R$^{14a}$; R$^{14}$, R$^{14b}$; two adjacent R$^{14}$, in case p>1; and two adjacent R$^{14b}$, in case q>1, are joined to form together with the ring to which they are attached an 6 to 11 membered heterobicycle;

R$^{15}$, R$^{15a}$, R$^{15b}$ are independently selected from the group consisting of H; C$_{1-6}$ alkyl, wherein C$_{1-6}$ alkyl is optionally substituted with one or more halogen, which are the same or different;

R$^{16}$ is halogen; CN; C(O)OR$^{17}$; OR$^{17}$; C(O)R$^{17}$; C(O)N(R$^{17}$R$^{17a}$); S(O)$_2$N(R$^{17}$R$^{17a}$); S(O)N(R$^{17}$R$^{17a}$); S(O)$_2$R$^{17}$; S(O)R$^{17}$; N(R$^{17}$)S(O)$_2$N(R$^{17a}$R$^{17b}$); N(R$^{17}$)S(O)N(R$^{17a}$R$^{17b}$); SR$^{17}$; N(R$^{17}$R$^{17a}$); NO$_2$; OC(O)R$^{17}$; N(R$^{17}$)C(O)R$^{17a}$; N(R$^{17}$)S(O)$_2$R$^{17a}$; N(R$^{17}$)S(O)R$^{17a}$; N(R$^{17}$)C(O)N(R$^{17a}$R$^{17b}$); N(R$^{17}$)C(O)OR$^{17a}$; or OC(O)N(R$^{17}$R$^{17a}$);

R$^{17}$, R$^{17a}$, R$^{17b}$ are independently selected from the group consisting of H; C$_{1-6}$ alkyl, wherein C$_{1-6}$ alkyl is optionally substituted with one or more halogen, which are the same or different.

2. The compound of claim 1, wherein in formula (I) R$^a$ and R$^b$ are selected to give one of formulae (Ia) to (Ip):

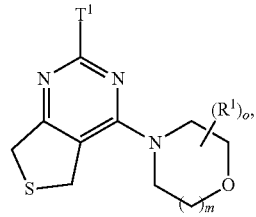

(Ia)

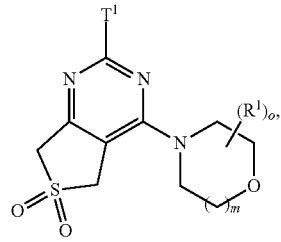

(Ib)

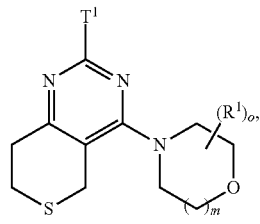

(Ic)

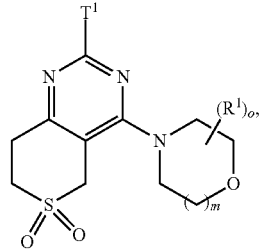

(Id)

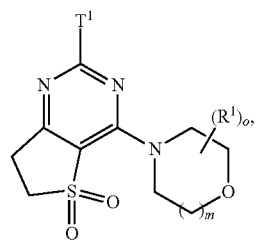

(Ie)

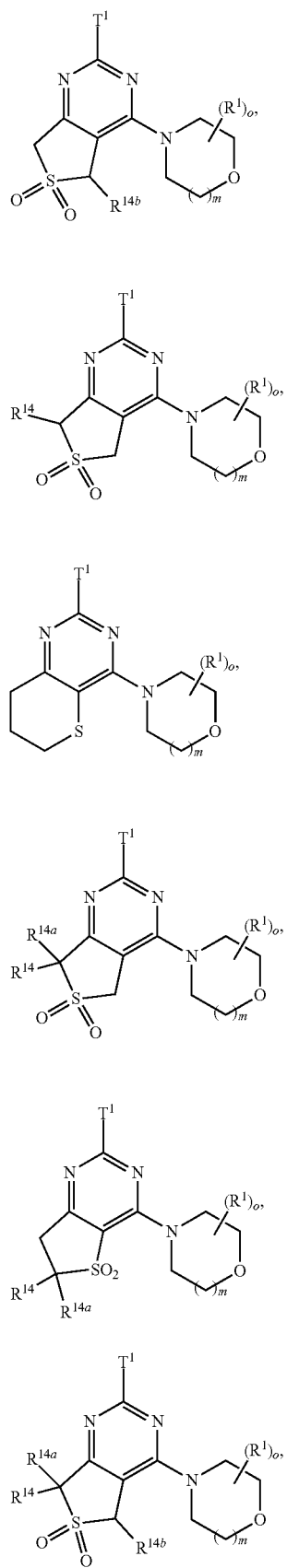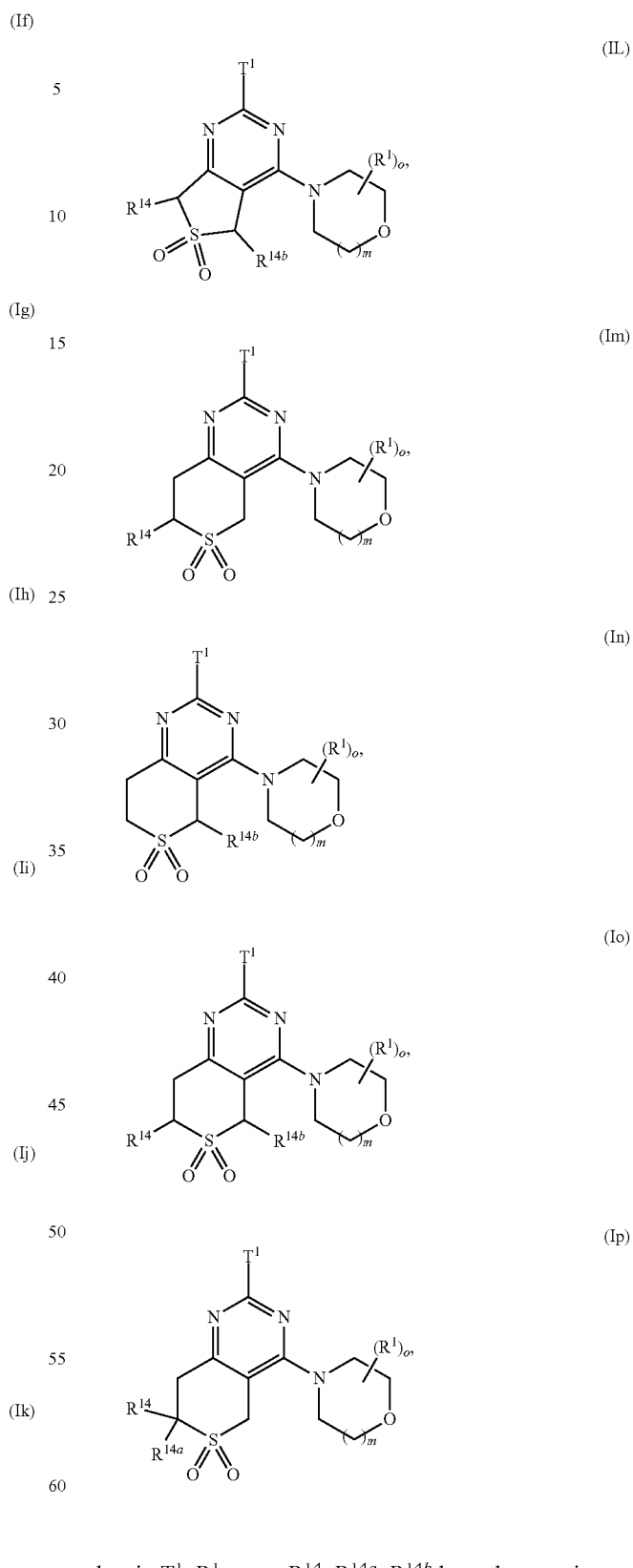
wherein $T^1$, $R^1$, o, m, $R^{14}$, $R^{14a}$, $R^{14b}$ have the meaning as indicated in claim 1.
3. The compound of claim 1, wherein in formula (I) $T^1$ is defined to give formula (Iq)

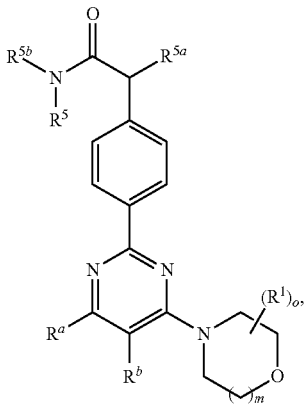

(Iq)

wherein o, m, $R^1$, $R^a$, $R^b$, $R^5$, $R^{5a}$, $R^{5b}$ have the meaning as indicated in claim 1.

4. The compound of claim 1, wherein $R^{5a}$, $R^{5b}$ are H, and $R^5$ is $C_{1-6}$ alkyl optionally substituted with one or more $R^8$, which are the same or different and selected from the group consisting of F; $OR^9$; and $N(R^9R^{9a})$.

5. The compound of claim 1, wherein $R^{14}$, $R^{14a}$, $R^{14b}$, $R^{14c}$ are independently selected from the group consisting of H; F; ethyl; and methyl.

6. The compound of claim 1, wherein $R^1$ is unsubstituted $C_{1-6}$ alkyl; or $C_{1-6}$ alkyl substituted with one $R^3$.

7. The compound of claim 1, wherein two $R^1$ are joined to form together with the ring to which they are attached an 8-oxa-3-azabicyclo[3.2.1]octan-3-yl or an 3-oxa-8-azabicyclo[3.2.1]octan-8-yl ring.

8. The compound of claim 1, wherein in formula (I) $R^a$, $R^b$, $T^1$ are defined to give formula (Ir):

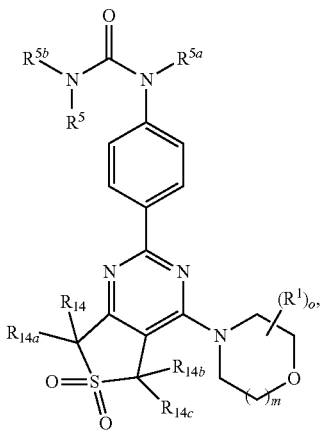

(Ir)

wherein $R^5$, $R^{5a}$, $R^{5b}$, $R^{14}$, $R^{14a}$, $R^{14b}$, $R^{14c}$, $R^1$, o, m are defined as in claim 1.

9. The compound of claim 1, wherein $R^{5b}$ and $R^{5a}$ are H and $R^5$ is $C_{1-6}$ alkyl, or $C_{3-7}$ cycloalkyl, wherein $C_{1-6}$ alkyl is optionally substituted with one or more $R^8$, which are the same or different and $C_{3-7}$ cycloalkyl is optionally substituted with one or more $R^{10}$, which are the same or different.

10. The compound of claim 1, wherein $R^5$ is cyclopropyl, methyl, ethyl, fluoroethyl, hydroxyethyl, difluoroethyl, isopropyl, fluoropropyl, pyridinyl and oxetanyl.

11. The compound of claim 1, wherein $(R^1)_o$ is attached at the 3 position.

12. The compound of claim 1 or a pharmaceutically acceptable salt thereof, wherein the compound is selected from the group consisting of:
  1-cyclopropyl-3-(4-(4-morpholino-6,6-dioxido-5,7-dihydrothieno[3,4-d]pyrimidin-2-yl)phenyl)urea;
  1-cyclopropyl-3-(4-(4-((2S,6R)-2,6-dimethylmorpholino)-6,6-dioxido-5,7-dihydrothieno[3,4-d]pyrimidin-2-yl)phenyl)urea;
  (S)-1-cyclopropyl-3-(4-(4-(3-methylmorpholino)-5,7-dihydrothieno[3,4-d]pyrimidin-2-yl)phenyl)urea;
  (S)-1-cyclopropyl-3-(4-(4-(3-methylmorpholino)-6,6-dioxido-5,7-dihydrothieno[3,4-d]pyrimidin-2-yl)phenyl)urea;
  (S)-1-ethyl-3-(4-(4-(3-methylmorpholino)-6,6-dioxido-5,7-dihydrothieno[3,4-d]pyrimidin-2-yl)phenyl)urea;
  (S)-1-methyl-3-(4-(4-(3-methylmorpholino)-6,6-dioxido-5,7-dihydrothieno[3,4-d]pyrimidin-2-yl)phenyl)urea;
  (S)-1-(2-hydroxyethyl)-3-(4-(4-(3-methylmorpholino)-6,6-dioxido-5,7-dihydrothieno[3,4-d]pyrimidin-2-yl)phenyl)urea;
  (S)-1-(2-fluoroethyl)-3-(4-(4-(3-methylmorpholino)-6,6-dioxido-5,7-dihydrothieno[3,4-d]pyrimidin-2-yl)phenyl)urea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-ethylurea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-(2-hydroxyethyl)urea;
  (R)-1-cyclopropyl-3-(4-(4-(3-methylmorpholino)-6,6-dioxido-5,7-dihydrothieno[3,4-d]pyrimidin-2-yl)phenyl)urea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-cyclopropylurea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-methylurea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-(2-fluoroethyl)urea;
  (S)-1-cyclopropyl-3-(4-(4-(3-methylmorpholino)-6,6-dioxido-7,8-dihydro-5H-thiopyrano[4,3-d]pyrimidin-2-yl)phenyl)urea;
  (S)-1-cyclopropyl-3-(4-(4-(3-methylmorpholino)-7,8-dihydro-5H-thiopyrano[4,3-d]pyrimidin-2-yl)phenyl)urea;
  (S)-1-(2,2-difluoroethyl)-3-(4-(4-(3-methylmorpholino)-6,6-dioxido-5,7-dihydrothieno[3,4-d]pyrimidin-2-yl)phenyl)urea;
  1-(4-(4-(8-oxa-3-azabicyclo[3.2.1]octan-3-yl)-6,6-dioxido-5,7-dihydrothieno[3,4-d]pyrimidin-2-yl)phenyl)-3-(2,2-difluoroethyl)urea;
  (S)-1-isopropyl-3-(4-(4-(3-methylmorpholino)-6,6-dioxido-5,7-dihydrothieno[3,4-d]pyrimidin-2-yl)phenyl)urea;
  1-(4-(4-(3-oxa-8-azabicyclo[3.2.1]octan-8-yl)-6,6-dioxido-5,7-dihydrothieno[3,4-d]pyrimidin-2-yl)phenyl)-3-cyclopropylurea;
  1-cyclopropyl-3-(4-(4-(3-ethylmorpholino)-6,6-dioxido-5,7-dihydrothieno[3,4-d]pyrimidin-2-yl)phenyl)urea;
  (S)-1-(3-fluoropropyl)-3-(4-(4-(3-methylmorpholino)-6,6-dioxido-5,7-dihydrothieno[3,4-d]pyrimidin-2-yl)phenyl)urea;

1-(4-(4-(8-oxa-3-azabicyclo[3.2.1]octan-3-yl)-6,6-di-oxido-5,7-dihydrothieno[3,4-d]pyrimidin-2-yl)phenyl)-3-(3-fluoropropyl)urea;

1-cyclopropyl-3-(4-(7-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(4-(3-methylmorpholino)-5,5-dioxido-6,7-dihydrothieno[3,2-d]pyrimidin-2-yl)phenyl)urea;

(S)-1-cyclopropyl-3-(4-(4-(3-methylmorpholino)-7,8-dihydro-6H-thiopyrano[3,2-d]pyrimidin-2-yl)phenyl)urea;

1-cyclopropyl-3-(4-(5-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(7,7-dimethyl-4-(3-methylmorpholino)-6,6-dioxido-5,7-dihydrothieno[3,4-d]pyrimidin-2-yl)phenyl)urea;

1-cyclopropyl-3-(4-(5-methyl-4-morpholino-6,6-dioxido-5,7-dihydrothieno[3,4-d]pyrimidin-2-yl)phenyl)urea;

1-cyclopropyl-3-(4-(4-(3-ethylmorpholino)-5-methyl-6,6-dioxido-5,7-dihydrothieno[3,4-d]pyrimidin-2-yl)phenyl)urea;

1-(4-(4-(3-oxa-8-azabicyclo[3.2.1]octan-8-yl)-5-methyl-6,6-dioxido-5,7-dihydrothieno[3,4-d]pyrimidin-2-yl)phenyl)-3-cyclopropylurea;

1-(4-(4-(8-oxa-3-azabicyclo[3.2.1]octan-3-yl)-5-methyl-6,6-dioxido-5,7-dihydrothieno[3,4-d]pyrimidin-2-yl)phenyl)-3-cyclopropylurea;

(S)-1-(4-(4-(3-methylmorpholino)-6,6-dioxido-5,7-dihydrothieno[3,4-d]pyrimidin-2-yl)phenyl)-3-(pyridin-4-yl)urea;

(S)-1-(4-(4-(3-methylmorpholino)-6,6-dioxido-5,7-dihydrothieno[3,4-d]pyrimidin-2-yl)phenyl)-3-(pyridin-3-yl)urea;

1-cyclopropyl-3-(4-((R)-5-methyl-4-((S)-3-methylmorpholino)-6,6-dioxido-5,7-dihydrothieno[3,4-d]pyrimidin-2-yl)phenyl)urea;

1-cyclopropyl-3-(4-((S)-5-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(6,6-dimethyl-4-(3-methylmorpholino)-5,5-dioxido-6,7-dihydrothieno[3,2-d]pyrimidin-2-yl)phenyl)urea;

1-ethyl-3-(4-(5-methyl-4-((S)-3-methylmorpholino)-6,6-dioxido-5,7-dihydrothieno[3,4-d]pyrimidin-2-yl)phenyl)urea;

1-ethyl-3-(4-((R)-5-methyl-4-((S)-3-methylmorpholino)-6,6-dioxido-5,7-dihydrothieno[3,4-d]pyrimidin-2-yl)phenyl)urea;

1-ethyl-3-(4-((S)-5-methyl-4-((S)-3-methylmorpholino)-6,6-dioxido-5,7-dihydrothieno[3,4-d]pyrimidin-2-yl)phenyl)urea;

1-ethyl-3-(4-(4-((S)-3-ethylmorpholino)-7-methyl-6,6-dioxido-5,7-dihydrothieno[3,4-d]pyrimidin-2-yl)phenyl)urea;

1-ethyl-3-(4-(5,7,7-trimethyl-4-((S)-3-methylmorpholino)-6,6-dioxido-5,7-dihydrothieno[3,4-d]pyrimidin-2-yl)phenyl)urea;

1-cyclopropyl-3-(4-(7-fluoro-7-methyl-4-((S)-3-methylmorpholino)-6,6-dioxido-5,7-dihydrothieno[3,4-d]pyrimidin-2-yl)phenyl)urea;

1-cyclopropyl-3-(4-(5,7-dimethyl-4-((S)-3-methylmorpholino)-6,6-dioxido-5,7-dihydrothieno[3,4-d]pyrimidin-2-yl)phenyl)urea;

1-(4-(5-methyl-4-((S)-3-methylmorpholino)-6,6-dioxido-5,7-dihydrothieno[3,4-d]pyrimidin-2-yl)phenyl)-3-propylurea;

1-(cyclopropylmethyl)-3-(4-(5-methyl-4-((S)-3-methylmorpholino)-6,6-dioxido-5,7-dihydrothieno[3,4-d]pyrimidin-2-yl)phenyl)urea;

1-cyclopropyl-3-(4-(4-((S)-3-ethylmorpholino)-5-methyl-6,6-dioxido-5,7-dihydrothieno[3,4-d]pyrimidin-2-yl)phenyl)urea;

1-cyclopropyl-3-(4-(5-methyl-4-((R)-3-methylmorpholino)-6,6-dioxido-5,7-dihydrothieno[3,4-d]pyrimidin-2-yl)phenyl)urea;

1-cyclopropyl-3-(4-(5-ethyl-4-((S)-3-methylmorpholino)-6,6-dioxido-5,7-dihydrothieno[3,4-d]pyrimidin-2-yl)phenyl)urea;

1-ethyl-3-(2-fluoro-4-(5-methyl-4-((S)-3-methylmorpholino)-6,6-dioxido-5,7-dihydrothieno[3,4-d]pyrimidin-2-yl)phenyl)urea;

(S)-1-cyclopropyl-3-(4-(4-(3-ethylmorpholino)-7,7-dimethyl-6,6-dioxido-5,7-dihydrothieno[3,4-d]pyrimidin-2-yl)phenyl)urea;

1-ethyl-3-(4-((R)-4-((S)-3-ethylmorpholino)-5-methyl-6,6-dioxido-5,7-dihydrothieno[3,4-d]pyrimidin-2-yl)phenyl)urea;

1-ethyl-3-(4-((S)-4-((S)-3-ethylmorpholino)-5-methyl-6,6-dioxido-5,7-dihydrothieno[3,4-d]pyrimidin-2-yl)phenyl)urea;

(R)-1-cyclopropyl-3-(4-(7,7-dimethyl-4-(3-methylmorpholino)-6,6-dioxido-5,7-dihydrothieno[3,4-d]pyrimidin-2-yl)phenyl)urea;

(R)-1-(4-(7,7-dimethyl-4-(3-methylmorpholino)-6,6-dioxido-5,7-dihydrothieno[3,4-d]pyrimidin-2-yl)phenyl)-3-ethylurea;

(S)-1-ethyl-3-(4-(4-(3-ethylmorpholino)-7,7-dimethyl-6,6-dioxido-5,7-dihydrothieno[3,4-d]pyrimidin-2-yl)phenyl)urea;

(S)-1-(4-(7,7-dimethyl-4-(3-methylmorpholino)-6,6-dioxido-5,7-dihydrothieno[3,4-d]pyrimidin-2-yl)phenyl)-3-methylurea;

1-methyl-3-(4-(5-methyl-4-((S)-3-methylmorpholino)-6,6-dioxido-5,7-dihydrothieno[3,4-d]pyrimidin-2-yl)phenyl)urea;

1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-cyclopropylurea;

1-(4-(4-(3-oxa-8-azabicyclo[3.2.1]octan-8-yl)-7,7-dimethyl-6,6-dioxido-5,7-dihydrothieno[3,4-d]pyrimidin-2-yl)phenyl)-3-ethylurea;

(S)-1-(4-(7,7-dimethyl-4-(3-methylmorpholino)-6,6-dioxido-5,7-dihydrothieno[3,4-d]pyrimidin-2-yl)phenyl)-3-(2-fluoroethyl)urea;

(S)-1-(4-(7,7-dimethyl-4-(3-methylmorpholino)-6,6-dioxido-5,7-dihydrothieno[3,4-d]pyrimidin-2-yl)phenyl)-3-ethylurea;

1-cyclopropyl-3-(4-((S)-5-methyl-4-((R)-3-methylmorpholino)-6,6-dioxido-5,7-dihydrothieno[3,4-d]pyrimidin-2-yl)phenyl)urea;

(S)-1-(4-(4-(3-ethylmorpholino)-7,7-dimethyl-6,6-dioxido-5,7-dihydrothieno[3,4-d]pyrimidin-2-yl)-2-fluorophenyl)-3-methylurea;

(S)-1-(4-(7,7-dimethyl-4-(3-methylmorpholino)-6,6-dioxido-5,7-dihydrothieno[3,4-d]pyrimidin-2-yl)-2-fluorophenyl)-3-methylurea;

(S)-1-(4-(7,7-dimethyl-4-(3-methylmorpholino)-6,6-dioxido-5,7-dihydrothieno[3,4-d]pyrimidin-2-yl)-3-fluorophenyl)-3-methylurea;

1-ethyl-3-(4-(5-ethyl-4-((S)-3-methylmorpholino)-6,6-dioxido-5,7-dihydrothieno[3,4-d]pyrimidin-2-yl)phenyl)urea;

(S)-1-(4-(7,7-dimethyl-4-(3-methylmorpholino)-6,6-dioxido-5,7-dihydrothieno[3,4-d]pyrimidin-2-yl)phenyl)-3-(oxetan-3-yl)urea;

(S)-1-(4-(7,7-dimethyl-4-(3-methylmorpholino)-6,6-dioxido-5,7-dihydrothieno[3,4-d]pyrimidin-2-yl)-3-fluorophenyl)-3-ethylurea;

(S)-1-cyclopropyl-3-(4-(7,7-dimethyl-4-(3-methylmorpholino)-6,6-dioxido-7,8-dihydro-5H-thiopyrano[4,3-d]pyrimidin-2-yl)phenyl)urea;

1-cyclopropyl-3-(4-(7-methyl-4-((S)-3-methylmorpholino)-6,6-dioxido-7,8-dihydro-5H-thiopyrano[4,3-d]pyrimidin-2-yl)phenyl)urea;

1-cyclopropyl-3-(4-(5,7-dimethyl-4-((S)-3-methylmorpholino)-6,6-dioxido-7,8-dihydro-5H-thiopyrano[4,3-d]pyrimidin-2-yl)phenyl)urea;

(S)-1-(4-(7,7-dimethyl-4-(3-methylmorpholino)-6,6-dioxido-7,8-dihydro-5H-thiopyrano[4,3-d]pyrimidin-2-yl)phenyl)-3-ethylurea;

1-cyclopropyl-3-(4-(5-methyl-4-((S)-3-methylmorpholino)-6,6-dioxido-7,8-dihydro-5H-thiopyrano[4,3-d]pyrimidin-2-yl)phenyl)urea;

1-(2-fluoroethyl)-3-(4-(5,7,7-trimethyl-4-((S)-3-methylmorpholino)-6,6-dioxido-5,7-dihydrothieno[3,4-d]pyrimidin-2-yl)phenyl)urea;

1-(4-(7,7-dimethyl-4-morpholino-6,6-dioxido-5,7-dihydrothieno[3,4-d]pyrimidin-2-yl)phenyl)-3-ethylurea;

1-methyl-3-(4-(5,7,7-trimethyl-4-((S)-3-methylmorpholino)-6,6-dioxido-5,7-dihydrothieno[3,4-d]pyrimidin-2-yl)phenyl)urea;

1-(3-fluoro-4-(5,7,7-trimethyl-4-((S)-3-methylmorpholino)-6,6-dioxido-5,7-dihydrothieno[3,4-d]pyrimidin-2-yl)phenyl)-3-methylurea;

1-(4-(4-((S)-3-ethylmorpholino)-5,7,7-trimethyl-6,6-dioxido-5,7-dihydrothieno[3,4-d]pyrimidin-2-yl)-3-fluorophenyl)-3-methylurea;

1-(4-(4-((S)-3-ethylmorpholino)-5,7,7-trimethyl-6,6-dioxido-5,7-dihydrothieno[3,4-d]pyrimidin-2-yl)phenyl)-3-methylurea;

1-(2-fluoroethyl)-3-(4-(5,7,7-trimethyl-4-morpholino-6,6-dioxido-5,7-dihydrothieno[3,4-d]pyrimidin-2-yl)phenyl)urea; and 1-cyclopropyl-3-(4-((R)-5,7,7-trimethyl-4-((S)-3-methylmorpholino)-6,6-dioxido-5,7-dihydrothieno[3,4-d]pyrimidin-2-yl)phenyl)urea.

13. A pharmaceutical composition comprising a compound or a pharmaceutically acceptable salt thereof of claim 1 and a pharmaceutically acceptable carrier.

14. The pharmaceutical composition of claim 13, further comprising one or more other pharmaceutical compositions.

15. A method of treating a disease or disorder associated with mTOR selected from an immunological, inflammatory or autoimmune disease, an allergic disorder or disease, transplant rejection, a Graft-versus host disease, a proliferative disease, a cardiovascular, metabolic or neurodegenerative disease, an autophagy associated disease, and a viral infection, comprising administering the compound or a pharmaceutically acceptable salt thereof of claim 1.

* * * * *